US007517670B2

(12) United States Patent
Umaña et al.

(10) Patent No.: US 7,517,670 B2
(45) Date of Patent: *Apr. 14, 2009

(54) GLYCOSYLATION ENGINEERING OF ANTIBODIES FOR IMPROVING ANTIBODY-DEPENDENT CELLULAR CYTOTOXICITY

(75) Inventors: Pablo Umaña, Zürich (CH); Joël Jean-Mairet, Zürich (CH); James E Bailey, Zürich (CH); M. Sean Bailey, legal representative, Santa Monica, CA (US)

(73) Assignee: GlycArt Biotechnology AG, Schlieren-Zürich ( * ) Notice: Subject to any disclaimer, the term of this patent is extended or adjusted under 35 U.S.C. 154(b) by 0 days.

This patent is subject to a terminal disclaimer.

(21) Appl. No.: 10/633,697

(22) Filed: Aug. 5, 2003

(65) Prior Publication Data

US 2005/0079605 A1      Apr. 14, 2005

Related U.S. Application Data

(62) Division of application No. 09/294,584, filed on Apr. 20, 1999, now Pat. No. 6,602,684.

(60) Provisional application No. 60/082,581, filed on Apr. 20, 1998.

(51) Int. Cl.
*C12N 15/12* (2006.01)
*C12N 15/63* (2006.01)
*A61K 39/00* (2006.01)

(52) U.S. Cl. .................. 435/69.1; 435/320.1; 435/455; 435/456

(58) Field of Classification Search ........................ None
See application file for complete search history.

(56) References Cited

U.S. PATENT DOCUMENTS

| | | | |
|---|---|---|---|
| 4,215,051 A | 7/1980 | Schroeder et al. | |
| 4,946,778 A | 8/1990 | Ladner et al. | |
| 4,978,745 A | 12/1990 | Schoemaker et al. | |
| 5,047,335 A | 9/1991 | Paulson et al. | |
| 5,529,922 A | 6/1996 | Chapman et al. | |
| 5,547,933 A | 8/1996 | Lin | |
| 5,736,137 A | 4/1998 | Anderson et al. | |
| 5,753,229 A | 5/1998 | Mordoh et al. | |
| 5,776,456 A | 7/1998 | Anderson et al. | |
| 5,843,439 A | 12/1998 | Anderson et al. | |
| 5,939,068 A * | 8/1999 | Brams et al. ............. | 424/133.1 |
| 5,952,203 A | 9/1999 | Withers et al. | |
| 5,958,403 A | 9/1999 | Strom et al. | |
| 6,153,433 A | 11/2000 | Miyoshi et al. | |
| 6,183,744 B1 * | 2/2001 | Goldenberg ............. | 424/141.1 |
| 6,602,684 B1 * | 8/2003 | Umana et al. ............. | 435/69.1 |
| 2003/0175884 A1 | 9/2003 | Umaña et al. | |
| 2004/0072290 A1 | 4/2004 | Umaña et al. | |

FOREIGN PATENT DOCUMENTS

| | | |
|---|---|---|
| AU | 2002307037 B2 | 10/2002 |
| EP | 0 475 354 A2 | 3/1992 |
| EP | 0 669 836 B1 | 7/1996 |
| EP | 0 752 248 A1 | 1/1997 |
| WO | WO 94/11026 | 5/1994 |
| WO | WO 95/24494 | 9/1995 |
| WO | WO 97/30087 | 8/1997 |
| WO | WO 97/30087 A1 | 8/1997 |
| WO | WO 98/06835 A2 | 2/1998 |
| WO | WO 99/54342 A1 | 10/1999 |
| WO | WO 02/079255 A1 | 10/2002 |

OTHER PUBLICATIONS

Raju et al., 2000, Glycobiology, vol. 10, No. 5, pp. 477-486.*
Shinkawa et al., 2003, J. Biol. Chem., vol. 278, No. 5, pp. 3466-3473.*
Amstutz, H., et al., "Production and Characterization of a Mouse/Human Chimeric Antibody Directed Against Human Neuroblastoma," *Int. J. Cancer* 53:147-152, Wiley-Liss, Inc. (1993).
Anderson, W.F., "Human gene therapy," *Nature* 392:25-30, Nature Pub. Co. (1998).
Arathoon, W.R., and Birch, J.R., "Large-Scale Cell Culture in Biotechnology," *Science* 232:1390-1395, American Association for the Advancement of Science (1986).
Bailey, J.E., "Toward a Science of Metabolic Engineering," *Science* 252:1668-1675, American Association for the Advancement of Science (1991).
Bailey, J.E. et al., "Engineering Glycosylation in Animal Cells," in *New Developments and New Applications in Animal Cell Technology*, Merten, O.W., et al., eds., Kluwer Academic Publishers, The Netherlands, pp. 5-23 (1998).
Bailey, J.E., et al., "Metabolic Engineering of N-Linked Glycoform Synthesis Systems in Chinese Hamster Ovary (CHO) Cells," in *Animal Cell Technology*, Carrondo, M.J.T., et al., eds. Kluwer Academic Publishers, The Netherlands, pp. 489-494 (1997).
Bibila, T.A., and Flickinger, M.C., "A Model of Interorganelle Monoclonal Antibody Transport and Secretion in Mouse Hybridoma Cells," *Biotechnol. Bioeng.* 38:767-780, John Wiley & Sons, Inc. (1991).
Bibila, T.A., and Robinson, D.K., "In Pursuit of the Optimal Fed-Batch Process for Monoclonal Antibody Production," *Biotechnol. Prog.* 11:1-13, American Chemical Society and American Institute of Chemical Engineers (1995).
Bitter, G.A., "Heterologous Gene Expression in Yeast," *Meth. Enzymol.* 152:673-684, Academic Press, Inc. (1987).

(Continued)

*Primary Examiner*—David Guzo
(74) *Attorney, Agent, or Firm*—Sterne Kessler Goldstein & Fox, PLLC

(57) ABSTRACT

The present invention relates to the field glycosylation engineering of proteins. More particular, the present invention is directed to the glycosylation engineering of proteins to provide proteins with improved therapeutic properties, e.g., antibodies, antibody fragments, or a fusion protein that includes a region equivalent to the Fc region of an immunoglobulin, with enhanced Fc-mediated cellular cytotoxicity.

67 Claims, 16 Drawing Sheets

OTHER PUBLICATIONS

Figure 1:
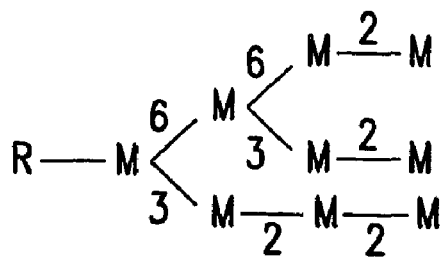
Figure 1:
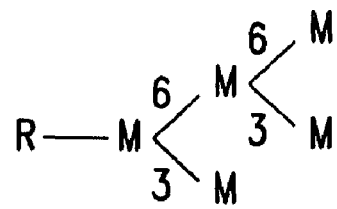
Figure 1:
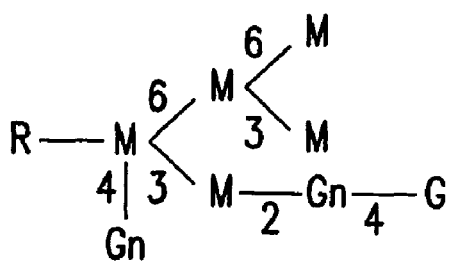
Figure 1:
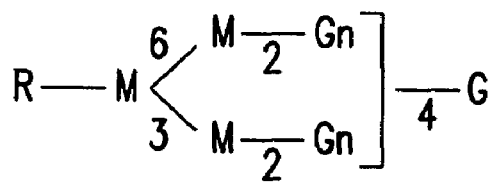
Figure 1:
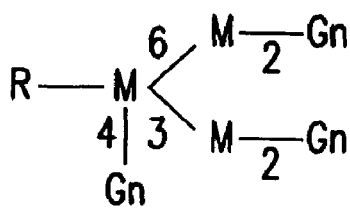
Figure 1:
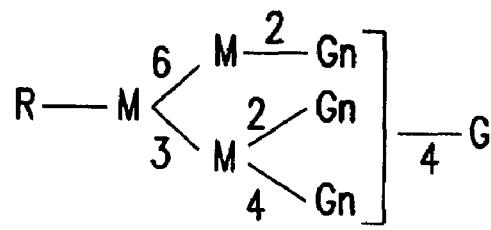
Figure 1:
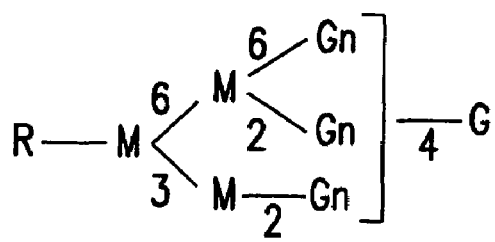
Figure 1:
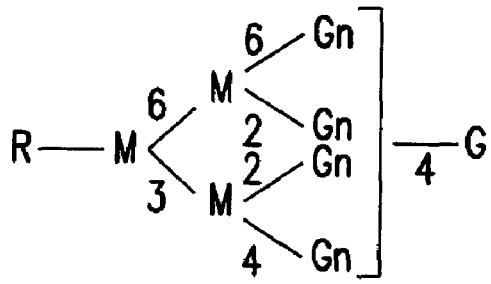

Bitter, G.A., et al., "Expression and Secretion Vectors for Yeast," *Meth. Enzymol.* 153:516-544, Academic Press, Inc. (1987).

Bretscher, M.S., and Munro, S., "Cholesterol and the Golgi Apparatus," *Science* 261:1280-1281, American Association for the Advancement of Science (1993).

Briles, E.B., et al., "Isolation of Wheat Germ Agglutinin-resistant Clones of Chinese Hamster Ovary Cells Deficient in Membrane Sialic Acid and Galactose," *J. Biol. Chem.* 252:1107-1116, American Society for Biochemistry and Molecular Biology, Inc. (1977).

Brisson, N., et al., "Expression of a bacterial gene in plants by using a viral vector," *Nature* 310:511-514, Nature Pub. Co. (1984).

Brockhausen, I., et al., "Control of glycoprotein synthesis. Characterization of (1 4)-$N$-acetyl-$\beta$-D-glucosaminyltransferases acting on the $\alpha$-D-(1 3)- and $\alpha$-D-(1 6)-linked arms of $N$-linked oligosaccharides," *Carbohydrate Res.* 236:281-299, Elsevier Science Publishers B.V. (1992).

Broglie, R., et al., "Light-Regulated Expression of a Pea Ribulose-1,5-Biphosphate Carboxylase Small Subunit Gene in Transformed Plant Cells," *Science* 224:838-843, American Association for the Advancement of Science (1984).

Campbell, C., and Stanlet, P., "A Dominant Mutation to Ricin Resistance in Chinese Hamster Ovary Cells Induces UDP-GlcNAc:Glycopeptide $\beta$-4-$N$-Acetylglucosaminyltransferase III Activity," *J. Biol. Chem.* 261:13370-13378, American Society for Biochemistry and Molecular Biology, Inc. (1984).

Caruthers, M.H., et al., "New chemical methods for synthesizing polynucleotides," *Nuc. Acids Res. Symp. Series* 7:215-223, IRL Press Limited (1980).

Chow, F., et al., "Synthesis of oligodeoxyribonucleotides on silica del support," *Nuc. Acids Res.* 9:2807-2817, IRL Press Limited (1981).

Cole, N.B., et al., "Diffusional Mobility of Golgi Proteins in Membranes of Living Cells," *Science* 273:797-801, American Association for the Advancement of Science (1996).

Cole, S.P.C., et al., "The EBV-Hybridoma Technique and its Application to Human Lung Cancer," in *Monoclonal Antibodies and Cancer Therapy*, Reisfeld, R.A., and Sell, S., eds., Alan R. Liss, Inc., New York, NY, pp. 77-96 (1985).

Coruzzi, G., et al., "Tissue-specific and light-regulated expression of a pea nuclear gene encoding the small subunit of ribulose-1,5-biphosphate carboxylase," *EMBO J.* 3:1671-1679, IRL Press Limited (1984).

Cote, R.J., et. al., "Generation of human monoclonal antibodies reactive with cellular antigens," *Proc. Natl. Acad. Sci.* 80:2026-2030, The National Academy of Sciences (1983).

Crea, R., and Horn, T., "Synthesis of oligonucleotides on cellulose by a phosphotriester method," *Nuc. Acids Res.* 8:2331-2348, IRL Press Limited (1980).

Creighton, T.E., *Proteins: Structures and Molecular Principles*, W.H. Freeman and Co., New York, NY, pp. 34-60 (1983).

Cumming, D.A., "Glycosylation of recombinant protein therapeutics: control and functional implications," *Glycobiology* 1:115-130, Oxford University Press (1991).

Dörr, U., et. al., "First Clinical Results with the Chimeric Antibody chCE7 and Neuroblastoma. Targeting Features and Biodistribution Data," *Eur. J. Nucl. Med.* 20:858, Springer International (1993).

Dennis, J.W., et. al., "$\beta$1-6 Branching of Asn-Linked Oligosaccharides Is Directly Associated with Metastasis," *Science* 236:582-585, American Association for the Advancement of Science (1987).

Do, K.-Y., "Modification of Glycoproteins by $N$-Acetylglucosaminyltransferase V Is Greatly Influenced by Accessibility of the Enzyme to Oligosaccharide Acceptors," *J. Biol. Chem.* 269:23456-23464, American Society for Biochemistry and Molecular Biology (1994).

Dunphy, W.G., and Rothman, J.E., "Compartmentation of Asparagine-linked Oligosaccharide Processing in the Golgi Apparatus," *J. Cell. Bio.* 97:270-275, Rockefeller University Press (1983).

Dunphy, W.G., et. al., "Attachment of Terminal N-Acetylglucosamine to Asparagine-Linked Oligosaccharide Occurs in Central Cistemae of the Golgi Stack," *Cell* 40:463-472, MIT (1985).

Dunphy, W.G., et. al., "Early and late functions associated with the Golgi apparatus reside in distinct compartments," *Proc. Natl. Acad. Sci.* 78:7453-7457, The National Academy of Sciences (1981).

Dwek, R.A., "Glycobiology: More Functions for Oligosaccharides," *Science* 269:1234-1235, American Association for the Advancement of Science (1995).

Easton, E.W., et. al., "Enzymatic Amplification Involving Glycosyltransferases Forms the Basis for the Increased Size of Asparagine-linked Glycans at the Surface of NIH 3T3 Cells Expressing the N-*ras* Proto-oncogene," *J. Biol. Chem.* 266:21674-21680, American Society for Biochemistry and Molecular Biology (1991).

Elices, M.J., and Goldstein, I.J., "Ehrlich Ascites Tumor Cell UDP-Gal:$N$-Acetyl-D-glucosamine $\beta$(1,4)-Galactosyltransferase," *J. Biol. Chem.* 263:3354-3362, American Society for Biochemistry and Molecular Biology, Inc. (1988).

Elion, E.A., "Enzymatic Manipulation of DNA and RNA," in *Current Protocols in Molecular Biology*, Ausubel, F., et. al., eds., John Wiley and Sons, New York, NY, pp. 3.17.1-3.17.10 (1998).

Fanger, M.W., et. al., "Cytotoxicity mediated by human Fc receptors for IgG," *Immunol. Today* 10:92-99 (1989).

Field, M., et. al., "The Use of High-Performance Anion-Exchange Chromatography and Matrix-Assisted Laser Desorption/Ionization Time-of-Flight Mass Spectrometry to Monitor and Identify Oligosaccharide Degradation," *Anal. Biochem.* 239:92-98, Academic Press, Inc. (1996).

Fouser, L.A., et. al., "High Level Expression of a Chimeric Anti-Ganglioside GD2 Antibody: Genomic Kappa Sequences Improve Expression in COS and CHO Cells," *Biotech.* 10:1121-1127, Nature Pub. Co. (1992).

Frost, J.D., et. al., "A Phase I/IB Trial of Murine Monoclonal Anti-GD2 Antibody 14.G2a plus Interleukin-2 in Children with Refractory Neuroblastoma," *Cancer* 80:317-333, American Cancer Society (1997).

Goldberg, D.E., and Kornfeld, S., "Evidence for Extensive Subcellular Organization of Asparagine-linked Oligosaccharide Processing and Lysosomal Enzyme Phosphorylation," *J. Biol. Chem.* 258:3159-3165, American Society for Biochemistry and Molecular Biology, Inc. (1983).

Goochee, C.F., et. al., "The Oligosaccharides of Glycoproteins: Factors Affecting their Synthesis and their Influence on Glycoprotein Properties," in *Frontiers in Bioprocessing II*, Todd, P., et. al., eds., American Chemical Society, Washington, DC, pp. 199-240 (1992).

Gossen, M., et. al., "Control of gene activity in higher eukaryotic cells by prokaryotic regulatory elements," *TIBTECH* 12:58-62, Elsevier Science Ltd. (1994).

Graham, R.A., et. al., "The polymorphic epithelial mucin: potential as an immunogen for a cancer vaccine," *Cancer Immunol. Immunother.* 42:71-80, Springer-Verlag (1996).

Grierson, D., and Covey, S.N., *Plant Molecular Biology, 2nd edition*, Blackie Publishing, London, GB, Chapters 7-9 (1988).

Griffiths, G., et. al., "The Dynamic Nature of the Golgi Complex," *J. Cell Bio.* 108 :277-297, Rockefeller University Press (1989).

Gross, H.J., et. al., "A Highly Sensitive Fluorometric Assay for Sialytransferase Activity Using CMP-9-fluoresceinyl-NeuAc as Donor," *Analyt. Biochem.* 186:127-134, Academic Press, Inc. (1990).

Gu, J., et. al., "Purification and Characterization of UDP-$N$-Acetylglucosamine: $\alpha$-6-D-Mannoside $\beta$1-6$N$-Acetylglucosaminyltransferase ($N$-Acetylglucosaminyltransferase V) from a Human Lung Cancer Cell Line," *J. Biochem.* 113:614-619, Tokyo Japanese Biochemical Society (1993).

Gurley, W.B., et. al., "Upstream Sequences Required for Efficient Expression of a Soybean Heat Shock Gene," *Mol. Cell. Bio.* 6:559-565, American Society for Microbiology (1986).

Haga, Y., et. al., "Dose-Related Comparison of Antibody-Dependent Cellular Cytotoxicity with Chimeric and Native Murine Monoclonal Antibody 17-1A," *Int. J. Pancreatol.* 15:43-50, Humana Press Inc. (1994).

Harpaz, N., and Schachter, H., "Control of Glycoprotein Synthesis," *J. Biol. Chem.* 255:4894-4902, American Society for Biochemistry and Molecular Biology, Inc. (1980).

Harvey, D.J., "Quantitative Aspects of the Matrix-assisted Laser Desorption Mass Spectrometry of Complex Oligosaccharides," *Rapid Commun. Mass Spectrom.* 7:614-619, John Wiley & Sons, Ltd. (1993).

Hirschberg, C.B., and Snider, M.D., "Topography of Glycosylation in the Rough Endoplasmic Reticulum and Golgi Apparatus," *Ann. Rev. Biochem.* 56:63-87, Annual Reviews Inc. (1987).

Huse, W.D., et. al., "Generation of a Large Combinatorial Library of the Immunoglobin Repertoire in Phage Lambda," *Science* 246:1275-1281, American Association for the Advancement of Science (1989).

Jefferis, R., et. al., "Recognition sites on human IgG for Fcγ receptors: the role of glycosylation," *Immunology Letters* 44:111-117, Elsevier Science B.V. (1995).

Jenkins, N., and Curling, E.M.A., "Glycosylation of recombinant proteins: Problems and prospects," *Enzyme Microb. Technol.* 16:354-364, Butterworth-Heinemann (1994).

Jenkins, N., et. al., "Getting the glycosylation right: Implications for the biotechnology industry," *Nat. Biotechnol.* 14:975-981, Nature Pub. Co. (1996).

Köhler, G., and Milstein, C., "Continuous cultures of fused cells secreting antibody of predefined specificity," *Nature* 256:495-497, Nature Pub. Co. (1975).

Kagawa, Y., et. al., "Comparative Study of the Asparagine-linked Sugar Chains of Natural Human Interferon-β1 and Recombinant Human Interferon-β1 Produced by Three Different Mammalian Cells," *J. Biol. Chem.* 263:17508-17515, American Society for Biochemistry and Molecular Biology, Inc. (1988).

Küster, B., et. al., "Sequencing of N-Linked Oligosaccharides Directly from Protein Gels: In-Gel Deglycosylation Followed by Matrix-Assisted Laser Desorption/Ionization Mass Spectrometry and Normal-Phase High-Performance Liquid Chromatography," *Analyt. Biochem.* 250:82-101, Academic Press (1997).

Koenig, A., "Selectin inhibition: synthesis and evaluation of novel sialylated, sulfated and fucosylated oligosaccharides, including the major capping group of GlyCAM-1," *Glycobiology* 7:79-93, Oxford University Press (1997).

Kolber, M.A., et. al., "Measurement of cytotoxicity by target cell release and retention of the fluorescent dye bis-carboxyethyl-carboxyfluorescein (BCECF)," *J. Immunol. Meth.* 108:255-264, Elsevier Science Publishers B.V. (1988).

Kornfeld, R., and Kornfeld, S., "Assembly of Asparagine-Linked Oligosaccharides," *Ann. Rev. Biochem.* 54:631-664, Annual Reviews Inc. (1985).

Kozbor, D., and Roder, J.C., "The production of monoclonal antibodies from human lymphocytes," *Immunol. Today* 4:72-79, Elsevier Biomedical Press (1983).

Lifely, M.R., et. al., "Glycosylation and biological activity of CAMPATH-1H expressed in different cell lines and grown under different culture conditions," *Glycobiology* 5:813-822, Oxford University Press (1995).

Lis, H., and Sharon, N., "Protein glycosylation: Structural and functional aspects," Eur. *J. Biochem.* 218:1-27, FEBS (1993).

Lloyd, K.O., et. al., "Comparison of O-Linked Carbohydrate Chains in MUC-1 Mucin from Normal Breast Epithelial Cell Lines and Breast Carcinoma Cell Lines," *J. Biol. Chem.* 271:33325-33334, American Society for Biochemistry and Molecular Biology, Inc. (1996).

Lund, J., et. al., "Control of IgG/Fc Glycosylation: A Comparison of Oligosaccharides from Chimeric Human/Mouse and Mouse Subclass Immunoglobulin Gs" *Molec. Immunol.* 30:741-748, Pergamon Press Ltd. (1993).

Lund, J., et. al., "Oligosaccharide-protein interactions in IgG can modulate recognition by Fcγ receptors," *Res. Commun.* 9:115-119, FASEB (1995).

Malhotra, R., et. al., "Glycosylation changes of IgG associated with rheumatoid arthritis can activate complement via the mannose-binding protein," *Nat. Med.* 1:237-243, Nature Pub. Co. (1995).

Marshall, E., "Gene therapy's growing pains," *Science* 269:1050-1055, American Association for the Advancement of Science (1995).

Matteucci, M.D., and Caruthers, M.H., "The Synthesis of Oligodeoxypyrimidines on a Polymer Support," *Tetrahedron Letters* 21:719-722, Pergamon Press Ltd. (1980).

Misaizu, T., et. al., "Role of Antennary Structure of N-Linked Sugar Chains in Renal Handling of Recombinant Human Erythropoietin," *Blood* 86:4097-4104, The American Society of Hematology (1995).

Moremen, K.W., et. al., "Glycosidases of the asparagine-linked oligosaccharide processing pathway," *Glycobiology* 4:113-125, Oxford University Press (1994).

Morgan, A., et. al., "The N-terminal end of the $C_H2$ domain of chimeric human IgG1 anti-HLA-DR is necessary for C1q, FcγRI and FcγRIII binding," *Immunol.* 86:319-324, Blackwell Science Ltd. (1995).

Morrison, S.L., et. al., "Chimeric human antibody molecules: Mouse antigen-binding domains with human constant region domains," *Proc. Natl. Acad. Sci.* 81:6851-6855, National Academy of Sciences (1984).

Narasimhan, S., "Control of Glycoprotein Synthesis," *J. Biol. Chem.* 257:10235-10242, American Society for Biochemistry and Molecular Biology, Inc. (1982).

Narasimhan, S., et. al., "Control of Glycoprotein Synthesis. Bovine Milk UDPgalactose: N-Acetylglucosamine β-4-Galactosyltransferase Catalyzes Preferential Transfer of Galactose to the GlcNAcβ1,2Manα1,3- Branch of both Bisected and Nonbisected Complex Bioantennary Asparagine-Linked Oligosaccharides," *Biochem.* 24:1694-1700, American Chemical Society (1985).

Naven, T.J.P., and Harvey, D.J., "Effect of Structure on the Signal Strength of Oligosaccharides in Matrix-assisted Laser Desorption/Ionization Mass Spectrometry on Time-of-flight and Magnetic Sector Instruments," *Rapid Commun. Mass Spectrom.* 10:1361-1366, John Wiley & Sons, Ltd. (1996).

Neuberger, M.S., et. al., "Recombinant antibodies possessing novel effector functions," *Nature* 312:604-608, Nature Pub. Co. (1984).

Nilsson, T., et. al., "Kin recognition between *medial* Golgi enzymes in HeLa cells," *EMBO J.* 13:562-574, Oxford University Press (1994).

Nilsson, T., et. al., "Overlapping Distribution of Two Glycotransferases in the Golgi Apparatus of HeLa Cells," *J. Cell Biol.* 120:5-13, Rockefeller University Press (1993).

Nilsson, T., et. al., "The role of the membrane-spanning domain and stalk region of N-acetylglucosaminyltransferase I in retention, kin recognition and structural maintenance of the Golgi apparatus in HeLa cells," *J. Cell Sci.* 109:1975-1989, The Company of Biologists Limited (1996).

Nishikawa, A., et. al., "Purification, cDNA Cloning, and Expression of UDP-N-acetylglucosamine:β-D-mannoside β-1,4N-Acetylglucosaminyltransferase III from Rat Kidney," *J. Biol. Chem.* 267:18199-18204, American Society for Biochemistry and Molecular Biology, Inc. (1992).

Ohno, M., et. al., "Enzymatic Basis of Sugar Structures of α-Fetoprotein in Hepatoma and Hepatoblastoma Cell Lines: Correlation with Activities of α1-6 Fucosyltransferase and N-Acetylglucosaminyltransferases III and V," *Int. J. Cancer* 51:315-317, Wiley-Liss, Inc. (1992).

Orkin, S.H, and Motulsky, A.G., "Report and recommendations of the panel to assess the NIH investment in research on gene therapy," Dec. 7, 1995, available at <http://www.nih.gov/news/panelrep.html>.

Påquet, M.R., et. al., "Branch Specificity of Purified Rat Liver Golgi UDP-galactose:N-Acetylglucosamine β-1,4-Galactosyltransferase," *J. Biol. Chem.* 259:4716-4721, American Society for Biochemistry and Molecular Biology, Inc. (1984).

Page, M.J., and Sydenham, M.A., "High Level Expression of the Humanized Monoclonal Antibody CAMPATH-1H in Chinese Hamster Ovary Cells," *Biotechnology* 9:64-68, Nature Pub. Co. (1991).

Palcic, M.M., et. al., "Regulation of N-Acetylglucosaminyltransferase V Activity," *J. Biol. Chem.* 265:6759-6769, American Society for Biochemistry and Molecular Biology, Inc. (1990).

Paulson, J.C., and Colley, K.J., "Glycosyltransferases," *J. Biol. Chem.* 264:17615-17618, American Society for Biochemistry and Molecular Biology, Inc. (1989).

Pels Rijcken, W.R., et. al., "The effect of increasing nucleotide-sugar concentrations on the incorporation of sugars into glycoconjugates in rat hepatocytes," *Biochem. J.* 305:865-870, UK Biochemical Society (1995).

Rabouille, C., et. al., "Mapping the distribution of Golgi enzymes involved in the construction of complex oligosaccharides," *J. Cell Sci.* 108:1617-1627, The Company of Biologists Limited (1995).

Rao, A.K., and Mendicino, J., "Influence of Glycopeptide Structure on the Regulation of Galactosyltransferase Activity," *Biochem.* 17:5632-5638, American Chemical Society (1978).

Rearick, J.I., et. al., "Enzymatic Characterization of β-Galactoside α2 3 Sialyltransferase from Porcine Submaxillary Gland," *J. Biol. Chem.* 254:4444-4451, American Society for Biochemistry and Molecular Biology, Inc. (1979).

Reff, M.E., et. al., "Depletion of B Cells In Vivo by a Chimeric Mouse Human Monoclonal Antibody to CD20," *Blood* 83:435-445, American Society of Hematology (1994).

Riechmann, L., et. al., "Reshaping human antibodies for therapy," *Nature* 332:323-327, Nature Pub. Co. (1988).

Robinson, R.R., et. al., "Chimeric mouse-human anti-carcinoma antibodies that mediate different anti-tumor cell biological activities," *Hum. Antibod. Hybridomas* 2:84-93, Butterworth-Heinemann (1991).

Rogers, S.G., et. al., "Gene Transfer in Plants: Production of Transformed Plants Using Ti Plasmid Vectors," in *Methods for Plant Molecular Biology*, Weissbach, A., and Weissbach, H., eds., Academic Press, Inc., San Diego, CA, pp. 423-463 (1988).

Roman, H., "Development of Yeast as an Experimental Organism," in *The Molecular Biology of the Yeast Saccharomyces, Life Cycle and Inheritance*, Strathern, J.N., et. al., eds., Cold Spring Harbor Laboratory Press, Cold Spring Harbor, NY, pp. 1-9 (1981).

Rothman, J.E., and Orci, L., "Molecular dissection of the secretory pathway," *Nature* 355:409-415, Nature Pub. Co. (1992).

Rothman, J.E., and Wieland, F.T., "Protein Sorting by Transport Vesicles," *Science* 272:227-234, American Association for the Advancement of Science (1996).

Rothstein, R., "Cloning in Yeast," in *DNA Cloning Column II: a practical approach*, Glover, D.M., ed., IRL Press, Washington, DC, pp. 45-66 (1985).

Russo, R.N., et. al., "β1,4-Galactosyltransferase: A Short $NH_2$-terminal Fragment That Includes the Cytoplasmic and Transmembrane Domain Is Sufficient for Golgi Retention," *J. Biol. Chem.* 267:9241-9247, American Society for Biochemistry and Molecular Biology, Inc. (1992).

Sambanis, A., et. al., "A Model of Secretory Protein Trafficking in Recombinant AtT-20 Cells," *Biotech. And Biotechnol. Bioeng.* 38:280-295, John Wiley & Sons, Inc. (1991).

Sambrook, J., et. al., *Molecular Cloning, A Laboratory Manual, 2nd Edition*, Cold Spring Harbor Laboratory Press, Cold Spring Harbor, NY, pp. 8.1-9.62 (1989).

Sburlati, A., et. al., "Novel glycoform of recombinant human IFN-β by overexpression of *N*-acetyl glucosaminyltransferase II," *Glycoconj. J.* 14:781, Kluwer Academic Publishing (1997).

Sburlati, A.R., et. al., "Synthesis of Bisected Glycoforms of Recombinant IFN-β by Overexpression of β-1,4-*N*-Acetylglucosaminyltransferase III in Chinese Hamster Ovary Cells," *Biotechnol. Prog.* 14:189-192, American Chemical Society (Mar.-Apr. 1998).

Schachter, H., "Biosynthetic controls that determine the branching and microheterogenicity of protein-bound oligosaccharides," *Biochem. Cell. Biol.* 64:163-181, National Research Council of Canada (1986).

Shao, M-C., and Wold, F., "The Effect of the Protein Matrix on Glycan Processing in Glycoproteins," *J. Biol. Chem.* 263:5771-5774, American Society for Biochemistry and Molecular Biology, Inc. (1988).

Shao, M-C., and Wold, F., "The effect of the protein matrix proximity on glycan reactivity in a glycoprotein model," *Eur. J. Biochem.* 228:79-85, FEBS (1995).

Sheares, B.T., Robbins, P.W., "Glycosylation of ovalbumin in a heterologous cell: Analysis of oligosaccharide chains of the cloned glycoprotein in mouse L cells," *Proc. Natl. Acad. Sci.* 83:1993-1997, National Academy of Sciences (1986).

Shelikoff, M., et. al., "A Modeling Framework for the Study of Protein Glycosylation," *Biotechnol. Bioeng.* 50:73-90, John Wiley & Sons, Inc. (1996).

Smith, G.E., et. al., "Molecular Engineering of the *Autographa californica* Nuclear Polyhedrosis Virus Genome: Deletion Mutations Within the Polyhedrin Gene," *J. Virol.* 46:584-593, American Society for Microbiology (1983).

Spellman, M.W., et. al., "Carbohydrate Structures of Human Tissue Plasminogen Activator Expressed in Chinese Hamster Ovary Cells," *J. Biol. Chem.* 264:14100-14111, American Society for Biochemistry and Molecular Biology, Inc. (1989).

Struhl, K., "Subcloning of DNA Fragments," in *Current Protocols in Molecular Biology*, Ausubel, F., et. al., eds., John Wiley and Sons, New York, NY, pp. 3.16.1-3.16.11 (1998).

Surfus, J.E., et. al., "Anti-Renal-Cell Carcinoma Chimeric Antibody G250 Facilitates Antibody-Dependent Cellular Cytotoxicity with In Vitro and In Vivo Interleukin-2-Activated Effectors," *J. Immunother. Emphasis Tumor Immunol.* 19:184-191, Lippincott-Raven Publishers (1996).

Tabas, I., and Kornfeld, S., "Purification and Characterization of a Rat Liver Golgi α-Mannosidase Capable of Processing Asparagine-linked Oligosaccharides," *J. Biol. Chem.* 254:11655-11663, American Society for Biochemistry and Molecular Biology, Inc. (1979).

Takamatsu, N., et. al., "Expression of bacterial chloramphenicol acetyltransferase gene in tobacco plants mediated by TMV-RNA," *EMBO J.* 6:307-311, IRL Press Limited (1987).

Takeda, S-i. et. al., "Construction of chimaeric processed immunoglobulin genes containing mouse variable and human constant region sequences," *Nature* 314:452-454, Nature Pub. Co. (1985).

Tanemura, M., et. al., "Reduction of the Major Swine Xenoantigen GALα(1,3)GAL by Transfection of N-Acetylglucosaminyl Transferase III (GnT-III) Gene," *Transplantation Proceedings* 29:891-892 (1997).

Taniguchi, N., et. al., "Glycosyltransferase Assays Using Pyridylaminated Acceptors: *N*-Acetylglucosaminyltransferase III, IV, and V," *Meth. Enzymol.* 179:397-408, Academic Press, Inc. (1989).

Trill, J.J., et. al., "Production of monoclonal antibodies in COS and CHO cells," *Curr. Opin. Biotechnol.* 6:553-560, Current Biology Ltd. (1995).

Umaña, P., et. al., "Engineered glycoforms of an antineuroblastoma IgG1 with optimized antibody-dependent cellular cytotoxic activity," *Nat. Biotechnol.* 17:176-180, Nature Pub. Co. (1999).

Varki, A., "Biological roles of oligosaccharides: all of the theories are correct," *Glycobiology* 3:97-130, Oxford University Press (1993).

Velasco, A., et. al., "Cell Type-dependent Variations in the Subcellular Distribution of α-Mannosidase I and II," *J. Cell. Biol.* 122:39-51, Rockefeller University Press (1993).

Verma, I.M., et. al., "Gene therapy—promises, problems and prospects," *Nature* 389:239-242, Nature Pub. Co. (1997).

Watson, E., et. al., "Structure determination of the intact major sialylated oligosaccharide chains of recombinant human erythropoietin expressed in Chinese hamster ovary cells," *Glycobiology* 4:227-237, Oxford University Press (1994).

Wiest, D.L., et. al., "Membrane Biogenesis during B Cell Differentiation: Most Endoplasmic Reticulum Proteins are Expressed Coordinately," *J. Cell. Biol.* 110:1501-1511, Rockefeller University Press (1990).

Wright, A., and Morrison, S.L., "Effect of glycosylation on antibody function: implications for genetic engineering," *TIBTECH* 15:26-31, Elsevier Science Ltd. (1997).

Wyss, D.F., and Wagner, G., "The structural role of sugars in glycoproteins," *Curr. Opin. Biotechnol.* 7:409-416, Current Biology Ltd. (1996).

Yamaguchi, N., and Fukuda, M.N., "Golgi Retention Mechanism of β-1,4-Galactosyltransferase," *J. Biol. Chem.* 270:12170-12176, American Society for Biochemistry and Molecular Biology, Inc. (1995).

Yoshimura, M., et. al., "Suppression of lung metastasis of B16 mouse melanoma by *N*-acetylglucosaminyltransferase III gene transfection," *Proc. Natl. Acad. Sci.* 92:8754-8758, National Academy of Sciences (1995).

Yu Ip, C.C., et. al., "Structural Characterization of the *N*-Glycans of a Humanized Anti-CD18 Murine Immunoglobulin G," *Arch. Biochem. Biophys.* 308:387-399, Academic Press, Inc. (1994).

Co-pending U.S. Appl. No. 10/633,699, inventors Umaña et al., filed Aug. 5, 2003 (Not Published).

English language abstract of Japanese Patent No. JP 09084582 A, Derwent WPI Accession No. 1997-253000 (Mar. 1997).

English language abstract of German Patent No. DE 19546680 A1, Derwent WPI Accession No. 1997-321072 (Jun. 1997).

English language abstract of International Patent Publication No. WO 00/52135 A2, Derwent WPI Accession No. 2000-572178 (Sep. 2000).

English language abstract of International Patent Publication No. WO 00/53730 A2, Derwent WPI Accession No. 2000-594316 (Sep. 2000).

English language abstract of International Patent Publication No. WO 01/29242 A2, Derwent WPI Accession No. 2001-290925 (Apr. 2001).

English language abstract of European Patent Publication No. 585 083 A1, Derwent WPI Accession No. 1994-067563 (1994).

English language abstract of International Patent Publication No. WO 94/12646 A1, Derwent WPI Accession No. 1994-200274 (1994).

English language abstract of European Patent Publication No. 481 790 A, Derwent WPI Accession No. 1992-134048 (1992).

English language abstract of International Patent Publication No. WO 95/15769 A1, Derwent WPI Accession No. 1995-224151 (1995).

English language abstract of International Patent Publication No. WO 97/34632 A1, Derwent WPI Accession No. 1997-479995 (Sep. 1997).

English language abstract of U.S. Appl. No. 5,714,350 A, Derwent WPI Accession No. 1998-129858 (Feb. 1998).

English language abstract of International Patent Publication No. WO 98/49198 A1, Derwent WPI Accession No. 1998-080758 [07] (Nov. 1998).

English language abstract of International Patent Publication No. WO 96/13516 A1, Derwent WPI Accession No. 1996-239446 (1996).

English language abstract of International Patent Publication No. WO 98/58964 A1, Derwent WPI Accession No. 1999-081223 (Dec. 1998).

Edge, C.J., et al., "The conformational effects of N-linked glycosylation," *Biochem. Soc. Trans.* 21:452-455, Portland Press (1993).

Jefferis, R. and Lund, J., "Glycosylation of Antibody Molecules: Structural and Functional Significance," *Chem. Immunol.* 65:111-128, Karger (Jan. 1997).

Jefferis, R., et al., "Effector mechanisms activated by human IgG subclass antibodies: clinical and molecular aspects," *Ann. Biol. Clin..* 52:57-65, John Libbey Eurotext (1994).

Jefferis, R., et al., "IgG-Fc-mediated effector functions: molecular definition of interaction sites for effector ligands and the role of glycosylation," *Immunol. Rev.* 163:59-76, Munksgaard (Jun. 1998).

Nakamura, K., et al., "Chimeric Anti-Ganglioside $G_{M2}$ Antibody with Antitumor Activity," *Cancer Research* 54:1511-1516, American Association for Cancer Research (1994).

Rothman, R.J., et al., "Antibody-Dependent Cytotoxicity Mediated by Natural Killer Cells Is Enhanced by Castanospermine-Induced Alterations of IgG Glycosylation," *Mol. Immunol.* 26:1113-1123, Pergamon Press (1989).

Rothman R.J., et al., "Clonal Analysis of the Glycosylation of Immunoglobulin G Secreted by Murine Hybridomas," *Biochemistry* 28: 1377-1384, American Chemical Society (1989).

Routier, F.H., et al., "The glycosylation pattern of a humanized IgG1 antibody (D1.3) expressed in CHO cells," *Glycoconjugate J.* 14:201-207, Chapman & Hall (Feb. 1997).

Shitara, K., et al., "A new vector for the high level expression of chimeric antibodies in myeloma cells," *J. Immunol. Methods* 167:271-278, Elsevier Science (1991).

Standley, S. and Baudry, M., "The role of glycosylation in ionotropic glutamate receptor ligand binding, function, and trafficking," *Cell. Mol. Life Sci.* 57:1508-1516, Birkhäuser Verlag (Oct. 2000).

Standley, P., et al., "CHO cells provide access to novel N-gylcans and developmentally regulated glycosyltransferases," *Glycobiol.* 6:695-699, Oxford University Press (1996).

Youakim, A. and Shur, B.D., "Alteration of Oligosaccharide Biosynthesis by Genetic Manipulation of Glycosyltransferases," *Ann. N.Y. Acad. Sci.* 745:331-335, New York Academy of Sciences (1994).

Wright, A., and Morrison, S.L., "Effect of Altered $C_H2$-associated Carbohydrate Structure on the Functional Properties and In Vivo Fate of Chimeric Mouse-Human Immunoglobulin G1," *J. Exp. Med.* 180:1087-1096, The Rockefeller University Press (Sep. 1994).

Boyd, P.N., et al., "The Effect of the Removal of Sialic Acid, Galactose and Total Carbohydrate on the Functional Activity of Campath-1H," *Molec. Immunol.* 32:1311-1318, Pergamon Press (1995).

Davies, J. et al., "Expression of GnTIII in a Recombinant Anti-CD20 Production Cell Line: Expression of Antibodies with Altered Glycoforms Leads to an Increase in ADCC Through Higher Affinity for FcγRIII," *Biotechnol. Bioeng.* 74:288-294, John Wiley & Sons, Inc. (Aug. 2001).

De Bree, R., et al., "Clinical screening of monoclonal antibodies 323/A3, cSF-25 and K928 for suitability of targetting tumours in the upper aerodigestive and respiratory tract," *Nucl. Med. Commun.* 15:613-627, Lippincott, WIlliams & Wilkins (1994).

Dürrbach, A., et al., "Antibody-mediated endocytosis of G250 tumor-associated antigen allows targeted gene transfer to human renal cell carcinoma in vitro," *Cancer Gene Ther.* 6:564-571, Nature Publishing Group (Nov.-Dec. 1999).

Fukuta, K., et al., "Control of Bisecting GlcNAc Addition to N-Linked Sugar Chains," *J. Biol. Chem.* 275:23456-23461, The American Society for Biochemistry and Molecular Biology, Inc. (Aug. 2000).

Kaszubowski, P.A., et al., "A Cytotoxic Monoclonal Antibody to Colon Adenocarcinoma," *Cancer Res.* 44:1194-1197, American Association for Cancer Research (1984).

Kilmartin, J.V., et al., "Rat Monoclonal Antitubulin Antibodies Derived by Using a New Nonsecreting Rat Cell Line," *J. Cell Biol.* 93:576-582, The Rockefeller University Press (1982).

Luiten, R.M., et al., "Chimeric immunoglobulin E reactive with tumor-associated antigen activates human FcεRI bearing cells," *Hum. Antibodies* 8:169-180, IOS Press (Dec. 1997).

Lund, J., "Multiple Interactions of IgG with Its Core Oligosaccharide Can Modulate Recognition by Complement and Human Fcγ Receptor I and Influence the Synthesis of Its Oligosaccharide Chains," *J. Immunol.* 157:4963-4949, The American Association of Immunologists (1996).

Murakami, H., et al., "Human-Human Hybridomas Secreting Antibodies Specific to Human Lung Carcinoma," *In Vitro Cell. Develop. Biol.* 21:593-596, Tissue Culture Association, Inc. (1985).

Raju, T.S., et al., "Species-specific variation in glycosylation of IgG: evidence for the species-specific sialylation and branch-specific galactosylation and importance for engineering recombinant glycoprotein therapeutics," *Glycobiol.* 10: 477-486, IRL Press at Oxford University Press (May 2000).

Sheng, Y., et al., "Remodeling of Glycoconjugates on CD44 Enhances Cell Adhesion to Hyaluronate, Tumor Growth and Metastasis in B16 Melanoma Cells Expressing β1, 4-N-Acetylglucosaminyltransferase III," *Int. J. Cancer* 73:850-858, Wiley-Liss, Inc. (Dec. 1997).

Shields, R.L., et al., "Lack of Fucose on Human IgG1 N-Linked Oligosaccharide Improves Binding to Human FcγRIII and Antibody-dependent Cellular Toxicity," *J. Biol. Chem.* 277:26733-26740, The American Society for Biochemistry and Molecular Biology, Inc. (electronically available May 2002).

Surfus, J.E., et al., "Anti-Renal-Cell Carcinoma Chimeric Antibody G250 Facilitates Antibody-Dependent Cellular Cytotoxicity with In Vitro and In Vivo Interleukin-2-Activated Effectors," *J. Immunother.* 19:184-191, Raven Press (1996).

Umaā, P., et al., "Tetracycline-Regulated Overexpression of Glycosyltransferases in Chinese Hamster Ovary Cells," *Biotechnol. Bioeng.* 65:542-549, John Wiley & Sons, Inc. (Dec. 1999).

Valone, F.H., et al., "Phase Ia/Ib Trial of Bispecific Antibody MDX-210 in Patients with Advanced Breast or Ovarian Cancer That Overexpresses the Proto-Oncogene HER-2/neu," *J. Clin. Oncol.* 13:2281-2292, American Society for Clinical Oncology (1995).

Wright, A. and Morrison, S.L., "Effect of glycosylation on antibody function: implications for genetic engineering," *Trends Biotechnol.* 15:26-32, Elsevier Science Publishers (Jan. 1997).

Supplementary European Search Report for European Application No. 99 91 8731, mailed Dec. 17, 2004, European Patent Office, The Hague.

Office Action for U.S. Appl. No. 10/437,388, Umana et al., filed May 14, 2003, mailed on Oct. 26, 2006.

Office Action for U.S. Appl. No. 10/437,388, Umana et al., filed May 14, 2003, mailed on Jul. 25, 2007.

Office Action for U.S. Appl. No. 10/633,699, Umana et al., filed Aug. 5, 2003, mailed on Apr. 12, 2005.

Office Action for U.S. Appl. No. 10/633,699, Umana et al., filed Aug. 5, 2003, mailed on Mar. 23, 2006.

Office Action for U.S. Appl. No. 10/633,699, Umana et al., filed Aug. 5, 2003, mailed on Oct. 31, 2003.

Office Action for co-pending U.S. Appl. No. 10/437,388, Umana et al., filed May 14, 2003, mailed on Jan. 24, 2008.

Office Action for co-pending U.S. Appl. No. 10/633,699, Umana et al., filed Aug. 5, 2003, mailed on Nov. 15, 2007.

Office Action for U.S. Appl. No. 10/211,554, Umana et al., filed Aug. 5, 2002, mailed on Feb. 9, 2005.

Office Action for U.S. Appl. No. 11/199,232, Umana et al., filed Aug. 9, 2005, mailed on Mar. 17, 2008.

Buske, C., et al., "Monoclonal Antibody Therapy for B Cell Non-Hodgkin's Lymphomas: Emerging Concepts of a Tumor-targeted Strategy," *European Journal of Cancer* 35:549-557, Elsevier Science Ltd. (1999).

Maloney, D.G. et al., "Phase I Clinical Trial Using Escalating Single-Dose Infusion of Chimeric Anti-CD20 Monoclonal Antibody (IDEC-C2B8) in Patients With Recurrent B-Cell Lymphoma," *Blood* 84:2457-2466, The American Society of Hematology (1994).

Novak-Hofer, I., et al., "Cellular Processing of Copper-67-labeled Monoclonal Antibody chCE7 by Human Neuroblastoma Cells," *Cancer Research* 55:46-50, The American Association for Cancer Research (1995).

Office Action for co-pending U.S. Appl. No. 10/437,388, Umana et al., filed May 14, 2003, mailed date of Dec. 10, 2008.

\* cited by examiner

M9. HIGH-MANNOSE

M5. HIGH-MANNOSE

M5GnGn^b G. BISECTED HYBRID

M3Gn2G. BI-ANTENNARY COMPLEX

M3Gn2Gn^b. BISECTED
BI-ANTENNARY COMPLEX

M3Gn2G. TRI-ANTENNARY COMPLEX

M3Gn3'G. TRI'-ANTENNARY
COMPLEX

M3Gn4G. TETRA-ANTENNARY
COMPLEX

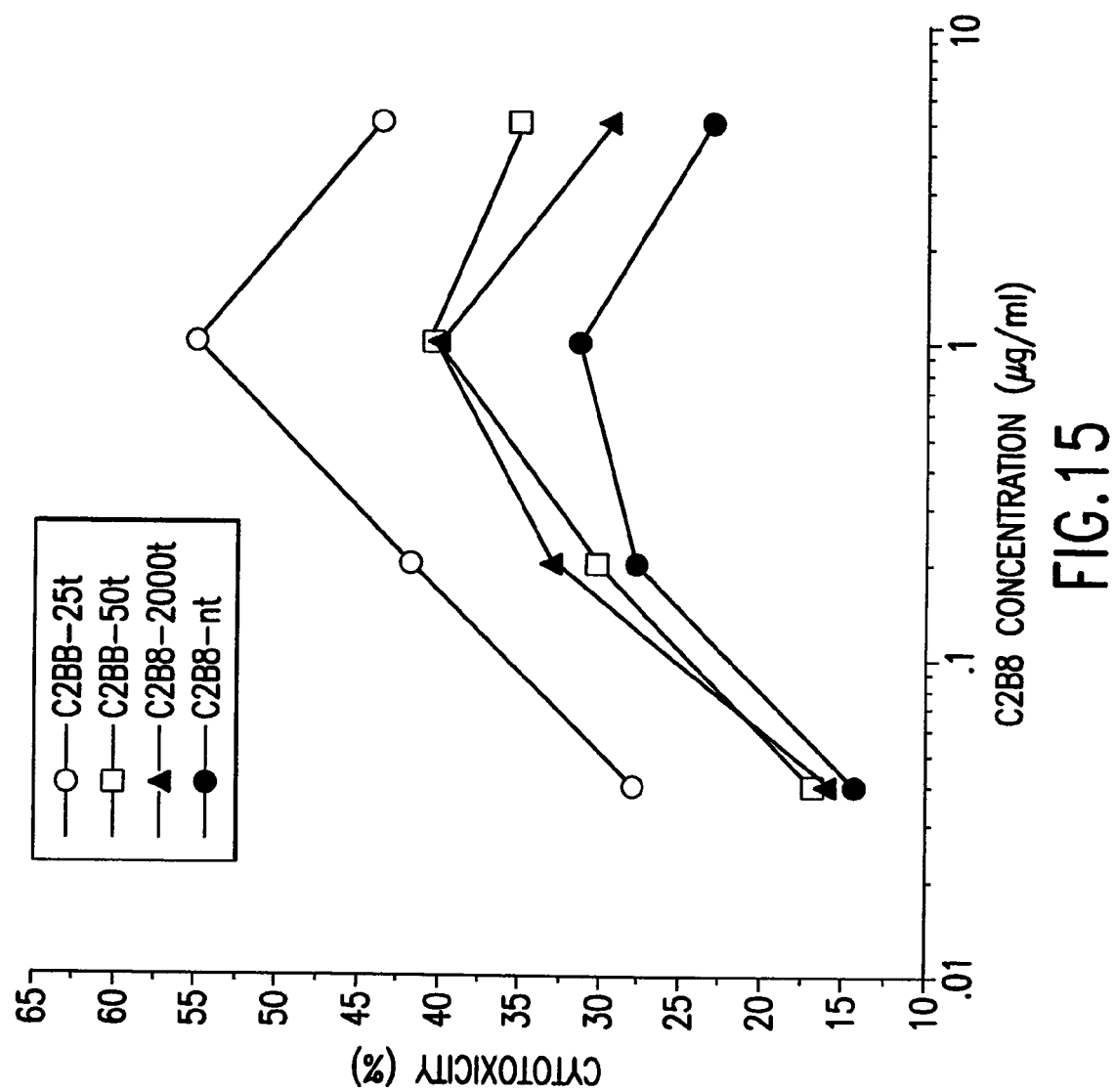

SEQUENCE LISTING

<160> NUMBER OF SEQ ID NOS: 14

<210> SEQ ID NO 1
<211> LENGTH: 50
<212> TYPE: DNA
<213> ORGANISM: Artificial
<220> FEATURE:
<223> OTHER INFORMATION: PCR Oligonucleotide Primer CE7VHPCR1.fwd

<400> SEQUENCE: 1
ttccttgtcg ctgttgctac gcgtgtcctg tcccaggtcc aactgcagca                50

<210> SEQ ID NO 2
<211> LENGTH: 63
<212> TYPE: DNA
<213> ORGANISM: Artificial
<220> FEATURE:
<223> OTHER INFORMATION: PCR Oligonucleotide Primer CE7VHPCR2.fwd

<400> SEQUENCE: 2
gtgtgttaag cttccaccat gggttggagc ctcatcttgc tcttccttgt cgctgttgct    60
acg                                                                  63

<210> SEQ ID NO 3
<211> LENGTH: 38
<212> TYPE: DNA
<213> ORGANISM: Artificial
<220> FEATURE:
<223> OTHER INFORMATION: PCR Oligonucleotide Primer CE7VHPCR(1+2).rev

<400> SEQUENCE: 3
gtgtgtgaat tcgctagctg aggagactgt gagagtgg                             38

<210> SEQ ID NO 4
<211> LENGTH: 40
<212> TYPE: DNA
<213> ORGANISM: Artificial
<220> FEATURE:
<223> OTHER INFORMATION: PCR Oligonucleotide Primer hGamma1CH1.fwd

<400> SEQUENCE: 4
gtttgtaagc ttgctagcac caagggccca tcggtcttcc                          40

<210> SEQ ID NO 5
<211> LENGTH: 59
<212> TYPE: DNA
<213> ORGANISM: Artificial
<220> FEATURE:
<223> OTHER INFORMATION: PCR Oligonucleotide Primer hGamma1CH1.rev

<400> SEQUENCE: 5
ggcatgtgtg agttttgtca caagatttgg gctcaacttt cttgtccacc ttggtgttg     59

<210> SEQ ID NO 6
<211> LENGTH: 57
<212> TYPE: DNA
<213> ORGANISM: Artificial
<220> FEATURE:
<223> OTHER INFORMATION: PCR Oligonucleotide Primer hGamma1CH2.fwd

<400> SEQUENCE: 6
tcttgtgaca aaactcacac atgcccaccg tgcccagacc tgaactcctg gggggac       57

<210> SEQ ID NO 7
<211> LENGTH: 49
<212> TYPE: DNA
<213> ORGANISM: Artificial
<220> FEATURE:
<223> OTHER INFORMATION: hGamma1CH2.rev

<400> SEQUENCE: 7
cctgtggttc tcggggctgc cctttggctt tggagatggt tttctcgat                49

```
<210> SEQ ID NO 8
<211> LENGTH: 22
<212> TYPE: DNA
<213> ORGANISM: Artificial
<220> FEATURE:
<223> OTHER INFORMATION: PCR Oligonucleotide Primer hGamma1CH3.fwd

<400> SEQUENCE: 8
gggcagcccc gagaaccaca gg                                          22

<210> SEQ ID NO 9
<211> LENGTH: 36
<212> TYPE: DNA
<213> ORGANISM: Artificial
<220> FEATURE:
<223> OTHER INFORMATION: PCR Oligonucleotide Primer hGamma1CH2.rev

<400> SEQUENCE: 9
gtgtgtggat cctcatttac ccggagacag ggagag                           36

<210> SEQ ID NO 10
<211> LENGTH: 56
<212> TYPE: DNA
<213> ORGANISM: Artificial
<220> FEATURE:
<223> OTHER INFORMATION: PCR Oligonucleotide Primer CE7VLPCR1.fwd

<400> SEQUENCE: 10
tgggtactgc tgctctgggt tccaggttcc actggtgaca tccagatgac acaatc     56

<210> SEQ ID NO 11
<211> LENGTH: 63
<212> TYPE: DNA
<213> ORGANISM: Artificial
<220> FEATURE:
<223> OTHER INFORMATION: PCR Oligonucleotide Primer CE7VLPCR2.fwd

<400> SEQUENCE: 11
gtgtgtaagc ttccaccatg gagacagaca cactcctgct atgggtactg ctgctctggg 60
ttc                                                               63

<210> SEQ ID NO 12
<211> LENGTH: 37
<212> TYPE: DNA
<213> ORGANISM: Artificial
<220> FEATURE:
<223> OTHER INFORMATION: PCR Oligonucleotide Primer CE7VLPCR(1+2).rev

<400> SEQUENCE: 12
gtgtgtgaat ccgtacgtt ttatttccaa ctctgtc                           37

<210> SEQ ID NO 13
<211> LENGTH: 32
<212> TYPE: DNA
<213> ORGANISM: Artificial
<220> FEATURE:
<223> OTHER INFORMATION: PCR Oligonucleotide Primer hKappa.fwd

<400> SEQUENCE: 13
gtgtgtaagc ttcgtacggt ggctgcacca tc                               32

<210> SEQ ID NO 14
<211> LENGTH: 33
<212> TYPE: DNA
<213> ORGANISM: Artificial
<220> FEATURE:
```

-continued

<223> OTHER INFORMATION: PCR Oligonucleotide Primer hKappa.rev

<400> SEQUENCE: 14
gtgtgtggat ccctaacact ctcccctgtt gaa   33

GLYCOSYLATION ENGINEERING OF ANTIBODIES FOR IMPROVING ANTIBODY-DEPENDENT CELLULAR CYTOTOXICITY

I. RELATION TO OTHER APPLICATIONS

This application is a division of U.S. application Ser. No. 09/294,584, filed Apr. 20, 1999 now U.S. Pat. No. 6,602,684, which claims the benefit of U.S. Provisional Application No. 60/082,581, filed Apr. 20, 1998, the entire contents of each of which are hereby incorporated by reference in their entirety.

II. FIELD OF THE INVENTION

The present invention relates to the field of glycosylation engineering of proteins. More particularly, the present invention relates to glycosylation engineering to generate proteins with improved therapeutic properties, including antibodies with enhanced antibody-dependent cellular cytotoxicity.

III. BACKGROUND OF THE INVENTION

Glycoproteins mediate many essential functions in human beings, other eukaryotic organisms, and some prokaryotes, including catalysis, signalling, cell-cell communication, and molecular recognition and association. They make up the majority of non-cytosolic proteins in eukaryotic organisms. Lis and Sharon, 1993, *Eur. J. Biochem.* 218:1-27. Many glycoproteins have been exploited for therapeutic purposes, and during the last two decades, recombinant versions of naturally-occurring, secreted glycoproteins have been a major product of the biotechnology industry. Examples include erythropoietin (EPO), therapeutic monoclonal antibodies (therapeutic mAbs), tissue plasminogen activator (tPA), interferon-β, (IFN-β), granulocyte-macrophage colony stimulating factor (GM-CSF), and human chorionic gonadotrophin (hCH). Cumming et al., 1991, *Glycobiology* 1:15-130.

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. Jenkins et al., 1996, *Nature Biotechn.* 14:975-981.

Mammalian cells are the preferred hosts for production of therapeutic glycoproteins, due to their capability to glycosylate proteins in the most compatible form for human application. Cumming, 1991, supra; Jenkins et al., 1996, supra. Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NS0- and SP2/0-mouse myeloma cells. More recently, production from transgenic animals has also been tested. Jenkins et al., 1996, supra.

The glycosylation of recombinant therapeutic proteins produced in animal cells can be engineered by overexpression of glycosyl transferase genes in host cells. Bailey, 1991, *Science* 252:1668-1675. However, previous work in this field has only used constitutive expression of the glycoprotein-modifying glycosyl transferase genes, and little attention has been paid to the expression level.

IV. SUMMARY OF THE INVENTION

The present invention is directed, generally, to host cells and methods for the generation of proteins having an altered glycosylation pattern resulting in improved therapeutic values. In one specific embodiment, the invention is directed to host cells that have been engineered such that they are capable of expressing a preferred range of a glycoprotein-modifying glycosyl transferase activity which increases complex N-linked oligosaccharides carrying bisecting GlcNAc. In other embodiments, the present invention is directed to methods for the generation of modified glycoforms of glycoproteins, for example antibodies, including whole antibody molecules, antibody fragments, or fusion proteins that include a region equivalent to the Fc region of an immunoglobulin, having an enhanced Fc-mediated cellular cytotoxicity, and glycoproteins so generated. The invention is based, in part, on the inventors' discovery that there is an optimal range of glycoprotein-modifying glycosyl transferase expression for the maximization of complex N-linked oligosaccharides carrying bisecting GlcNAc.

More specifically, the present invention is directed to a method for producing altered glycoforms of proteins having improved therapeutic values, e.g., an antibody which has an enhanced antibody dependent cellular cytotoxicity (ADCC), in a host cell. The invention provides host cells which harbor a nucleic acid encoding the protein of interest, e.g., an antibody, and at least one nucleic acid encoding a glycoprotein-modifying glycosyl transferase. Further, the present invention provides methods and protocols of culturing such host cells under conditions which permit the expression of said protein of interest, e.g., the antibody having enhanced antibody dependent cellular cytotoxicity. Further, methods for isolating the so generated protein having an altered glycosylation pattern, e.g., the antibody with enhanced antibody dependent cellular cytotoxicity, are described.

Furthermore, the present invention provides alternative glycoforms of proteins having improved therapeutic properties. The proteins of the invention include antibodies with an enhanced antibody-dependent cellular cytotoxicity (ADCC), which have been generated using the disclosed methods and host cells.

V. BRIEF DESCRIPTION OF THE DRAWINGS

FIG. 1 depicts the representation of typical oligosaccharide structures.

Figure 2:
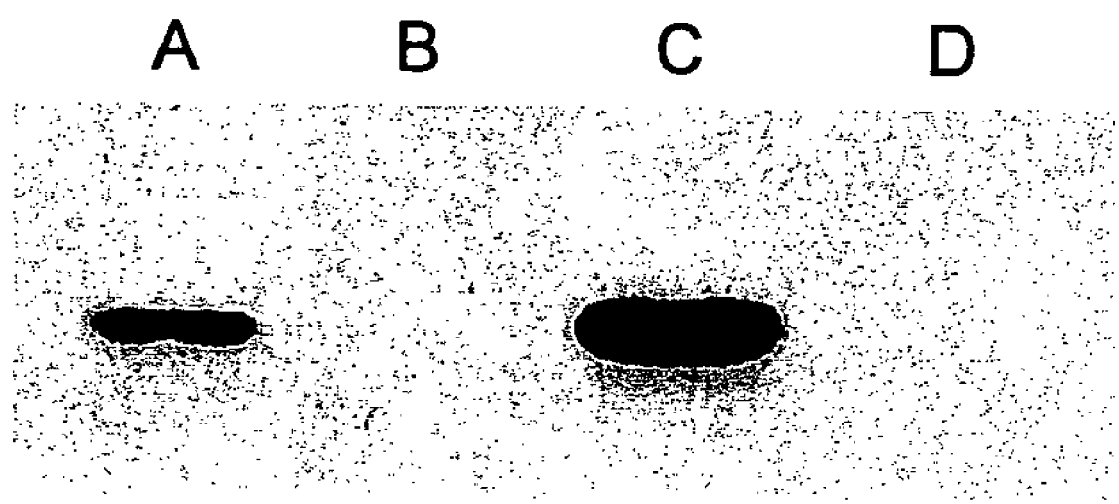

FIG. 2 depicts a Western blot analysis of tetracycline-regulated expression of GnT III in two different tTA-producing CHO clones. CHOt2 (lanes A and B) and CHOt17 (lanes C and D) cells were transfected with the pUDH10-3GnTIIIm expression vector and cultured for 36 h in the absence (lanes A and C) or presence of tetracycline, at a concentration of 400 ng/ml (lanes B and D). Cell lysates were then prepared for western blot analysis probing with an antibody (9E 10), which recognizes specifically the c-myc tag added to GnT III at its carboxy-terminus.

Figure 3:
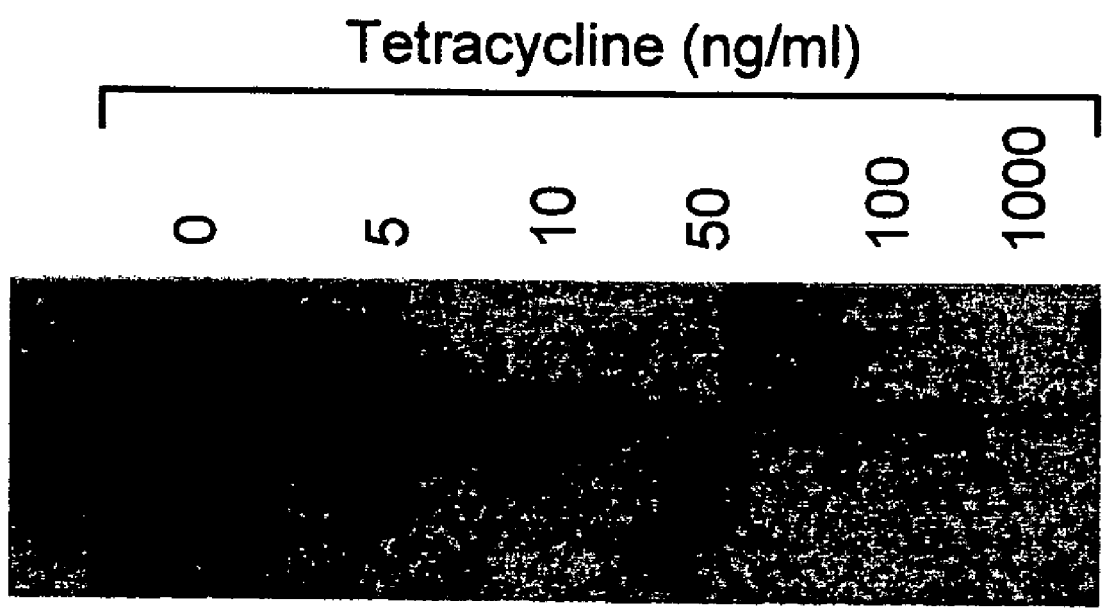

FIG. 3 depicts determination of the range of tetracycline concentrations where myc-tagged GnT III expression can be controlled. CHOt17 cells were transfected with the pUDH10-3-GnTIIIm expression vector and then cultured for 48 h in the presence of the indicated concentrations of tetracycline. GnT III levels in cell lysates from these cultures were compared using western blot analysis. GnT III was detected via the c-myc tag using 9E10 antibody.

Figure 4A:
Figure 4A:
Figure 4B:
Figure 4B:

FIGS. 4A through 4B depict screening of CHO clones for stable, tetracycline-regulated expression of GnT V (FIG. 4A) or myc-tagged GnT III (FIG. 4B) glycosyltransferases by western blot analysis. CHOt17 cells were co-transfected with a vector for expression of puromycin resistance (pPUR) and either pUHD10-3GnTV (FIG. 4A) or pUDH10-3GnTIIIm (FIG. 4B) and stable CHO clones were selected for resistance to puromycin (7.5µ/ml), in the presence of tetracycline (2 µg/ml). Eight clones (1-8) for each glycosyltransferase were cultured for 48 h in the absence or presence (+) of tetracycline (2% µg/ml) and analysed by western blot using either an anti-GnT V antibody (FIG. 4A) or an anti-myc (9E10) antibody (FIG. 4B).

Figure 5A:
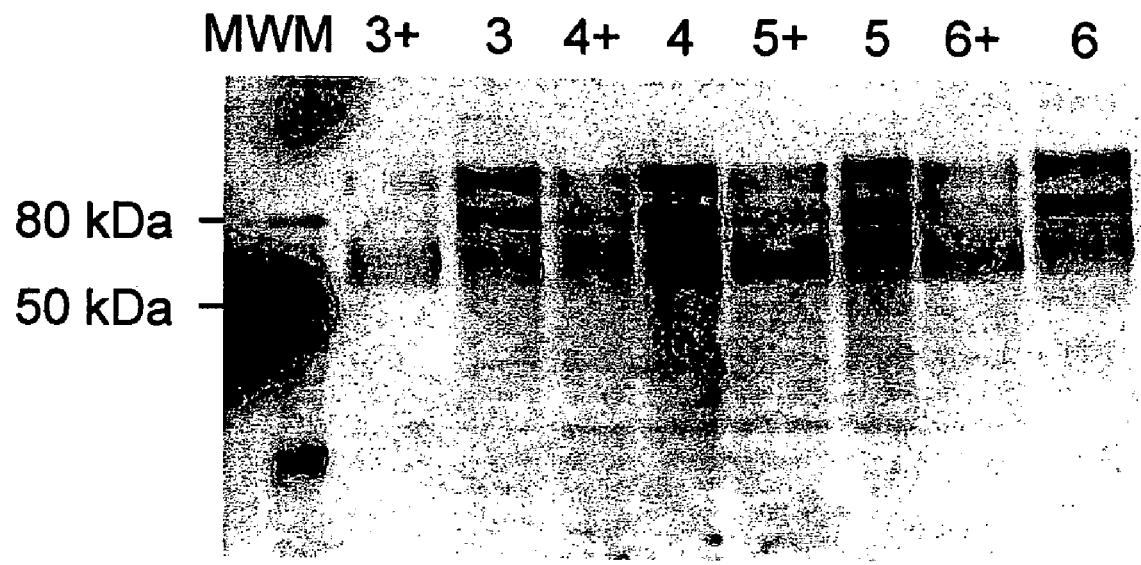
Figure 5B:
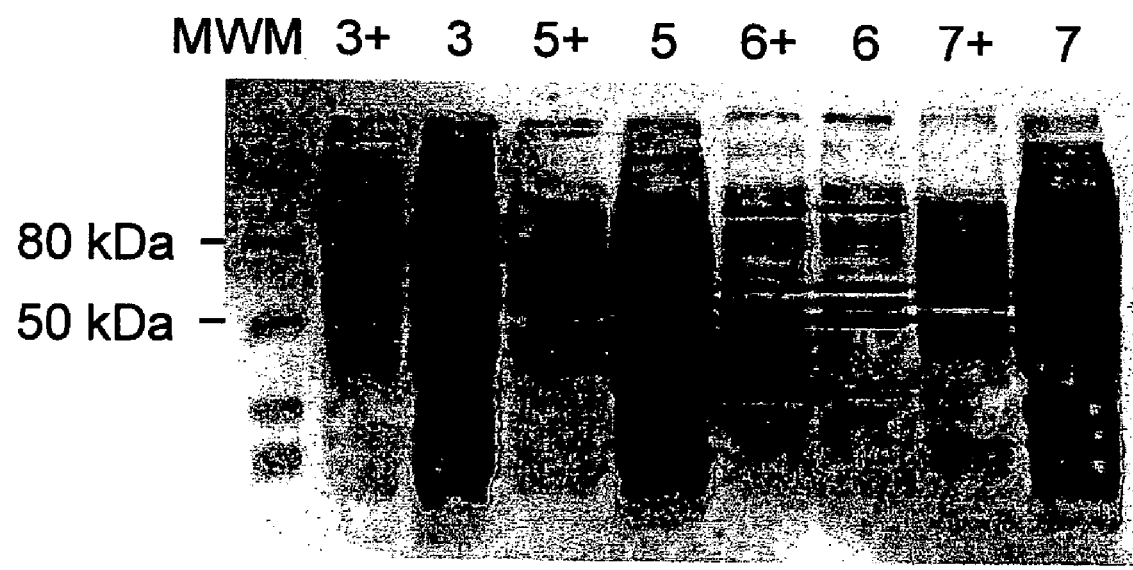
Figure 6A:
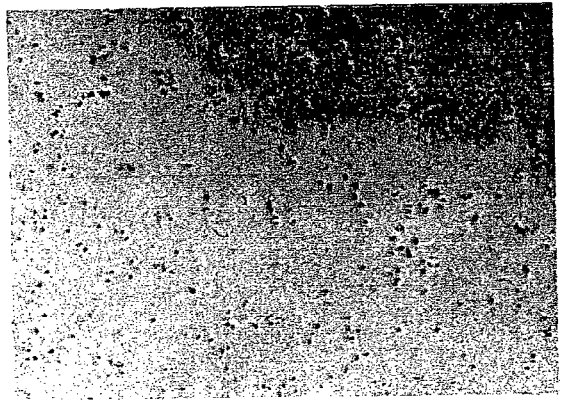
Figure 6B:
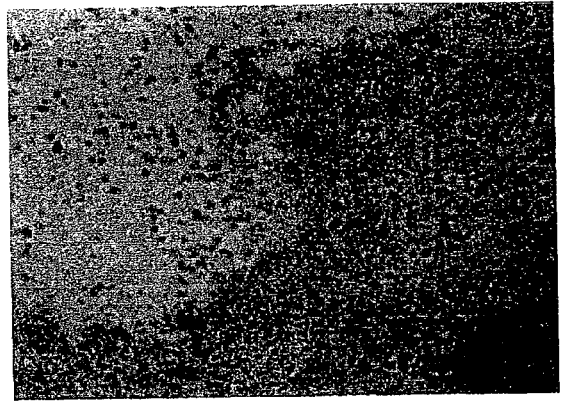
Figure 6C:
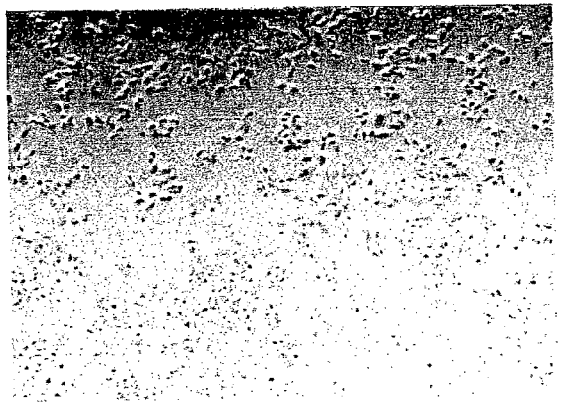
Figure 6D:
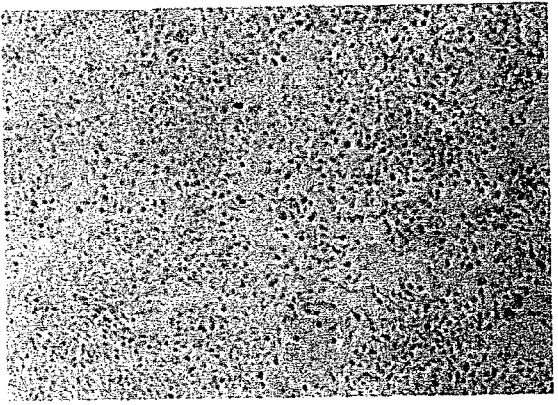

FIGS. 5A and 5B depict verification of activity of heterologous GnT V (FIG. 5A) and GnT III (FIG. 5B) glycosyltransferaseas in vivo by lectin blot analysis. Cellular glycoproteins from various stable clones (numbered as in FIG. 4), cultured in the absence or presence (+) of tetracycline (2 µg/ml), were resolved by SDS-PAGE, blotted to a membrane, and probed with either L-PHA (FIG. 5A) or E-PHA (FIG. 5B) lectins. These lectins bind with higher affinity to the oligosaccharide products of reactions catalyzed by GnT V and GnT III, respectively, than to the oligosaccharide substrates of these reactions. A molecular weight marker (MWM) was run in parallel. A comparison of lectin blots in FIGS. 5A and 5B indicates a broader range of substrates, among the endogenous CHO cell glycoproteins, for GnT III (FIG. 5B) than for GnT V (FIG. 5A).

FIGS. 6A through 6D depict inhibition of cell growth upon glycosyltransferase overexpression. CHO-tet-GnTIIIm cells were seeded to 5-10% confluency and cultured in the absence (FIGS. 6A and 6B) or presence (FIGS. 6C and 6D) of tetracycline. Cultures were photographed 45 (FIGS. 6A and 6C) and 85 (FIGS. 116B and 6D) hours after seeding.

Figure 7A:
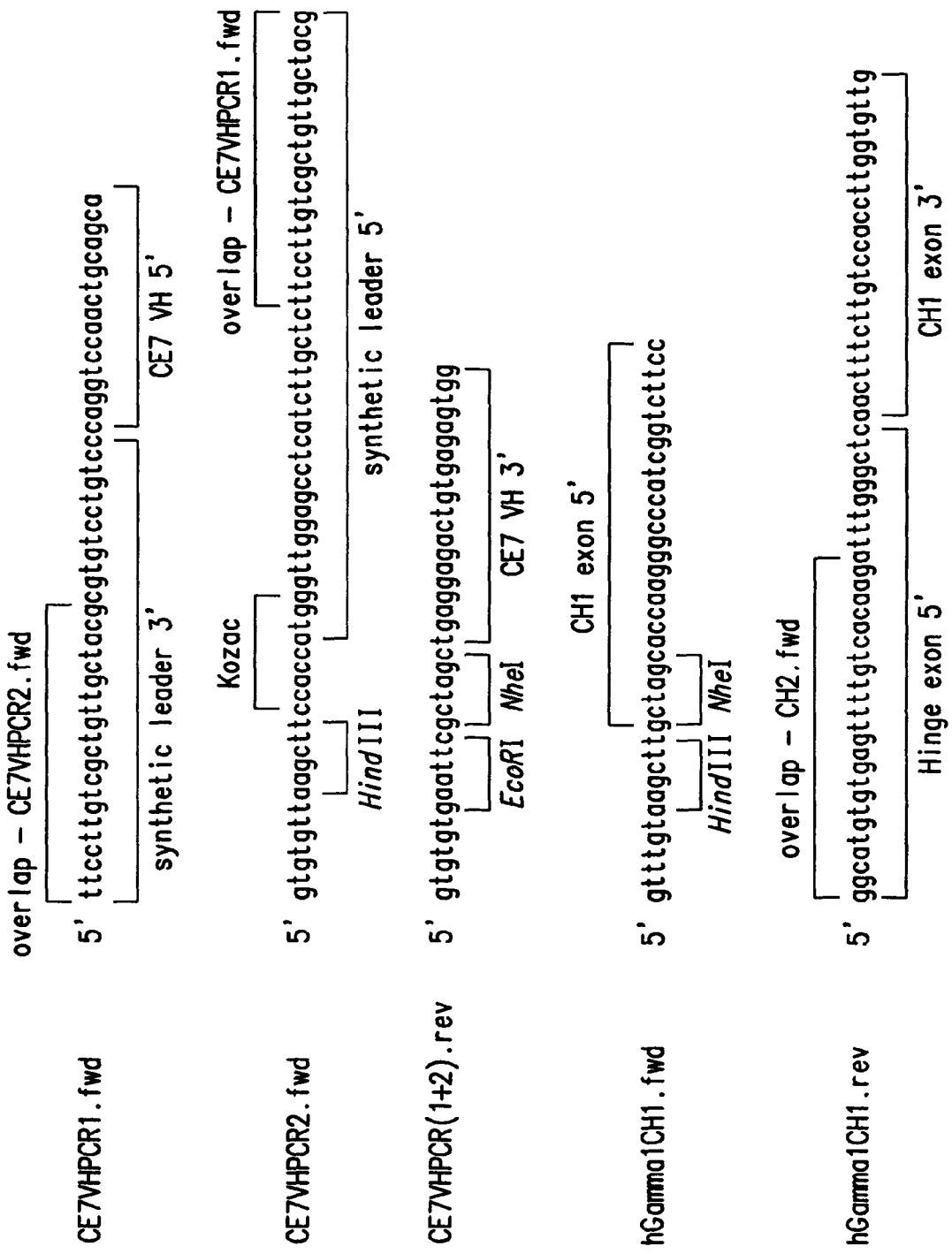
Figure 7B:
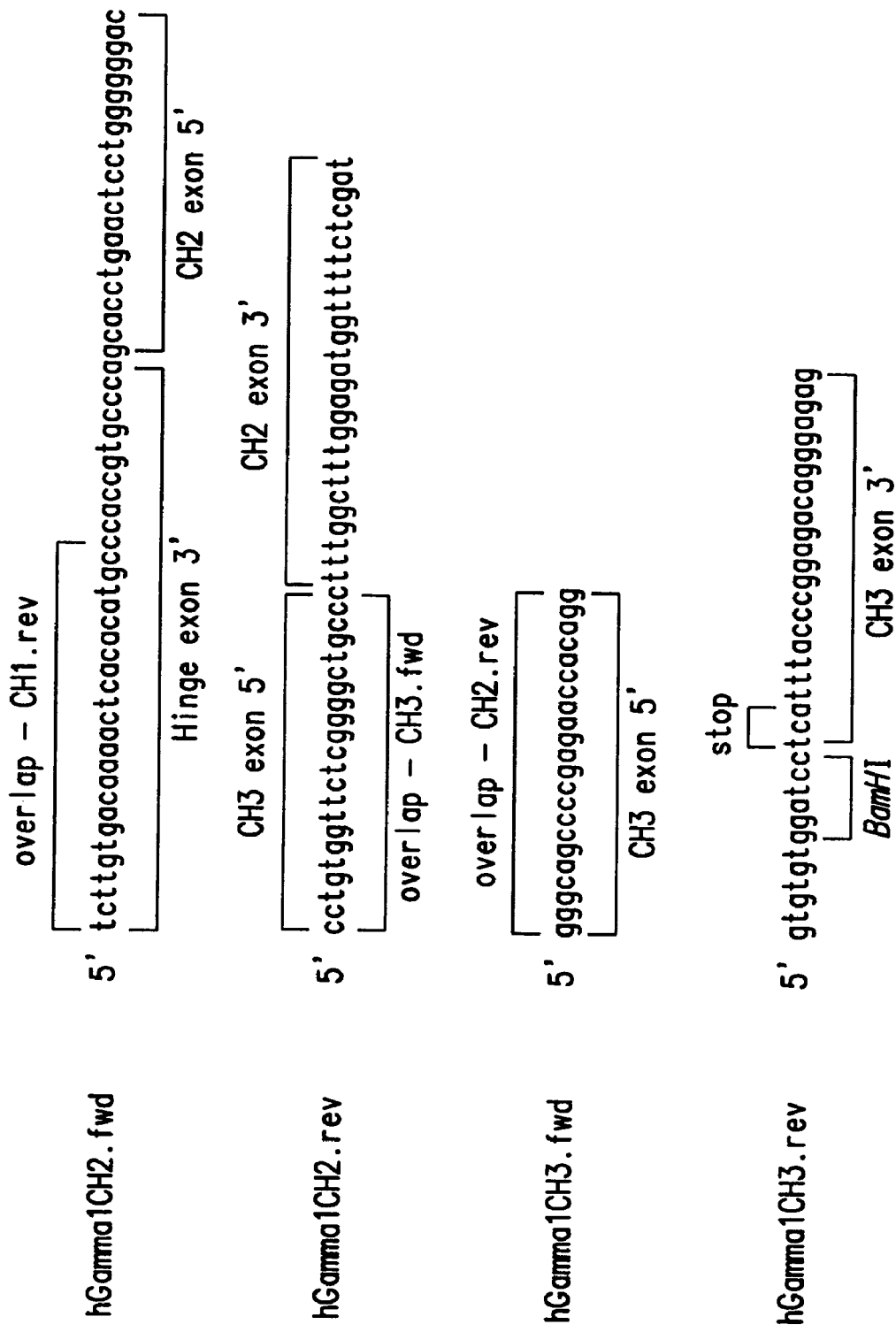

FIG. 7 depicts sequences of oligonucleotide primers used in PCRs for the construction of the chCE7 heavy chain gene. Forward and reverse primers are identified by the suffixes ".fwd" and ".rev", SEQ ID NO:1-9 respectively. Overlaps between different primers, necessary to carry out secondary PCR steps using the product of a primary PCR step as a template, are indicated. Restriction sites introduced, sequences annealing to the CE7 chimeric genomic DNA, and the synthetic leader sequence introduced, are also indicated.

Figure 8:
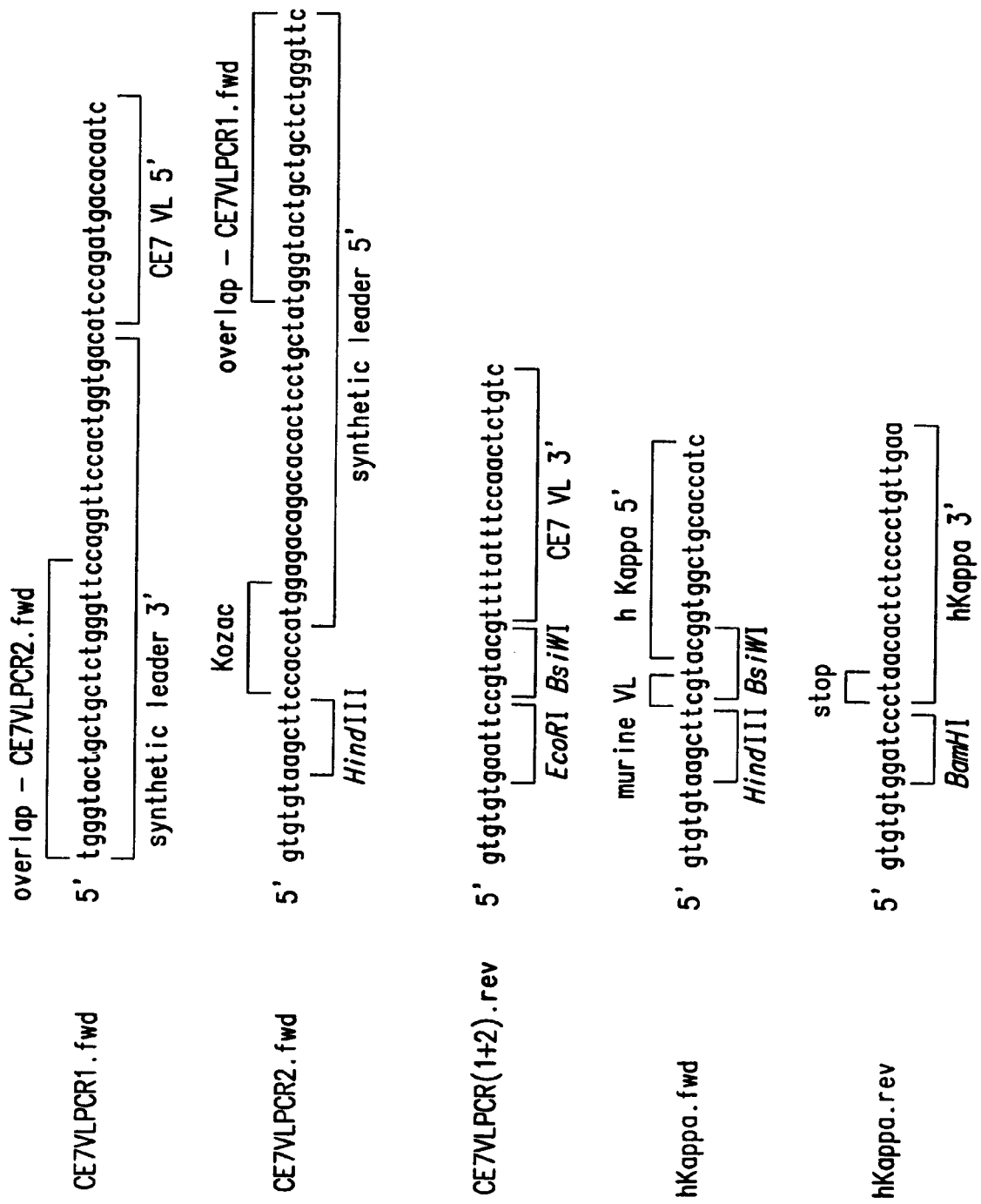

FIG. 8 depicts sequences of oligonucleotide primers used in PCRs for the construction of the chCE7 light chain gene. Forward and reverse primers are identified by the suffixes ".fwd" and ".rev" SEQ ID NO:10-14 respectively. Overlaps between different primers, necessary to carry out secondary PCR steps using as a template the product of a primary PCR step, are indicated. Restriction sites introduced, sequences annealing to the CE7 chimeric genomic DNA, and the leader sequence introduced, are also indicated.

Figure 9:
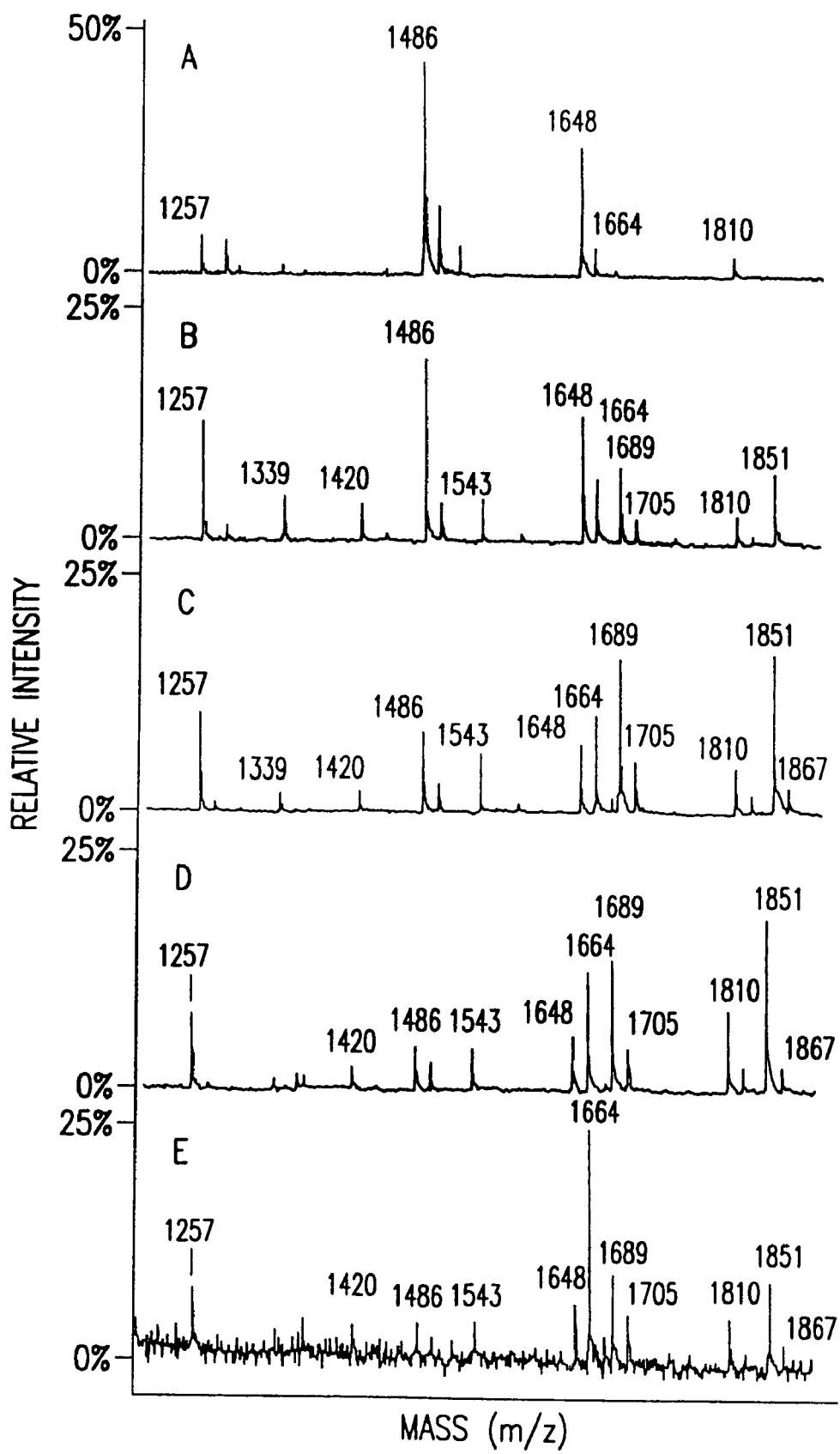

FIG. 9 depicts MALDI/TOF-MS spectra of neutral oligosaccharide mixtures from chCE7 samples produced either by SP2/0 mouse myeloma cells (FIG. 9A, oligosaccharides from 50 µg of CE7-SP2/0), or by CHO-tetGnTIII-chCE7 cell cultures differing in the concentration of tetracycline added to the media, and therefore expressing the GnT III gene at different levels. In decreasing order of tetracycline concentration, i e., increasing levels of GnT III gene expression, the latter samples are: CE7-2000t (FIG. 9B, oligosaccharides from 37.5 µg of antibody), CE7-60t (FIG. 9C, oligosaccharides from 37.5 µg of antibody, CE7-30t (FIG. 9D, oligosaccharides from 25 µ/g of antibody) and CE7-15t (FIG. 9E, oligosaccharides from 10 µg of antibody).

Figure 10:
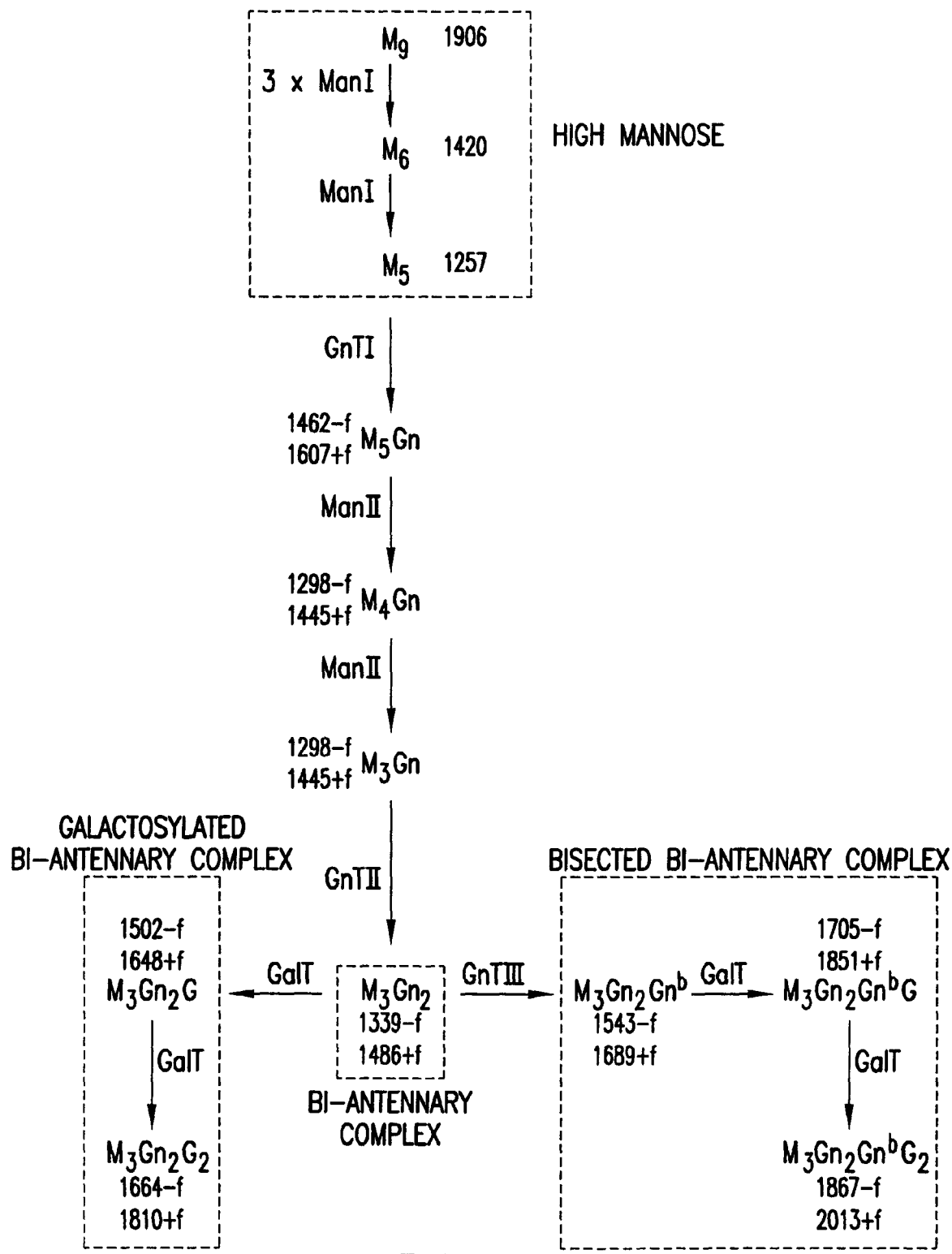

FIG. 10 depicts N-linked oligosaccharide biosynthetic pathways leading to bisected complex oligosaccharides via a GnT III-catalyzed reaction. M stands for Mannose; Gn, N-acetylglucosamine (GlcNAc); G, galactose; $Gn^b$, bisecting GlcNAc; f, fucose. The oligosaccharide nomenclature consists of enumerating the M, Gn, and G residues attached to the core oligosaccharide and indicating the presence of a bisecting G1 cNAc by including a $Gn^b$. The oligosaccharide core is itself composed of 2 Gn residues and may or may not include a fucose. The major classes of oligosaccharides are shown inside dotted frames. Man I stands for Golgi mannosidase; GnT, G1 cNAc transferase; and GalT, for galactosyltransferase. The mass associated with the major, sodium-associated oligosaccharide ion that is observed MALDI/TOF-MS analysis is shown beside each oligosaccharide. For oligosaccharides which can potentially be core-fucosylated, the masses associated with both fucosylated (+f) and non-fucosylated (−f) forms are shown.

Figure 11:
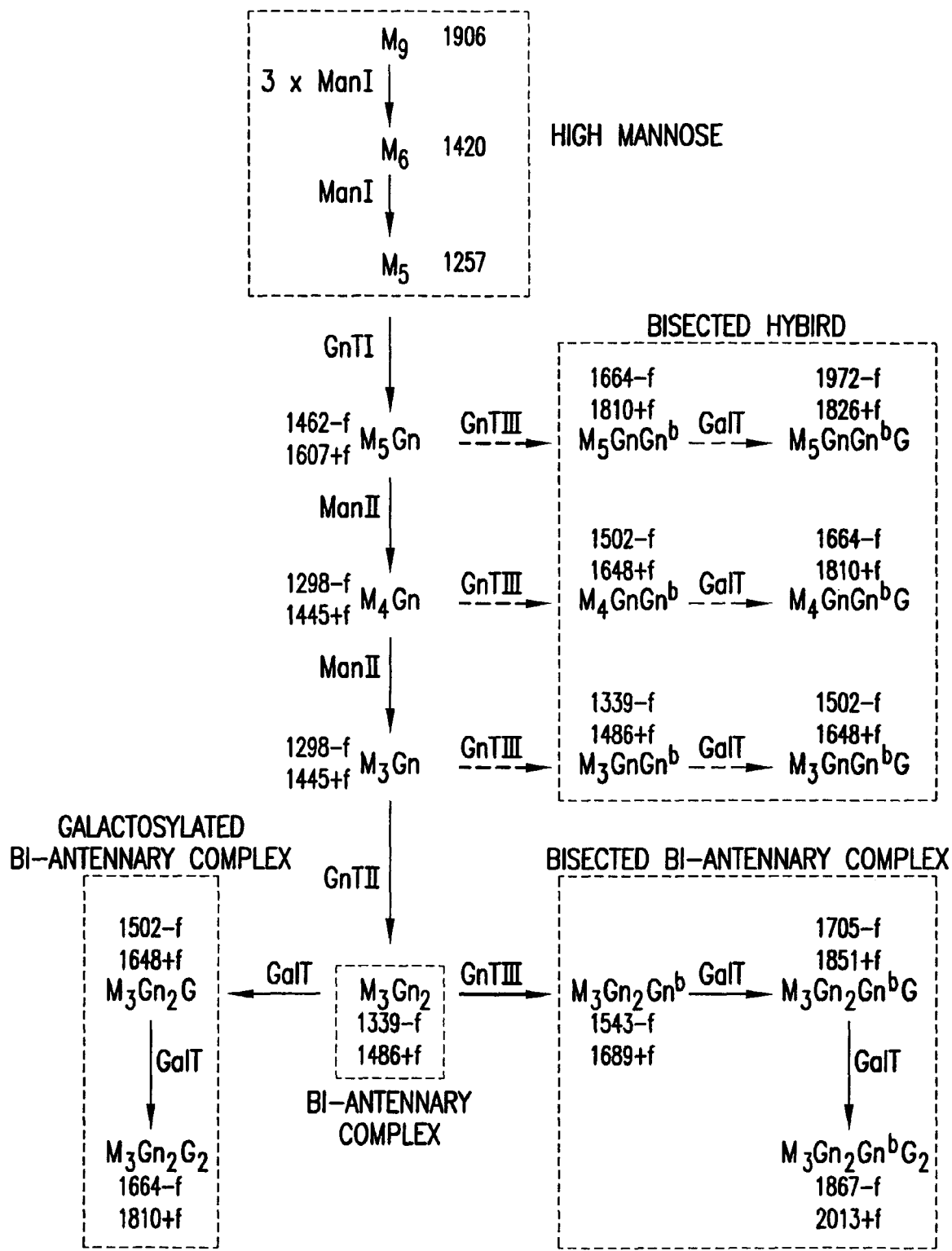

FIG. 11 depicts N-linked oligosaccharide biosynthetic pathway leading to bisected complex and bisected hybrid oligosaccharides via GnT III-catalyzed reactions. M stands for mannose; Gn N-acetylglucosamine (GlcNAc); G, galactose; $Gn^b$, bisecting G1 cNAc; f, fucose. The oligosaccharide nomenclature consists of enumerating the M, Gn, and G residues attached to the common oligosaccharide and indicating the presence of bisecting GlcNAc by including a $Gn^b$. The oligosaccharide core is itself composed of 2 Gn residues and may or not include a fucose. The major classes of oligosaccharides are shown inside dotted frames. Man I stands for Golgi mannosidase; TnT, GlcNAc transferase; and GalT, for galactosyltransferase. The mass associated with major, sodium-associated oligosaccharide ion that is observed in MALDI/TOF-MS analysis is shown beside each oligosaccharide. For oligosaccharides which can potentially be core-fucosylated, the masses associated with both fucosylated (+f) and non -fucosylated (−f) forms are shown.

Figure 12:
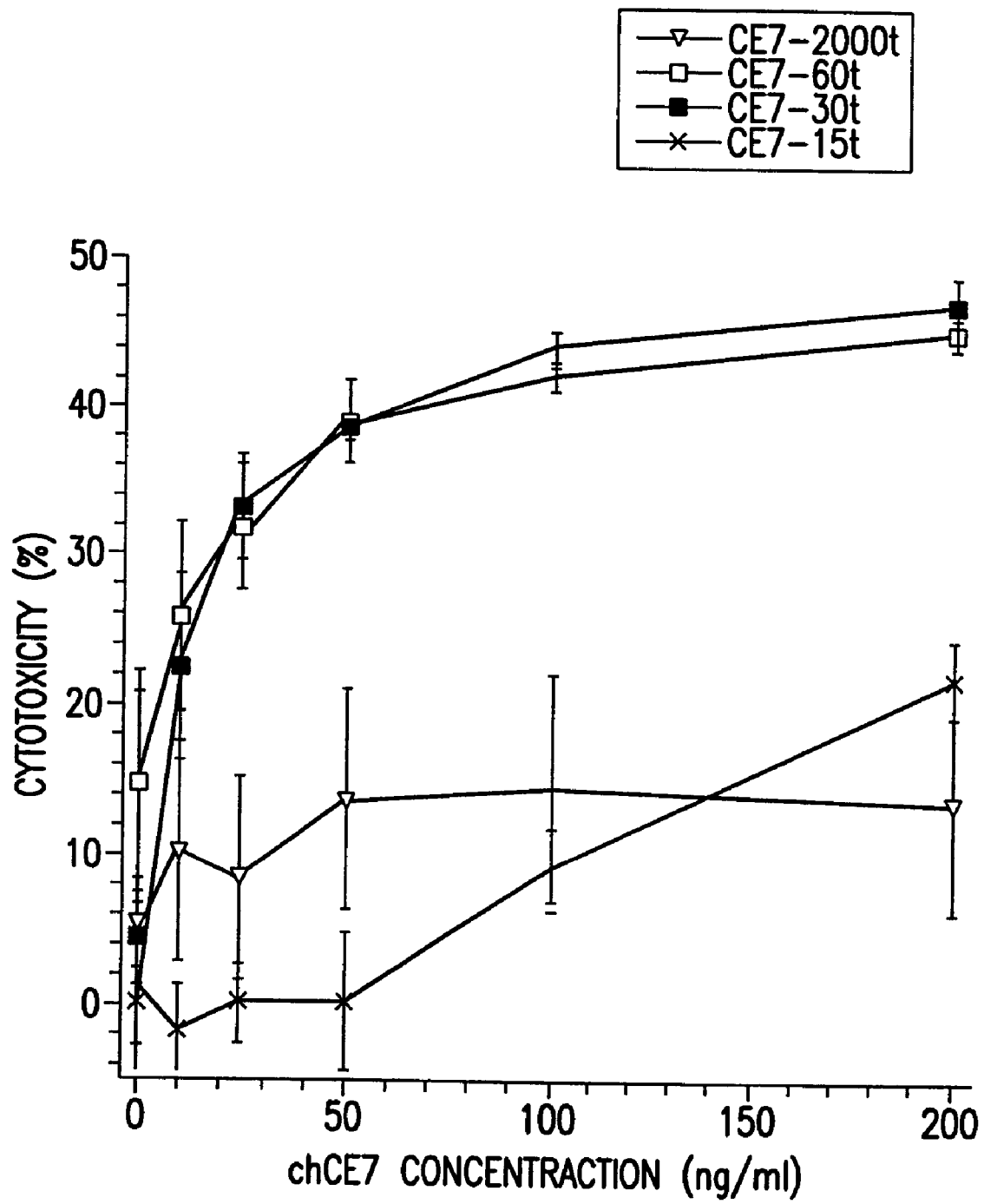

FIG. 12 depicts ADCC activity of different chCE7 samples. Lysis of IMR-32 neuroblastoma cells by human lymphocytes (target:effector ratio of 1:19, 16 h incubation at 37° C.), mediated by different concentrations of chCE7 samples, was measured via retention of a fluorescent dye. The percentage of cytotoxicity is calculated relative to a total lysis control (by means of a detergent), after subtraction of the signal in the absence of antibody.

Figure 13:
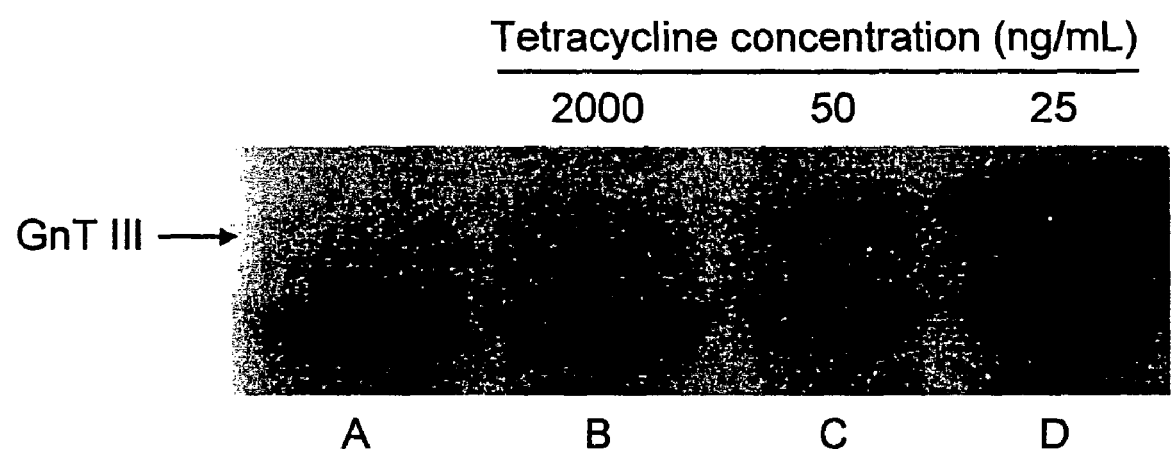

FIG. 13 depicts the GnT III expression of different cultures of CHO-tet-GnTIII grown at different tetracycline concentrations used to produce distinct C2B8 antibody samples. Cell lysates from each culture grown at 2000 ng/ml (Lane C) and 25 ng/ml (Lane D) tetracycline concentrations were resolved by SDS-PAGE, blotted onto a membrane, and probed with 9E10 (see supra) and anti-mouse horseradish peroxidase as primary and secondary antibodies, respectively. Lane A depicts a negative control.

Figure 14A:
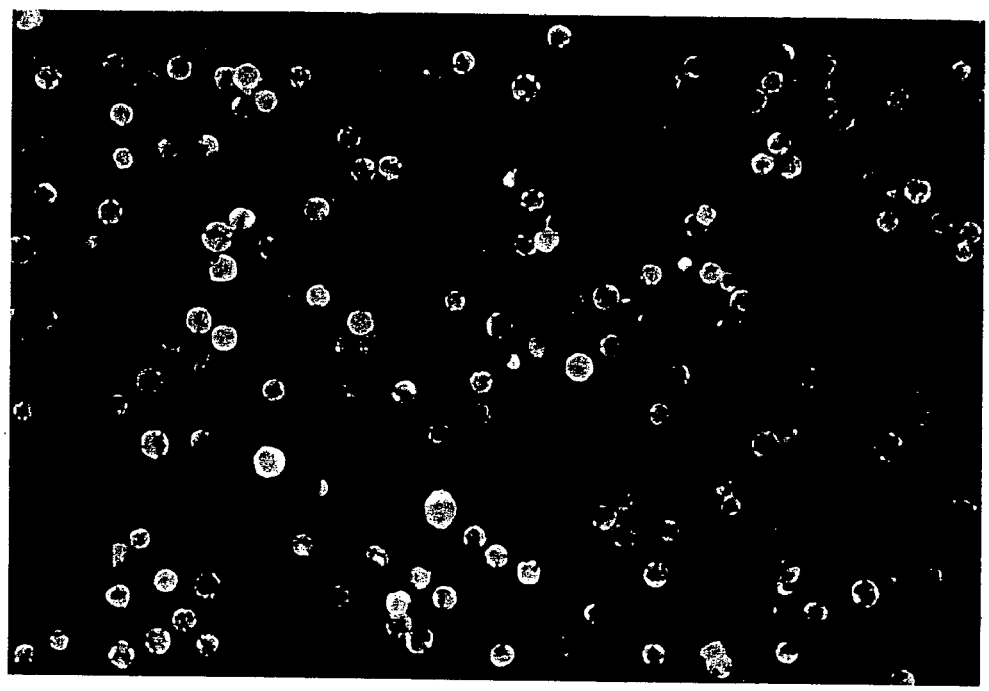
Figure 14B:
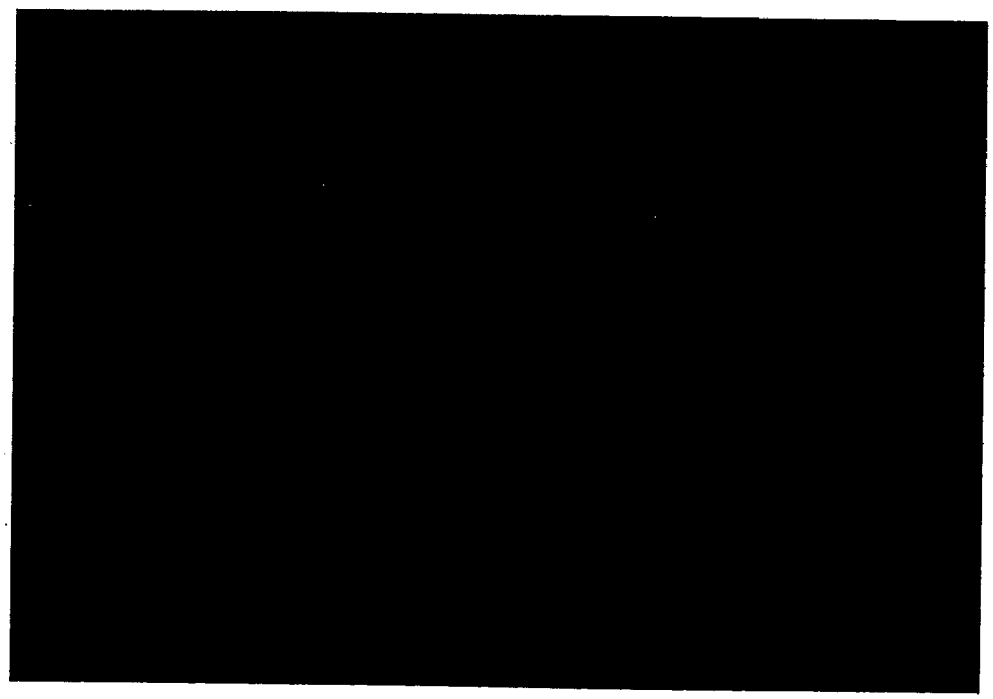

FIGS. 14A and 14B depict the specificity of antigen binding of the C2B8 anti-CD20 monoclonal antibody using an indirect immunofluorescence assay with cells in suspension. CD20 positive cells (SB cells; ATCC deposit no.ATCC CCL120) and CD20 negative cells (HSB cells; ATCC deposit no. ATCC CCL 120.1), FIG. 14A and 14B respectively, were utilized. Cells of each type were incubated with C2B8 antibody produced at 25 ng/ml tetracycline as a primary antibody. Negative controls included HBSSB instead of primary antibody. An anti-human IgG Fc specific, polyclonal, FITC conjugated antibody was used for all samples as a secondary antibody.

FIG. 15 depicts the ADCC activity of different C2B8 antibody samples at different antibody concentrations (0.04-5 μg/ml). Sample C2B8-nt represents the ADCC activity of the C2B8 antibody produced in a cell line without GnT III expression. Samples C2B8-2000t, C2B8-50t and C2B8-25t show the ADCC activity of three antibody samples produced at decreasing tetracycline concentrations (i.e., increasing GnT III expression).

VI. DEFINITIONS

Terms are used herein as generally used in the art, unless otherwise defined in the following:

As used herein, the term antibody is intended to include whole antibody molecules, antibody fragments, or fusion proteins that include a region equivalent to the Fc region of an immunoglobulin.

As used herein, the term glycoprotein-modifying glycosyl transferase refers to an enzyme that effects modification of the glycosylation pattern of a glycoprotein. Examples of glycoprotein-modifing glycosyl transferases include, but are not limited to glycosyl transferases such as GnT III, GnT V, GalT, and Man II.

As used herein, the term glycosylation engineering is considered to include any sort of change to the glycosylation pattern of a naturally occurring polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation.

As used herein, the term host cell covers any kind of cellular system which can be engineered to generate modified glycoforms of proteins, protein fragments, or peptides of interest, including antibodies and antibody fragments. Typically, the host cells have been manipulated to express optimized levels of at least one glycoprotein-modifying glycosyl transferase, including, but not limited to GnT III, GnT V, GalT, and Man II, and/or at least one glycosidase. Host cells include cultured cells, e.g., mammalian cultured cells, such as CHO cells, BHK cells, NS0 cells, SP2/0 cells, or hybridoma cells, yeast cells, and insect cells, to name only few, but also cells comprised within a transgenic animal or cultured tissue.

As used herein, the term Fc-mediated cellular cytotoxicity is intended to include antibody dependent cellular cytotoxicity (ADCC), and cellular cytotoxicity directed to those cells that have been engineered to express on their cell surface an Fc-region or equivalent region of an immunoglobin G, and cellular cytotoxicity mediated by a soluble fusion protein consisting of a target protein domain fused to the N-terminus of an Fc-region or equivalent region of an immunoglobulin G.

VII. DETAILED DESCRIPTION OF THE INVENTION

A. General Overview

The objective of the present invention is to provide glycoforms of proteins, in particular antibodies, including whole antibody molecules, antibody fragments, or fusion proteins that include a region equivalent to the Fc region of an immunoglobulin, to produce new variants of a therapeutic protein. The invention is based, in part, on the inventors' discovery that the glycosylation reaction network of a cell can be manipulated to maximize the proportion of certain glycoforms within the population, and that certain glycoforms have improved therapeutic characteristics. The invention is further based, in part, on the discovery of ways to identify glycoforms of proteins which have an improved therapeutic value, and how to generate them reproducibly. The invention is further based, in part, on the discovery that there is a preferred range of glycoprotein-modifying glycosyl transferase expression in the antibody-generating cell, for increasing complex N-linked oligosaccharides carrying bisecting GlcNAc.

As such, the present invention is directed, generally, to methods for the glycosylation engineering of proteins to alter and improve their therapeutic properties. More specifically, the present invention describes methods for producing in a host cell an antibody which has an altered glycosylation pattern resulting in an enhanced antibody dependent cellular cytotoxicity (ADCC). For the practice of the methods, the present invention provides host cells which harbor a nucleic acid encoding an antibody and at least one nucleic acid encoding a glycoprotein-modifying glycosyl transferase. Further, the present invention provides methods and protocols of culturing such host cells under conditions which permit the expression of the desired antibody having an altered glycosylation pattern resulting in an enhanced antibody dependent cellular cytotoxicity. Further, methods for isolating the so generated antibody with enhanced antibody dependent cellular cytotoxicity are described.

In more specific embodiments of the invention, two monoclonal antibodies, namely the anti-neuroblastoma antibody chCE7, and the anti-CD20 antibody C2B8, have been used as model therapeutic glycoproteins, and the target glycoforms have been those carrying a special class of carbohydrate, namely bi-antennary complex N-linked oligosaccharides modified with bisecting N-acetylglucosamine (GlcNAc). In the model system provided by the invention, CHO cells are used as host cells, although many other cell systems may be contemplated as host cell system. The glycosyl transferase that adds a bisecting GlcNAc to various types of N-linked oligosaccharides, GlcNAc-transferase III (GnT III), is not normally produced by CHO cells. Stanley and Campell, 1984, *J. Biol. Chem.* 261:13370-13378.

To investigate the effects of GnT III overexpression experimentally, a CHO cell line with tetracycline-regulated overexpression of a rat GnT III cDNA was established. Using this experimental system, the inventors discovered that overexpression of GnT III to high levels led to growth inhibition and was toxic to the cells. Another CHO cell line with tetracycline-regulated overexpression of GnT V, which is a distinct glycosyl transferase, showed the same inhibitory effect, indicating that this may be a general feature of glycoprotein-modifying glycosyl transferase overexpression. The effect of the enzyme expression on the cell growth sets an upper limit to the level of glycoprotein-modifying glycosyl transferase overexpression and may therefore also limit the extent to which poorly accessible glycosylation sites can be modified by engineering of glycosylation pathways and patterns using unregulated expression vectors.

The production of a set of chCE7 mAb and C2B8 samples differing in their glycoform distributions by controlling GnT III expression in a range between basal and toxic levels are disclosed. Measurement of the ADCC activity of the chCE7 mAb samples showed an optimal range of GnT III expression for maximal chCE7 in vitro biological activity. The activity correlated with the level of Fc-associated bisected, complex oligosaccharides. Expression of GnT III within the practical range, i.e., where no significant growth inhibition and toxicity are observed, led to an increase of the target bisected, complex structures for this set of chCE7 samples. The pattern of oligosaccharide peaks in MALDI/TOF-mass spectrometric analysis of chCE7 samples produced at high levels of GnT III indicates that a significant proportion of potential GnT III substrates is diverted to bisected hybrid oligosaccharide by-products. Minimization of these by-products by further engineering of the pathway could therefore be valuable.

B. Identification and Generation of Nucleic Acids Encoding a Protein for which Modification of the Glycosylation Pattern is Desired The present invention provides host cell systems suitable for the generation of altered glycoforms of any protein, protein fragment or peptide of interest, for which such an alteration in the glycosylation pattern is desired. The nucleic acids encoding such protein, protein fragment or peptide of interest may be obtained by methods generally known in the art. For example, the nucleic acid may be isolated from a cDNA library or genomic library. For a review of cloning strategies which may be used, see, e.g., Maniatis, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

In an alternate embodiment of the invention, the coding sequence of the protein, protein fragment or peptide of interest may be synthesized in whole or in part, using chemical methods well known in the art. See, for example, Caruthers et al., 1980, *Nuc. Acids Res. Symp. Ser.* 7:215-233; Crea and Horn, 1980, *Nuc. Acids Res. USA* 9:2331; Matteucci and Caruthers, 1980, *Tetrahedron Letters* 21:719; Chow and Kempe, 1981, *Nuc. Acids Res.* 9:2807-2817. Alternatively, the protein itself could be produced using chemical methods to synthesize its amino acid sequence in whole or in part. For example, peptides can be synthesized by solid phase techniques, cleaved from the resin, and purified by preparative high performance liquid chromatography. E.g., see Creighton, 1983, *Protein Structures And Molecular Principles*, W.H. Freeman and Co., N.Y. pp. 50-60. The composition of the synthetic peptides may be confirmed by amino acid analysis or sequencing (e.g., the Edman degradation procedure; see Creighton, 1983, *Proteins Structures and Molecular Principles*, W.H. Freeman and Co., N.Y., pp. 34-49).

In preferred embodiments, the invention provides methods for the generation and use of host cell systems for the production of glycoforms of antibodies or antibody fragments or fusion proteins which include antibody fragments with enhanced antibody-dependent cellular cytotoxicity. Identification of target epitopes and generation of antibodies having potential therapeutic value, for which modification of the glycosylation pattern is desired, and isolation of their respective coding nucleic acid sequence is within the scope of the invention.

Various procedures known in the art may be used for the production of antibodies to target epitopes of interest. Such antibodies include but are not limited to polyclonal, monoclonal, chimeric, single chain, Fab fragments and fragments produced by an Fab expression library. Such antibodies may be useful, e.g., as diagnostic or therapeutic agents. As therapeutic agents, neutralizing antibodies, i.e., those which compete for binding with a ligand, substrate or adapter molecule, are of especially preferred interest.

For the production of antibodies, various host animals are immunized by injection with the target protein of interest including, but not limited to, rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to the target of interest may be prepared using any technique which provides for the production of antibody molecules by continuous cell lines in culture. These include, but are not limited to, the hybridoma technique originally described by Kohler and Milstein, 1975, *Nature* 256:495-497, the human B-cell hybridoma technique (Kosbor et al., 1983, *Immunology Today* 4:72; Cote et al., 1983, *Proc. Natl. Acad. Sci. USA*. 80:2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al., 1984, *Proc. Natl. Acad. Sci. USA*. 81:6851-6855; Neuberger et al., 1984, *Nature* 312: 604-608; Takeda et al., 1985, *Nature* 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies having a desired specificity.

Antibody fragments which contain specific binding sites of the target protein of interest may be generated by known techniques. For example, such fragments include, but are not limited to, F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science* 246:1275-1281) to allow rapid and easy identification of monoclonal Fab fragments with the desired specificity to the target protein of interest.

Once an antibody or antibody fragment has been identified for which modification in the glycosylation pattern are desired, the coding nucleic acid sequence is identified and isolated using techniques well known in the art. See, supra.

C. Generation of Cell Lines for the Production of Proteins with Altered Glycosylation Pattern The present invention provides host cell expression systems for the generation of proteins having modified glycosylation patterns. In particular, the present invention provides host cell systems for the generation of glycoforms of proteins having an improved therapeutic value. Therefore, the invention provides host cell expression systems selected or engineered to increase the expression of a glycoprotein-modifying glycosyltransferase. Specifically, such host cell expression systems may be engineered to comprise a recombinant nucleic acid molecule encoding a glycoprotein-modifying glycosyltransferase, operatively linked to a constitutive or regulated promoter system. Alternatively, host cell expression systems may be employed that naturally produce, are induced to produce, and/or are selected to produce a glycoprotein-modifying glycosyltransferase.

In one specific embodiment, the present invention provides a host cell that has been engineered to express at least one nucleic acid encoding a glycoprotein-modifying glycosyl transferase. In one aspect, the host cell is transformed or transfected with a nucleic acid molecule comprising at least one gene encoding a glycoprotein-modifying glycosyl transferase. In an alternate aspect, the host cell has been engineered and/or selected in such way that an endogenous glycoprotein-modifying glycosyl transferase is activated. For example, the host cell may be selected to carry a mutation triggering expression of an endogenous glycoprotein-modifying glycosyl transferase. This aspect is exemplified in one specific embodiment, where the host cell is a CHO lec10 mutant. Alternatively, the host cell may be engineered such that an endogenous glycoprotein-modifying glycosyl transferase is activated. In again another alternative, the host cell is engineered such that an endogenous glycoprotein-modifying glycosyl transferase has been activated by insertion of a regulated promoter element into the host cell chromosome. In a further alternative, the host cell has been engineered such that an endogenous glycoprotein-modifying glycosyl transferase has been activated by insertion of a constitutive promoter element, a transposon, or a retroviral element into the host cell chromosome.

Generally, any type of cultured cell line can be used as a background to engineer the host cell lines of the present invention. In a preferred embodiment, CHO cells, BHK cells, NS0 cells, SP2/0 cells, or a hybridoma cell line is used as the background cell line to generate the engineered host cells of the invention.

The invention is contemplated to encompass engineered host cells expressing any type of glycoprotein-modifying glycosyl transferase as defined herein. However, in preferred embodiments, at least one glycoprotein-modifying glycosyl transferase expressed by the host cells of the invention is GnT III, or, alternatively, β(1,4)-N-acetylglucosaminyltransferase V (GnT V). However, also other types of glycoprotein-modifying glycosyl transferase may be expressed in the host system, typically in addition to GnT III or GnT V, including β(1,4)-galactosyl transferase (GalT), and mannosidase II (Man II). In one embodiment of the invention, GnT III is coexpressed with GalT. In another embodiment of the invention, GnT III is coexpressed with Man II. In a further embodiment of the invention, GnT III is coexpressed with GalT and Man II. However, any other permutation of glycoprotein-modifying glycosyl transferases is within the scope of the invention. Further, expression of a glycosidase in the host cell system may be desired.

One or several nucleic acids encoding a glycoprotein-modifying glycosyl transferase may be expressed under the control of a constitutive promoter or, alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding glycoprotein-modifying glycosyl transferases are comprised within the host cell system, some of them may be expressed under the control of a constitutive promoter, while others are expressed under the control of a regulated promoter. The optimal expression levels will be different for each protein of interest, and will be determined using routine experimentation. Expression levels are determined by methods generally known in the art, including Western blot analysis using a glycosyl transferase specific antibody, Northern blot analysis using a glycosyl transferase specific nucleic acid probe, or measurement of enzymatic activity. Alternatively, a lectin may be employed which binds to biosynthetic products of the glycosyl transferase, for example, $E_4$-PHA lectin. In a further alternative, the nucleic acid may be operatively linked to a reporter gene; the expression levels of the glycoprotein-modifying glycosyl transferase are determined by measuring a signal correlated with the expression level of the reporter gene. The reporter gene may transcribed together with the nucleic acid(s) encoding said glycoprotein-modifying glycosyl transferase as a single mRNA molecule; their respective coding sequences may be linked either by an internal ribosome entry site (IRES) or by a cap-independent translation enhancer (CITE). The reporter gene may be translated together with at least one nucleic acid encoding said glycoprotein-modifying glycosyl transferase such that a single polypeptide chain is formed. The nucleic acid encoding the glycoprotein-modifying glycosyl transferase may be operatively linked to the reporter gene under the control of a single promoter, such that the nucleic acid encoding the glycoprotein-modifying glycosyl transferase and the reporter gene are transcribed into an RNA molecule which is alternatively spliced into two separate messenger RNA (mRNA) molecules; one of the resulting mRNAs is translated into said reporter protein, and the other is translated into said glycoprotein-modifying glycosyl transferase.

If several different nucleic acids encoding a glycoprotein-modifying glycosyl transferase are expressed, they may be arranged in such way that they are transcribed as one or as several mRNA molecules. If they are transcribed as a single mRNA molecule, their respective coding sequences may be linked either by an internal ribosome entry site (IRES) or by a cap-independent translation enhancer (CITE). They may be transcribed from a single promoter into an RNA molecule which is alternatively spliced into several separate messenger RNA (mRNA) molecules, which then are each translated into their respective encoded glycoprotein-modifying glycosyl transferase.

In other embodiments, the present invention provides host cell expression systems for the generation of therapeutic proteins, for example antibodies, having an enhanced antibody-dependent cellular cytotoxicity, and cells which display the IgG Fc region on the surface to promote Fc-mediated cytotoxicity. Generally, the host cell expression systems have been engineered and/or selected to express nucleic acids encoding the protein for which the production of altered glycoforms is desired, along with at least one nucleic acid encoding a glycoprotein-modifying glycosyl transferase. In one embodiment, the host cell system is transfected with at least one gene encoding a glycoprotein-modifying glycosyl transferase. Typically, the transfected cells are selected to identify and isolate clones that stably express the glycoprotein-modifying glycosyl transferase. In another embodiment, the host cell has been selected for expression of endogenous glycosyl transferase. For example, cells may be selected carrying mutations which trigger expression of otherwise silent glycoprotein-modifying glycosyl transferases. For example, CHO cells are known to carry a silent GnT III gene that is active in certain mutants, e.g., in the mutant Lec10. Furthermore, methods known in the art may be used to activate silent glycoprotein-modifying glycosyl transferase genes, including the insertion of a regulated or constitutive promoter, the use of transposons, retroviral elements, etc. Also the use of gene knockout technologies or the use of ribozyme methods may be used to tailor the host cell's glycosyl transferase and/or glycosidase expression levels, and is therefore within the scope of the invention.

Any type of cultured cell line can be used as background to engineer the host cell lines of the present invention. In a preferred embodiment, CHO cells, BHK cells, NS0 cells, SP2/0 cells. Typically, such cell lines are engineered to further comprise at least one transfected nucleic acid encoding a whole antibody molecule, an antibody fragment, or a fusion protein that includes a region equivalent to the Fc region of an immunoglobulin. In an alternative embodiment, a hybridoma cell line expressing a particular antibody of interest is used as background cell line to generate the engineered host cells of the invention.

Typically, at least one nucleic acid in the host cell system encodes GnT III, or, alternatively, GnT V. However, also other types of glycoprotein-modifying glycosyl transferase may be expressed in the host system, typically in addition to GnT III or GnT V, including GalT, and Man II. In one embodiment of the invention, GnT III is coexpressed with GalT. In another embodiment of the invention, GnT III is coexpressed with Man II. In a further embodiment of the invention, GnT III is coexpressed with GalT and Man II. However, any other permutation of glycoprotein-modifying glycosyl transferases is within the scope of the invention. Further, expression of a glycosidase in the host cell system may be desired.

One or several nucleic acids encoding a glycoprotein-modifying glycosyl transferase may be expressed under the control of a constitutive promoter, or alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding glycoprotein-modifying glycosyl transferases are comprised within the host cell system, some of them may be expressed under the control of a constitutive promoter, while others are expressed under the control of a regulated promoter. The optimal expression levels will be different for each protein of interest, and will be determined using routine experimentation. Expression levels are determined by methods generally known in the art, including Western blot analysis using a glycosyl transferase specific antibody, Northern blot analysis using a glycosyl transferase specific nucleic acid probe, or measurement of enzymatic activity. Alternatively, a lectin may be employed which binds to biosynthetic products of glycosyl transferase, for example, $E_4$-PHA lectin. In a further alternative, the nucleic acid may be operatively linked to a reporter gene; the expression levels of the glycoprotein-modifying glycosyl transferase are determined by measuring a signal correlated with the expression level of the reporter gene. The reporter gene may transcribed together with the nucleic acid(s) encoding said glycoprotein-modifying glycosyl transferase as a single mRNA molecule; their respective coding sequences may be linked either by an internal ribosome entry site (IRES) or by a cap-independent translation enhancer (CITE). The reporter gene may be translated together with at least one nucleic acid encoding said glycoprotein-modifying glycosyl transferase such that a single polypeptide chain is formed. The nucleic acid encoding the glycoprotein-modifying glycosyl transferase may be operatively linked to the reporter gene under the control of a single promoter, such that the nucleic acid encoding the glycoprotein-modifying glycosyl transferase and the reporter gene are transcribed into an RNA molecule which is alternatively spliced into two separate messenger RNA (mRNA) molecules; one of the resulting mRNAs is translated into said reporter protein, and the other is translated into said glycoprotein-modifying glycosyl transferase.

If several different nucleic acids encoding a glycoprotein-modifying glycosyl transferase are expressed, they may be arranged in such way that they are transcribed as one or as several mRNA molecules. If they are transcribed as single mRNA molecule, their respective coding sequences may be linked either by an internal ribosome entry site (IRES) or by a cap-independent translation enhancer (CITE). They may be transcribed from a single promoter into an RNA molecule which is alternatively spliced into several separate messenger RNA (mRNA) molecules, which then are each translated into their respective encoded glycoprotein-modifying glycosyl transferase.

1. Expression Systems

Methods which are well known to those skilled in the art can be used to construct expression vectors containing the coding sequence of the protein of interest and the coding sequence of the glycoprotein-modifying glycosyl transferase and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the coding sequence of the protein of interest and the coding sequence of the glycoprotein-modifying glycosyl transferase. Preferably, mammalian cells are used as host cell systems transfected with recombinant plasmid DNA or cosmid DNA expression vectors containing the coding sequence of the protein of interest and the coding sequence of the glycoprotein-modifying glycosyl transferase. Most preferably, CHO cells, BHK cells, NS0 cells, or SP2/0 cells, or alternatively, hybridoma cells are used as host cell systems. In alternate embodiments, other eukaryotic host cell systems may be contemplated, including, yeast cells transformed with recombinant yeast expression vectors containing the coding sequence of the protein of interest and the coding sequence of the glycoprotein-modifying glycosyl transferase; insect cell systems infected with recombinant virus expression vectors (e.g., baculovirus) containing the coding sequence of the protein of interest and the coding sequence of the glycoprotein-modifying glycosyl transferase; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of the protein of interest and the coding sequence of the glycoprotein-modifying glycosyl transferase; or animal cell systems infected with recombinant virus expression vectors (e.g., adenovirus, vaccinia virus) including cell lines engineered to contain multiple copies of the DNA encoding the protein of interest and the coding sequence of the glycoprotein-modifying glycosyl transferase either stably amplified (CHO/dhfr) or unstably amplified in double-minute chromosomes (e.g., murine cell lines).

For the methods of this invention, stable expression is generally preferred to transient expression because it typically achieves more reproducible results and also is more amenable to large scale production. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

A number of selection systems may be used, including, but not limited to, the herpes simplex virus thymidine kinase (Wigler et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy et al., 1980, *Cell* 22:817) genes, which can be employed in tk$^-$, hgprt$^-$ or aprt$^-$ cells, respectively. Also, antimetabolite resistance can be used as the basis of selection for dhfr, which confers resistance to methotrexate (Wigler et al., 1980, *Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin et al., 1981, *J. Mol. Biol.* 150: 1); and hygro, which confers resistance to hygromycin (Santerre et al., 1984, *Gene* 30:147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85:8047); the glutamine synthase system; and ODC (ornithine decarboxylase) which confers resistance to the ornithine decarboxylase inhibitor, 2-(difluoromethyl)-DL-ornithine, DFMO (McConlogue, 1987, in: Current Communications in Molecular Biology, Cold Spring Harbor Laboratory ed.).

2. Identification of Transfectants or Transformants that Express the Protein Having a Modified Glycosylation Pattern The host cells which contain the coding sequence and which express the biologically active gene products may be identified by at least four general approaches: (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

In the first approach, the presence of the coding sequence of the protein of interest and the coding sequence of the glycoprotein-modifying glycosyl transferase(s) inserted in the expression vector can be detected by DNA-DNA or DNA-RNA hybridization using probes comprising nucleotide sequences that are homologous to the respective coding sequences, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the coding sequence of the protein of interest and the coding sequence of the glycoprotein-modifying glycosyl transferase are inserted within a marker gene sequence of the vector, recombinants containing the respective coding sequences can be identified by the absence of the marker gene function. Alternatively, a marker gene can be placed in tandem with the coding sequences under the control of the same or different promoter used to control the expression of the coding sequences. Expression of the marker in response to induction or selection indicates expression of the coding sequence of the protein of interest and the coding sequence of the glycoprotein-modifying glycosyl transferase.

In the third approach, transcriptional activity for the coding region of the protein of interest and the coding sequence of the glycoprotein-modifying glycosyl transferase can be assessed by hybridization assays. For example, RNA can be isolated and analyzed by Northern blot using a probe homologous to the coding sequences of the protein of interest and the coding sequence of the glycoprotein-modifying glycosyl transferase or particular portions thereof. Alternatively, total nucleic acids of the host cell may be extracted and assayed for hybridization to such probes.

In the fourth approach, the expression of the protein products of the protein of interest and the coding sequence of the glycoprotein-modifying glycosyl transferase can be assessed immunologically, for example by Western blots, immunoassays such as radioimmuno-precipitation, enzyme-linked immunoassays and the like. The ultimate test of the success of the expression system, however, involves the detection of the biologically active gene products.

D. Generation and Use of Proteins and Protein Fragments Having Altered Glycosylation Patterns 1. Generation and use of Antibodies Having Enhanced Antibody-Dependent Cellular Cytotoxicity In preferred embodiments, the present invention provides glycoforms of antibodies and antibody fragments having an enhanced antibody-dependent cellular cytotoxicity.

Clinical trials of unconjugated monoclonal antibodies (mAbs) for the treatment of some types of cancer have recently yielded encouraging results. Dillman, 1997, *Cancer Biother. & Radiopharm.* 12:223-225; Deo et al., 1997, *Immunology Today* 18:127. A chimeric, unconjugated IgG1 has been approved for low-grade or follicular B-cell non-Hodgkin's lymphoma (Dillman, 1997, supra), while another unconjugated mAb, a humanized IgG1 targeting solid breast tumors, has also been showing promising results in phase III clinical trials. Deo et al., 1997, supra. The antigens of these two mAbs are highly expressed in their respective tumor cells and the antibodies mediate potent tumor destruction by effector cells in vitro and in vivo. In contrast, many other unconjugated mAbs with fine tumor specificities cannot trigger effector functions of sufficient potency to be clinically useful. Frost et al., 1997, *Cancer* 80:317-333; Surfus et al., 1996, *J. Immunother.* 19:184-191. For some of these weaker mAbs, adjunct cytokine therapy is currently being tested. Addition of cytokines can stimulate antibody-dependent cellular cytotoxicity (ADCC) by increasing the activity and number of circulating lymphocytes. Frost et al., 1997, supra; Surfus et al., 1996, supra. ADCC, a lytic attack on antibody-targeted cells, is triggered upon binding of lymphocyte receptors to the constant region (Fc) of antibodies. Deo et al., 1997, supra.

A different, but complementary, approach to increase ADCC activity of unconjugated IgG1s would be to engineer the Fc region of the antibody to increase its affinity for the lymphocyte receptors (FcγRs). Protein engineering studies have shown that FcγRs interact with the lower hinge region of the IgG CH2 domain. Lund et al., 1996, *J. Immunol.* 157: 4963-4969. However, FcγR binding also requires the presence of oligosaccharides covalently attached at the conserved Asn 297 in the CH2 region. Lund et al., 1996, supra; Wright and Morrison, 1997, *Tibtech* 15:26-31, suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction.

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., 1997, *Biochemistry* 36:130-1380), with low level of terminal sialic acid and bisecting N-acetylglucosamine (GlcNAc), and a variable degree of terminal galactosylation and core fucosylation (FIG. 1). Some studies suggest that the minimal carbohydrate structure required for FcγR binding lies within the oligosaccharide core. Lund et al., 1996, supra. The removal of terminal galactoses results in approximately a two-fold reduction in ADCC activity, indicating a role for these residues in FcγR receptor binding. Lund et al., 1996, supra.

The mouse- or hamster-derived cell lines used in industry and academia for production of unconjugated therapeutic mAbs normally attach the required oligosaccharide determinants to Fc sites. IgGs expressed in these cell lines lack, however, the bisecting GlcNAc found in low amounts in serum IgGs. Lifely et al., 1995, *Glycobiology* 318:813-822. In contrast, it was recently observed that a rat myeloma-produced, humanized IgG1 (CAMPATH-1H) carried a bisecting GlcNAc in some of its glycoforms. Lifely et al., 1995, supra. The rat cell-derived antibody reached a similar in vitro ADCC activity as CAMPATH-1H antibodies produced in standard cell lines, but at significantly lower antibody concentrations.

The CAMPATH antigen is normally present at high levels on lymphoma cells, and this chimeric mAb has high ADCC activity in the absence of a bisecting GlcNAc. Lifely et al., 1995, supra. Even though in the study of Lifely et al., 1995, supra. the maximal in vitro ADCC activity was not increased by altering the glycosylation pattern, the fact that this level of activity was obtained at relatively low antibody concentrations for the antibody carrying bisected oligosaccharides suggests an important role for bisected oligosaccharides. An approach was developed to increase the ADCC activity of IgG1s with low basal activity levels by producing glycoforms of these antibodies carrying bisected oligosaccharides in the Fc region.

In the N-linked glycosylation pathway, a bisecting GlcNAc is added by the enzyme β(1,4)-N-acetylglucosaminyltransferase III (GnT III). Schachter, 1986, *Biochem. Cell Biol.* 64:163-181. Lifely et al., 1995, supra, obtained different glycosylation patterns of the same antibody by producing the antibody in different cell lines with different but non-engineered glycosylation machineries, including a rat myeloma cell line that expressed GnT III at an endogenous, constant level. In contrast, we used a single antibody-producing CHO cell line, that was previously engineered to express, in an externally-regulated fashion, different levels of a cloned GnT III gene. This approach allowed us to establish for the first time a rigorous correlation between expression of GnT III and the ADCC activity of the modified antibody.

As demonstrated herein, see, Example 4, infra, C2B8 antibody modified according to the disclosed method had an about sixteen-fold higher ADCC activity than the standard, unmodified C2B8 antibody produced under identical cell culture and purification conditions. Briefly, a C2B8 antibody sample expressed in CHO-tTA-C2B8 cells that do not have GnT III expression showed a cytotoxic activity of about 31% (at 1 μg/ml antibody concentration), measured as in vitro lysis of SB cells (CD20+) by human lymphocytes. In contrast, C2B8 antibody derived from a CHO cell culture expressing GnT III at a basal, largely repressed level showed at 1 μg/ml antibody concentration a 33% increase in ADCC activity against the control at the same antibody concentration. Moreover, increasing the expression of GnT III produced a large increase of almost 80% in the maximal ADCC activity (at 1 μg/ml antibody concentration) compared to the control at the same antibody concentration. See, Example 4, infra.

Further antibodies of the invention having an enhanced antibody-dependent cellular cytotoxicity include, but are not limited to, anti-human neuroblastoma monoclonal antibody (chCE7) produced by the methods of the invention, a chimeric anti-human renal cell carcinoma monoclonal antibody (ch-G250) produced by the methods of the invention, a humanized anti-HER2 monoclonal antibody produced by the methods of the invention, a chimeric anti-human colon, lung, and breast carcinoma monoclonal antibody (ING-1) produced by the methods of the invention, a humanized anti-human 17-1A antigen monoclonal antibody (3622W94) produced by the methods of the invention, a humanized anti-human colorectal tumor antibody (A33) produced by the methods of the invention, an anti-human melanoma antibody (R24) directed against GD3 ganglioside produced by the methods of the invention, and a chimeric anti-human squamous-cell carcinoma monoclonal antibody (SF-25) produced by the methods of the invention. In addition, the invention is directed to antibody fragment and fusion proteins comprising a region that is equivalent to the Fc region of immunoglobulins. See, infra.

2. Generation and use of Fusion Proteins Comprising a Region Equivalent to an Fc Region of an Immunoglobulin that Promote Fc-Mediated Cytotoxicity As discussed above, the present invention relates to a method for enhancing the ADCC activity of therapeutic antibodies. This is achieved by engineering the glycosylation pattern of the Fc region of such antibodies, in particular by maximizing the proportion of antibody molecules carrying bisected complex oligosaccharides N-linked to the conserved glycosylation sites in their Fc regions. This strategy can be applied to enhance Fc-mediated cellular cytotoxicity against undesirable cells mediated by any molecule carrying a region that is an equivalent to the Fc region of an immunoglobulin, not only by therapeutic antibodies, since the changes introduced by the engineering of glycosylation affect only the Fc region and therefore its interactions with the Fc receptors on the surface of effector cells involved in the ADCC mechanism. Fc-containing molecules to which the presently disclosed methods can be applied include, but are not limited to, (a) soluble fusion proteins made of a targeting protein domain fused to the N-terminus of an Fc-region (Chamov and Ashkenazi, 1996, *TIBTECH* 14: 52) and (b) plasma membrane-anchored fusion proteins made of a type II transmembrane domain that localizes to the plasma membrane fused to the N-terminus of an Fc region (Stabila, P. F., 1998, *Nature Biotech.* 16: 1357).

In the case of soluble fusion proteins (a) the targeting domain directs binding of the fusion protein to undesirable cells such as cancer cells, i.e., in an analogous fashion to therapeutic antibodies. The application of presently disclosed method to enhance the Fc-mediated cellular cytotoxic activity mediated by these molecules would therefore be identical to the method applied to therapeutic antibodies. See, Example 2 of U.S. Provisional Application Ser. No. 60/082,581, incorporated herein by reference.

In the case of membrane-anchored fusion proteins (b) the undesirable cells in the body have to express the gene encoding the fusion protein. This can be achieved either by gene therapy approaches, i e., by transfecting the cells in vivo with a plasmid or viral vector that directs expression of the fusion protein-encoding gene to undesirable cells, or by implantation in the body of cells genetically engineered to express the fusion protein on their surface. The later cells would normally be implanted in the body inside a polymer capsule (encapsulated cell therapy) where they cannot be destroyed by an Fc-mediated cellular cytotoxicity mechanism. However should the capsule device fail and the escaping cells become undesirable, then they can be eliminated by Fc-mediated cellular cytotoxicity. Stabila et al., 1998, *Nature Biotech.* 16: 1357. In this case, the presently disclosed method would be applied either by incorporating into the gene therapy vector an additional gene expression cassette directing adequate or optimal expression levels of GnT III or by engineering the cells to be implanted to express adequate or optimal levels of GnT III. In both cases, the aim of the disclosed method is to increase or maximize the proportion of surface-displayed Fc regions carrying bisected complex oligosaccharides.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VIII. EXAMPLES

A. Example 1

Tetracycline-Regulated Overexpression of Glycosyl Transferases in Chinese Hamster Ovary Cells To establish a cell line in which the expression of GnT III could be externally-controlled, a tetracycline-regulated expression system was used. Gossen, M. and Bujard, H., 1992, *Proc. Nat. Acad. Sci. USA,* 89: 5547-5551. The amount of GnT III in these cells could be controlled simply by manipulating the concentration of tetracycline in the culture medium. Using this system, it was found that overexpression of GnT III to high levels led to growth inhibition and was toxic to the cells. Another CHO cell line with tetracycline-regulated overexpression of GnT V, a distinct glycoprotein-modifying glycosyl transferase, showed the same inhibitory effect, indicating that this may be a general feature of glycoprotein-modifying glycosyl transferase overexpression. This phenomenon has not been reported previously, probably due to the fact that inventigators generally have used constitutive promoters for related experiments. The growth effect sets an upper limit to the level of glycoprotein-modifying glycosyl transferase overexpression, and may thereby also limit the maximum extent of modification of poorly accessible glycosylation sites.

1. Materials and Methods

Establishment Of CHO Cells With Tetracycline-Regulated Expression Of Glycosyltransferases. In a first step, an intermediate CHO cell line (CHO-tTA) was first generated that constitutively expresses a tetracycline-controlled transactivator (tTA) at a level for the adequate for the regulation system. Using Lipofectamine reagent (Gibco, Eggenfelden, Germany), CHO (DUKX) cells were co-transfected, with pUHD15-1, a vector for constitutive expression of the tTA gene (Gossen and Bujard, 1992, *Proc. Nat. Acad. Sci. USA,* 89: 5547-5551), and pSV2Neo, a vector for constitutive expression of a neomycin resistance gene (Clontech, Palo Alto, Calif.). Stable, drug-resistant clones were selected and screened for adequate levels of tTA expression via transient transfections with a tetracycline-regulated β-galactosidase expression vector, pUHG16-3. C-myc epitope-encoding DNA was added to the 3' end of the rat GnT III cDNA (Nishikawa et al., 1992, *J. Biol. Chem.* 267:18199-18204) by PCR amplification. Nilsson et al; 1993, *J. Cell Biol.* 120:5-13. The product was sequenced and subcloned into pUHD10-3, a vector for tetracycline-regulated expression (Gossen and Bujard, supra) to generate the vectorpUHD10-3-GnTIIIm. The human GnT V cDNA (Saito et al., 1995, *Eur. J. Biochem.* 233:18-26), was directly subcloned into pUHD10-3 to generate plasmid vectorpUHD10-3-GnT V. CHO-tTA cells were co-transfected using a calcium phosphate transfection method (Jordan and Wurm, 1996, Nucleic Acids Res. 24:596-601), with pPur, a vector for constitutive expression of puromycin resistance (Clontech, Palo Alto, Calif.), and either the vector pUHD10-3-GnT IIIm or the vector pUHD10-3-GnT V. Puromycin resistant clones were selected in the presence of tetracycline, isolated and then analyzed for tetracycline-regulated expression of GnT III or GnT V via western blots analysis. See, infra.

Western And Lectin Blotting. For Western blot analysis of GnT III or GnT V, cell lysates were separated by SDS-PAGE and electroblotted to PVDF membranes (Millipore, Bedford, Mass.). GnT III was detected using the anti-c-myc monoclonal antibody 9E10 (Nilsson et al., 1993, *J. Cell Biol.* 120: 5-13) and GnT V using with an anti-GnT V rabbit polyclonal antibody (Chen et al., 1995, *Glycoconjugate J.* 12:813-823). Anti-mouse or anti-rabbit IgG-horse radish peroxidase (Amersham, Arlington, Ill.) was used as secondary antibody. Bound secondary antibody was detected using an enhanced chemiluminescence kit (ECL kit, Amershamn, Arlington, Ill.)

For lectin blot analysis of glycoproteins modified either by GnT III- or GnT V-catalyzed reactions, biotinylated E-PHA (Oxford Glycosciences, Oxford, United Kingdom) or L-PHA-digoxigenin (Boehringer Mannheim, Mannheim, Germany), respectively, were used. Merkle and Cummings, 1987, *Methods Enzymol.* 138:232-259.

2. Results And Discussion

Establishment Of CHO Cell Lines With Tetracycline-Regulated Overexpression Of Glycosyl Transferases. The strategy used for establishment of glycosyl transferase overexpressing cell lines consisted of first generating an intermediate CHO cell line constitutively expressing the tetracycline-controlled transactivator (tTA) at an adequate level for the system to work. Yin et al., 1996, *Anal. Biochem.* 235:195-201. This level had to be high enough to activate high levels of transcription, in the absence of tetracycline, from the minimal promoter upstream of the glycosyl transferase genes. CHO cells were co-transfected with a vector for constitutive expression for tTA, driven by the human cytomegalovirus (hCMV) promoter/enhancer, and a vector for expression of a neomycin-resistance ($Neo^R$) gene. An excess of the tTA-expression vector was used and neomycin-resistant clones were isolated.

In mammalian cells, co-transfected DNA integrates adjacently at random locations within the chromosomes, and expression depends to a large extent on the site of integration and also on the number of copies of intact expression cassettes. A mixed population of clones with different expression levels of the transfected genes is generated. Yin et al., 1996, supra. Selection for neomycin resistance merely selects for integration of an intact $Neo^R$ expression cassette, while the use of an excess of the tTA-expression vector increases the probability of finding clones with good expression of tTA. The mixed population of clones has to be screened using a functional assay for tTA expression. Gossen and Bujard, 1992, supra; Yin et al., 1996, supra. This was done by transfection of each clone with a second vector harboring a reporter gene, lacZ, under the control of the tet-promoter and screening for tetracycline-regulated (tet-regulated), transient expression (i.e., one to three days after transfection) of B-galactosidase activity. CHOt17, which showed the highest level of tet-regulated 13-galactosidase activity among twenty screened clones, was selected for further work.

CHOt17 cells were tested for tet-regulated expression of GnT III by transfecting the cells with vector pUHD10-3-GnT IIIm and comparing the relative levels of GnT III after incubation of the cells in the presence and absence of tetracycline for 36 h. GnT III levels were compared by western blot analysis, using a monoclonal antibody (9E 10) which recognizes the c-myc peptide epitope tag at the carboxy-terminus of GnT III. The tag had been introduced through a modification of the glycosyl transferase gene using PCR amplification. Various reports have demonstrated addition of peptide epitope tags to the carboxy-termini of glycosyl transferases, a group of enzymes sharing the same topology, without disruption of localization or activity. Nilsson et al., 1993, supra; Rabouille et al., 1995, *J Cell Science* 108:1617-1627. FIG. 2 shows that in clone CHOt17 GnT III accumulation is significantly higher in the absence than in the presence of tetracycline. An additional clone, CHOt2, which gave weaker activation of transcription in the b-galactosidase activity assay, was tested in parallel (FIG. 2). GnT III and β-galactosidase expression levels follow the same pattern of tetracycline-regulation for both of these clones. The range of tetracycline concentrations where GnT III expression can be quantitatively controlled was found to be from 0 to 100 ng/ml (FIG. 3). This result agrees with previous research using different cell lines and genes (Yin et al., 1996, supra).

To generate a stable cell line with tet-regulated expression of GnT III, CHOt17 cells were co-transfected with vector pUHD10-3-GnT IIIm and vector, pPUR, for expression of a puromycin resistance gene. In parallel, CHOt17 cells were co-transfected with pUHD10-3-GnT V and pPUR vectors to generate an analogous cell line for this other glycosyl transferase. A highly efficient calcium phosphate transfection method was used and the DNA was linearized at unique restriction sites outside the eucaryotic expression cassettes, to decrease the probability of disrupting these upon integration. By using a host in which the levels of tTA expressed had first been proven to be adequate, the probability of finding clones with high expression of the glycosyl transferases in the absence of tetracycline is increased.

Stable integrants were selected by puromycin resistance, keeping tetracycline in the medium throughout clone selection to maintain glycosyl transferase expression at basal levels. For each glycosyl transferase, sixteen puromycin resistant clones were grown in the presence and absence of tetracycline, and eight of each were analysed by western blot analysis (FIG. 4). The majority of the clones showed good regulation of glycosyl transferase expression. One of the GnT III-expressing clones showed a relatively high basal level in the presence of tetracycline (FIG. 4B, clone 3), which suggests integration of the expression cassete close to an endogenous CHO-cell enhancer; while two puromycin-resistant clones showed no expression of GnT III in the absence of tetracycline (FIG. 4B, clones 6 and 8). Among the clones showing good regulation of expression, different maximal levels of glycosyl transferase were observed. This may be due to variations in the site of integration or number of copies integrated. Activity of the glycosyl transferases was verified by E-PHA and L-PHA lectin binding to endogenous cellular glycoproteins derived from various clones grown in the presence and absence of tetracycline (FIG. 5). Lectins are proteins which bind to specific oligosaccharide structures. E-PHA lectin binds to bisected oligosaccharides, the products of GnT III-catalyzed reactions, and L-PHA binds to tri- and tetra-antennary oligosaccharides produced by GnT V-catalyzed reactions (Merkle and Cummings, 1987, *Methods Enzymol.* 138:232-259). For each glycosyl transferase, a clone with high expression in the absence, but with undetectable expression in the presence, of tetracycline (clone 6, FIG. 4A, CHO-tet-GnT V, and clone 4, FIG. 4B, CHO-tet-GnT IIIm) was selected for further work.

B. Example 2

Inhibition of Cell Growth Effected by Glycosyl Transferase Overexpresseion

During screening of GnT III- and GnT V-expressing clones in the absence of tetracycline, see, Example 1, supra, approximately half of each set of clones showed a strong inhibition of growth. The extent of growth-inhibition varied among clones, and comparison with expression levels estimated from western blot analysis (FIG. 4) suggested a correlation between the degree of growth-inhibition and glycosyl transferase overexpression. This correlation was firmly established by growing the final clones, CHO-tet-GnT IIIm and CHO-tet-GnT V, in different concentrations of tetracycline. A strong inhibition of growth was evident after two days of culture at low levels of tetracycline (FIG. 6). Growth-inhibited cells displayed a small, rounded morphology instead of the typical extended shape of adherent CHO cells. After a few days, significant cell death was apparent from the morphology of the growth-inhibited cells.

Growth-inhibition due to glycosyl transferase overexpression has not hitherto been reported in the literature, probably due to the widespread use of constitutive promoters. Those clones giving constitutive expression of a glycosyl transferase at growth-inhibiting levels, would be lost during the selection procedure. This was avoided here by keeping tetracycline in the medium, i.e., basal expression levels, throughout selection. Prior to selection, the frequency of clones capable of expressing glycosyl transferases to growth-inhibiting levels using traditional mammalian vectors based on the constitutive hCMV promoter/enhancer would be expected to be lower. This is due to the fact that, for any given gene, the pUHD10-3 vector in CHO cell lines selected for high constitutive levels of tTA, gives significantly higher expression levels than constitutive hCMV promoter/enhancer-based vectors, as observed by others. Yin et al., 1996, supra.

Inhibition of cell growth could be due to a direct effect of overexpression of membrane-anchored, Golgi-resident glycosyl transferases independent of their in vivo catalytic activity, e.g., via misfolding in the endoplasmic reticulum (ER) causing saturation of elements which assist protein folding in the ER. This could possibly affect the folding and secretion of other essential cellular proteins. Alternatively, inhibition of growth could be related to increased in vivo activity of the glycosyl transferase leading to a change of the glycosylation pattern, in a function-disrupting fashion, of a set of endogenous glycoproteins necessary for growth under standard in vitro culture conditions.

Independent of the underlying mechanism, the growth-inhibition effect has two consequences for engineering the glycosylation of animal cells. First, it implies that cotransfection of constitutive glycosyl transferase expression vectors together with vectors for the target glycoprotein product is a poor strategy. Other ways of linking expression of these two classes of proteins, e.g., through the use of multiple constitutive promoters of similar strength or use of multicistronic, constitutive expression vectors, should also be avoided. In these cases, clones with very high, constitutive expression of the target glycoprotein, a pre-requisite for an economical bioprocess, would also have high expression of the glycosyl transferase and would be eliminated during the selection process. Linked, inducible expression could also be problematic for industrial bioprocesses, since the viability of the growth-arrested cells would be compromised by the overexpression of the glycosyl transferase.

The second consequence is that it imposes an upper limit on glycosyl transferase overexpression for glycosylation engineering approaches. Clearly, the conversions of many glycosyl transferase-catalyzed reactions in the cell, at the endogenous levels of glycosyl transferases, are very high for several glycosylation sites. However, glycosylation sites where the oligosaccharides are somewhat inaccesible or are stabilized in unfavorable conformations for specific glycosyl tranferases also exist. For example, it has been observed that addition of bisecting GlcNAc is more restricted to the oligosaccharides attached to the Fc region than to those located on the variable regions of human IgG antibodies. Savvidou et al., 1984, *Biochemistry* 23:3736-3740. Glycosylation engineering of these restricted sites could be affected by such a limit on glycosyl transferase expression. Although this would imply aiming for an "unnatural" distribution of glycoforms, these could be of benefit for special therapeutic applications of glycoproteins.

C. Example 3

Engineering The Glycosylation of an Anti-Human Neuroblastoma Antibody in Chinese Hamster Ovary Cells In order to validate the concept of engineering a therapeutic antibody by modifying its glycosylation pattern, a chimeric anti-human neuroblastoma IgG1 (chCE7) was chosen which has insignificant ADCC activity when produced by SP2/0 recombinant mouse myeloma cells. ChCE7 recognizes a tumor-associated 190-kDa membrane glycoprotein and reacts strongly with all neuroblastoma tumors tested to date. It has a high affinity for its antigen ($K_d$ of $10^{10}M^{-1}$) and, because of its high tumor-specificity, it is routinely used as a diagnostic tool in clinical pathology. Amstutz et al., 1993, *Int. J. Cancer* 53:147-152. In recent studies, radiolabelled chCE7 has shown good tumor localization in human patients. Durr, 1993, *Eur. J. Nucl. Med.* 20:858. The glycosylation pattern of chCE7, an anti-neuroblastoma therapeutic monoclonal antibody (mAb) was engineered in CHO cells with tetracycline-regulated expression of GnT III. A set of mAb samples differing in their glycoform distribution was produced by controlling GnT III expression in a range between basal and toxic levels, and their glycosylation profiles were analyzed by MALDI/TOF-MS of neutral oligosaccharides. Measurement of the ADCC activity of these samples showed an optimal range of GnT III expression for maximal chCE7 in vitro biological activity, and this activity correlated with the level of Fc-associated bisected, complex oligosaccharides.

1. Materials and Methods

Construction Of chCE7 Expression Vectors. Plasmid vectors 10CE7VH and 98CE7VL, for expression of heavy (IgG1) and light (kappa) chains, respectively, of anti-human neuroblastoma chimeric antibody chCE7, which contain chimeric genomic DNA including the mouse immunoglobulin promoter/enhancer, mouse antibody variable regions, and human antibody constant regions (Amstutz et al., 1993, *Int. J. Cancer* 53:147-152) were used as starting materials for the construction of the final expression vectors, pchCE7H and pchCE7L. Chimeric heavy and light chain chCE7 genes were reassambled and subcloned into the pcDNA3.1 (+) vector. During reassembly, all introns were removed, the leader sequences were replaced with synthetic ones, Reffet al., 1994, *Blood* 83:435-445, and unique restriction sites joining the variable and constant region sequences were introduced. Introns from the heavy constant region were removed by splicing with overlap-extension-PCR. Clackson et al., 1991, General Applications of PCR to Gene Cloning and Manipulation, p. 187-214, in: McPherson et al. (ed.), *PCR a Practical Approach*, Oxford University Press, Oxford.

Production Of chCE7 In CHO Cells Expressing Different Levels Of GnT III. CHO-tet-GnT IIIm (see, supra) cells were co-transfected with vectors pchCE7H, pchCE7L, and pZeoSV2 (for Zeocin resistance, Invitrogen, Groningen, The Netherlands) using a calcium phosphate transfection method. Zeocin resistant clones were transferred to a 96-well cell culture plate and assayed for chimeric antibody expression using an ELISA assay specific for human IgG constant region. Lifely et al; 1995, supra. Four chCE7 antibody samples were derived from parallel cultures of a selected clone (CHO-tet-GnT IIIm-chCE7), grown in FMX-8 cell culture medium supplemented with 10% FCS; each culture containing a different level of tetracycline and therefore expressing GnT III at different levels. CHO-tet-GnT IIIm-chCE7 cells were expanded and preadapted to a different concentration of tetracycline during 7 days. The levels of tetracycline were 2000, 60, 30, and 15 ng/ml.

Purification Of chCE7Antibody Samples. Antibody was purified from culture medium by Protein A affinity chromatography on a 1 ml HiTrap Protein A column (Pharmacia Biotech, Uppsala, Sweden), using linear pH gradient elution from 20 mM sodium phosphate, 20 mM sodium citrate, 500 mM sodium chloride, 0.01% Tween 20, 1M urea, pH 7.5 (buffer A) to buffer B (buffer A without sodium phosphate, pH 2.5). Affinity purified chCE7 samples were buffer exchanged to PBS on a 1 ml ResourceS cation exchange column (Pharmacia Biotech, Uppsala, Sweden). Final purity was judged to be higher than 95% from SDS-PAGE and Coomasie-Blue staining. The concentration of each sample was estimated from the absorbance at 280 nm.

Binding Of Antibodies To Neuroblastoma Cells. Binding affinity to human neuroblastoma cells was estimated from displacement of $^{125}$I-labeled chCE7 by the CHO-produced samples. Amstutz et al; 1993, supra.

Oligosaccharide Analysis By MALDI/TOF-MS. CE7-2000t, -60t, -30t, and -15t samples were treated with *A. urefaciens* sialidase (Oxford Glycosciences, Oxford, United Kingdom), following the manufacturer's instructions, to remove any sialic acid monosaccharide residues. The sialidase digests were then treated with peptide N-glycosidase F (PNGaseF, Oxford Glycosciences, Oxford, United Kingdom), following the manufacturer's instructions, to release the N-linked oligosaccharides. Protein, detergents, and salts were removed by passing the digests through microcolumns containing, from top to bottom, 20 ml of SepPak C18 reverse phase matrix (Waters, Milford, Mass.), 20 ml of Dowex AG 50W X8 cation exchange matrix (BioRad, Hercules, Calif.), and 20 ml of AG 4×4 anion exchange matrix (BioRad, Hercules, Calif.). The microcolumns were made by packing the matrices in a Gel Loader tip (Eppendorf, Basel, Switzerland) filled with ethanol, followed by an equilibration with water. Kütster et al., 1997, *Anal. Biochem.* 250:82-101. Flow through liquid and a 300 ml-water wash were pooled, filtered, evaporated to dryness at room temperature, and resuspended in 2 ml of deionized water. One microliter was applied to a MALDI-MS sample plate (Perseptive Biosystems, Farmingham, Mass.) and mixed with 1 ml of a 10 mg/ml dehydrobenzoic acid (DHB, Aldrich, Milwaukee, Wis.) solution in acetonitrile. The samples were air dried and the resulting crystals were dissolved in 0.2 ml of ethanol and allowed to recrystallize by air drying. Harvey, 1993, *Rapid Mass. Spectrom.* 7:614-619. The oligosaccharide samples were then analyzed by matrix-assisted laser desorption ionization/time-of-flight-mass spectrometry (MALDI/TOF-MS) using an Elite Voyager 400 spectrometer (Perseptive Biosystems, Farmingham, Mass.), equipped with a delayed ion extraction MALDI-ion source, in positive ion and reflector modes, with an accelaration voltage of 20 kV. One hundred and twenty eight scans were averaged. Bisected biantennary complex oligosaccharide structures were assigned to five-HexNAc-associated peaks. Non-bisected tri-antennary N-linked oligosaccharides, the alternative five HexNAc-containing isomers, have never been found in the Fc region of IgGs and their syntheses are catalyzed by glycosyltransferases discrete from GnT III.

ADCC Activity Assay. Lysis of IMR-32 human neuroblastoma cells (target) by human lymphocytes (effector), at a target:effector ratio of 1:19, during a 16 h incubation at 37° C. in the presence of different concentrations of chCE7 samples, was measured via retention of a fluorescent dye. Kolber et al; 1988, *J. Immunol. Methods* 108: 255-264. IMR-32 cells were labeled with the fluorescent dye Calcein AM for 20 min (final concentration 3.3 µM). The labeled cells (80,000 cells/well) were incubated for 1 h with different concentrations of CE7 antibody. Then, monocyte depleted mononuclear cells were added (1,500,000 cells/well) and the cell mixture was incubated for 16 h at 37° C. in a 5% $CO_2$ atmosphere. The supernatant was discarded and the cells were washed once with HBSS and lysed in Triton X-100 (0.1%). Retention of the fluorescent dye in IMR-32 cells was measured with a fluorometer (Perkin Elmer, Luminscence Spectrometer LS 50B, (Foster City, Calif.) and specific lysis was calculated relative to a total lysis control, resulting from exposure of the target to a detergent instead of exposure to antibody. The signal in the absence of antibody was set to 0% cytotoxicity. Each antibody concentration was analyzed by triplicate, and the assay was repeated three separate times.

2. Results and Discussion

Production Of chCE7 In CHO Cells Expressing Different Levels Of GnT III. ChCE7 heavy and light chain expression vectors were constructed incorporating the human cytomegalovirus (hCMV) promoter, the bovine growth hormone termination and polyadenylation sequences, and eliminating all heavy and light chain introns. This vector design was based on reports of reproducible high-level expression of recombinant IgG genes in CHO cells. Reff et al; 1994, supra; Trill et al., 1995, *Current Opinion Biotechnol.* 6:553-560. In addition, a unique restriction sites was introduced in each chain, at the junction between the variable and constant regions. These sites conserve the reading frame and do not change the amino acid sequence. They should enable simple exchange of the mouse variable regions, for the production of other mouse-human chimeric antibodies. Reff et al., 1994, supra. DNA sequencing confirmed that the desired genes were appropriately assembled, and production of the chimeric antibody in transfected CHO cells was verified with a human Fc-ELISA assay.

CHO-tet-GnT IIIm-chCE7 cells, with stable, tetracycline-regulated expression of GnT III and stable, constitutive expression of chCE7, were established and scaled-up for production of a set of chCE7 samples. During scale-up, four parallel cultures derived from the same CHO clone were grown, each at a different level of tetracycline and therefore only differing in the level of expression of the GnT III gene. This procedure eliminates any clonal effects from other variables affecting N-linked glycoform biosynthesis, permitting a rigorous correlation to be established between GnT III gene expression and biological activity of the glycosylated antibody. The tetracycline concentration ranged from 2000 ng/ml, i.e., the basal level of GnT III expression, to 15 ng/ml, at which significant growth inhibition and toxicity due to glycosyl transferase overexpression was observed (see, supra). Indeed, only a small amount of antibody could be recovered from the latter culture. The second highest level of GnT III expression, using tetracycline at a concentration of 30 ng/ml, produced only a mild inhibition of growth. The purified antibody yield from this culture was approximately 70% that from the remaining two lower levels of GnT III gene overexpression.

The four antibody samples, CE7-2000t, -60t, -30t, and -15t, numbers denoting the associated concentration of tetracycline, were purified by affinity chromatography on Protein A and buffer exchanged to PBS using a cation exchange column. Purity was higher than 95% as judged from SDS-PAGE with Coomassie Blue staining. Binding assays to human neuroblastoma cells revealed high affinity to the cells and no significant differences in antigen binding among the different samples (estimated equilibrium dissociation constants varied between 2.0 and $2.7 \times 10^{-10}$ M). This was as expected, since there are no potential N-linked glycosylation sites in the CE7 variable regions.

Oligosaccharide Distributions And Levels Of Bisected Complex Oligosaccharides Of Different chCE7 Samples. Oligosaccharide profiles were obtained by matrix-assisted laser desorption/ionization mass spectrometry on a time-of-flight instrument (MALDI/TOF-MS). Mixtures of neutral N-linked oligosaccharides derived from each of the four CHO-produced antibody samples and from a SP2/0 mouse myeloma-derived chCE7 (CE7-SP2/0) sample were analyzed using 2,5-dehydrobenzoic acid (2,5-DHB) as the matrix (FIG. 9). Under these conditions, neutral oligosaccharides appear essentially as single [M+Na$^+$] ions, which are sometimes accompanied by smaller [M+K$^+$] ions, depending on the potassium content of the matrix. Bergweffet al., 1995, *Glycoconjugate J.* 12:318-330.

This type of analysis yields both the relative proportions of neutral oligosaccharides of different mass, reflected by relative peak height, and the isobaric monosaccharide composition of each peak. Küster et al., 1997, supra; Naven and Harvey, 1996, *Rapid Commun. Mass Spectrom.* 10:1361-1366. Tentative structures are assigned to peaks based on the monosaccharide composition, knowledge of the biosynthetic pathway, and on previous structural data for oligosaccharides derived from the same glycoprotein produced by the same host, since the protein backbone and the cell type can have a strong influence on the oligosaccharide distribution. Field et al., 1996, *Anal. Biochem.* 239:92-98. In the case of Fc-associated oligosaccharides, only bi-antennary complex oligosaccharides have been detected in IgGs present in human serum or produced by mammalian cell cultures under normal conditions. Wormald et al., 1997, *Biochemistry* 36:1370-1380; Wright and Morrison, 1997, *Tibtech* 15:26-31. The pathway leading to these compounds is illustrated in FIG. 10, including the mass of the [M+Na$^+$] ion corresponding to each oligosaccharide. High mannose oligosaccharides have also been detected on antibodies produced in the stationary and death phases of batch cell cultures. Yu Ip et al., 1994, *Arch. Biochem. Biophys.* 308:387-399.

The two major peaks in the CE7-SP2/0 sample (FIG. 9A) correspond to masses of fucosylated oligosaccharides with four N-acetylhexosamines (HexNAcs) containing either three (m/z 1486) or four (m/z 1648) hexoses. See, FIG. 10, but note that the summarized notation for oligosaccharides in this figure does not count the two GlcNAcs of the core. This composition is consistent with core fucosylated, bi-antennary complex oligosaccharide structures carrying zero or one galactose residues, respectively, typical of Fc-associated oligosaccharides, and as previously observed in NMR analysis of Fc oligosaccharides derived from a chimeric IgG1 expressed in SP2/0 cells. Bergwerffetal., 1995, supra.

GnT III-catalyzed transfer of a bisecting GlcNAc to these bi-antennary compounds, which are the preferred GnT III acceptors, would lead to oligosaccharides with five HexNAcs (m/z 1689 and 1851, non- and mono-galactosylated, respectively, FIG. 10), which are clearly absent in the CE7-SP2/0 sample. The latter peaks appear when chCE7 is expressed in CHO-tet-GnTIIIm cells. In the CHO-expressed antibodies the four HexNAc-containing peaks are also mainly fucosylated, although a small amount of non-fucosylated structures is evident from the peak at m/z 1339 (see, FIG. 10). The level of galactosylation is also not very different between the CHO- and SP2/0-derived material. At the basal level of GnT III expression (CE7-2000t sample, FIG. 9B), the molecules with five HexNAcs are present in a lower proportion than those with four HexNAcs. A higher level of GnT III expression (CE7-60t sample, FIG. 9C) led to a reversal of the proportions in favor of oligosaccharides with five HexNAcs. Based on this trend, bisected, bi-antennary complex oligosaccharide structures can be assigned to compounds with five HexNAcs in these samples. Tri-antennary N-linked oligosaccharides, the alternative five HexNAc-containing isomers, have never been found in the Fc region of IgGs and their syntheses are catalyzed by GlcNAc-transferases discrete from GnT III.

A further increase in GnT III expression (CE7-30t sample, FIG. 9D) did not lead to any significant change in the levels of bisected complex oligosaccharides. Another peak (m/z 1543) containing five HexNAcs appears at low, but relatively constant levels in the CHO-GnTIII samples and corresponds in mass to a non-fucosylated, bisected-complex oligosaccharide mass (FIG. 10). The smaller peaks at m/z 1705 and 1867, also correspond to five HexNAc-containing bi-antennary complex oligosaccharides. They can be assigned either to potassium adducts of the peaks at m/z 1689 and 1851 (mass difference of 16 Da with respect to sodium adducts) (Küster et al; 1997, supra) or to mono- and bi-galactosylated, bisected complex oligosaccharides without fucose (FIG. 10). Together, the bisected complex oligosaccharides amount to approximately 25% of the total in sample CE7-2000t and reach approximately 45 to 50% in samples CE7-60t and CE7-30t.

Additional information From The Oligosaccharide Profiles Of chCE7 Samples. Although the levels of bisected complex oligosaccharides were not higher in sample CE730t, increased overexpression of GnT III did continue to reduce, albeit to a small extent, the proportions of substrate bi-antennary complex oligosaccharide substrates. This was accompanied by moderate increases in two different, four HexNAc-containing peaks (m/z 1664 and 1810). The latter two peaks can correspond either to galactosylated bi-antennary complex oligosaccharides or to bisected hybrid compounds (FIG. 11). A combination of both classes of structures is also possible. The relative increase in these peaks is consistent with the accumulation of bisected hybrid by-products of GnT III overexpression. Indeed, the sample produced at the highest level of GnT III overexpression, CE7-15t, showed a large increase in the peak at m/z 1664, a reduction in the peak at m/z 1810 and a concomitant reduction of complex bisected oligosaccharides to a level of approximately 25%. See, peaks with m/z 1689 and 1851 in FIG. 9E and the corresponding structures in FIG. 11. Higher accumulation of non-fucosylated (m/z 1664) bisected hybrid by-products, instead of fucosylated ones (m/z 1810), would agree with the fact that oligosaccharides which are first modified by GnT III can no longer be biosynthetic substrates for core α1,6-fucosyltransferase. Schachter, 1986, *Biochem. Cell Biol.* 64:163-181.

The peak at m/z 1257 is present at a level of 10-15% of the total in the CHO-derived samples and at a lower level in CE7-SP2/0 (FIG. 9). It corresponds to five hexoses plus two HexNAcs. The only known N-linked oligosaccharide structure with this composition is a five mannose-containing compound of the high-mannose type. Another high mannose oligosaccharide, a six mannose one (m/z 1420), is also present at much lower levels. As mentioned above, such oligosaccharides have been detected in the Fc of IgGs expressed in the late phase of batch cell cultures. Yu Ip et al., 1994, supra.

Antibody Dependent Cellular Cytotoxicity Of chCE7 Samples. ChCE7 shows some ADCC activity, measured as in vitro lysis of neuroblastoma cells by human lymphocytes, when expressed in CHO-tet-GnTIIIm cells with the minimum level of GnT III overexpression (FIG. 12, sample CE7-2000t). Raising the level of GnT III produced a large increase in ADCC activity (FIG. 12, sample CE7-60t). Further overexpression of GnT III was not accompanied by an additional increase in activity (FIG. 12, sample CE7-30t), and the highest level of expression actually led to reduced ADCC (FIG. 12, sample CE7-15t). Besides exhibiting the highest ADCC activities, both CE7-60t and CE7-30t samples show significant levels of cytotoxicity at very low antibody concentrations. These results show that there is an optimal range of GnT III overexpression in CHO cells for ADCC activity, and comparison with oligosaccharide profiles shows that activity correlates with the level of Fc-associated, bisected complex oligosaccharides.

Given the importance of bisected complex oligosaccharides for ADCC activity, it would be useful to engineer the pathway to further increase the proportion of these compounds. Overexpression of GnT III to levels approaching that used for sample CE7-30t is within the biotechnologically practical range where no significant toxicity and growth inhibiton are observed. At this level of expression, the non-galactosylated, non-bisected, bi-antennary complex oligosaccharides, i.e., the preferred, potential GnT III substrates, are reduced to less than 10% of the total. See, m/z 1486 peak, FIG. 9D. However, only 50% are converted to the desired bisected biantennary complex structures. The rest are either diverted to bisected, hybrid oligosaccharide byproducts or consumed by the competing enzyme β1,4-galactosyltransferase, GalT (FIG. 11).

Resolution of the bisected hybrid and the non-bisected, galactosylated complex oligosaccharide peaks by complementary structural analyses would determine how much each potential, undesired route is consuming. The growth of the m/z 1664 and 1810 peaks at high GnT III overexpression levels suggests that at least a fraction of these peaks corresponds to bisected hybrid oligosaccharides (FIG. 11). In theory, a flux going to bisected hybrid compounds can be reduced by co-overexpression of enzymes earlier in the pathway such as mannosidase II together with GnT III. On the other hand, competition between GnT III and GalT for bisected complex oligosaccharide substrates could potentially be biased towards GnT III-catalyzed reactions, by increasing the intra-Golgi concentration of UDP-GlcNAc while overexpressing GnT III. GnT III transfers a GlcNAc from the co-substrate UDP-GlcNAc to the different oligosaccharides. Should the intra-Golgi concentration of UDP-GlcNAc co-substrate be sub-saturating for GnT III, then increasing it, either by manipulation of the culture medium composition or by genetic manipulation of sugar-nucleotide transport into the Golgi, could favor GnT III in a competition for oligosaccharides with GalT.

It remains to be determined whether the increase in ADCC activity results from the increase in both the galactosylated and non-galactosylated, bisected complex oligosaccharides, or only from one of these forms. See, peaks at m/z 1689 and 1851 in FIG. 9. If it is found that galactosylated, bisected complex bi-antennary oligosaccharides are the optimal structures for increased ADCC activity, then maximizing the fraction of these compounds on the Fc region would require overexpression of both GnT III and GalT. Given the competitive scenario discussed previously, the expression levels of both genes would have to be carefully regulated. In addition, it would be valuable to try to re-distribute overexpressed GalT as much as possible towards the TGN instead of the trans-Golgi cisterna. The latter strategy may be realized by exchanging the transmembrane region-encoding sequences of GalT with those of α2,6-sialyltransferase (Chege and Pfeffer, 1990, *J. Cell. Biol.* 111:893-899).

D. Example 4

Engineering the Glycosylation of the Anti-CD20 Monoclonal Antibody C2B8

C2B8 is an anti-human CD20 chimeric antibody, Reff, M. E. et al; 1994, supra. It received FDA approval in 1997 and is currently being used, under the comercial name of Rituxan™, for the treatment of Non-Hodgkin's lymphoma in the United States. It is derived from CHO cell culture and therefore should not carry bisected oligosaccharides. See, supra. In order to produce an improved version of this antibody, the method demonstrated previously for the chCE7 anti-neuroblastoma antibody was applied. See, supra. C2B8 antibody modified according to the disclosed method had a higher ADCC activity than the standard, unmodified C2B8 antibody produced under identical cell culture and purification conditions.

1. Material and Methods

Synthesis Of The Variable Light And Variable Heavy Chain Regions Of Chimeric Anti-CD20 Monoclonal Antibody (C2B8). The VH and VL genes of the C2B8 antibody were assembled synthetically using a set of overlapping single-stranded oligonucleotides (primers) in a one-step process using PCR, Kobayashi et al; 1997, *Biotechniques* 23: 500-503. The sequence data coding for mouse immunoglobulin light and heavy chain variable regions (VL and VH respectively) of the anti-CD20 antibody were obtained from a published international patent application (International Publication Number: WO 94/11026). The assembled DNA fragments were subcloned into pBluescriptIIKS(+) and sequenced by DNA cycle sequencing to verify that no mutations had been introduced.

Contruction Of Vectors For Expression Of Chimeric Anti-CD20 Monoclonal Antibody (C2B8). VH and VL coding regions of the C2B8 monoclonal antibody were subcloned in pchCE7H and pchCE7L respectively. In the subcloning, the sequences coding for the variable heavy and light chains of the anti-neuroblastoma CE7 (see, supra) were exchanged with the synthetically assembled variable heavy and variable light chain regions of C2B8.

Generation Of CHO-tet-GnTIIIm Cells Expressing C2B8Antibody. The method for the generation of a CHO-tet-GntIIIm cell line expressing C2B8 antibody was exactly the same as for CHO-tet-GnTIIIm-CE7. See, supra. The clone chosen for further work was named CHO-tet-GnTIIIm-C2B8.

Generation Of CHO-TTA Expressing C2B8 Antibody. CHO-tTA is the parental cell line of CHO-tet-GnTIIIm. See, supra. The method for the generation of a CHO-tTA cell line expressing C2B8 antibody without GnT III expression was exactly the same as for CHO-tet-GnTIIIm-C2B8 and CHO-tet-GnTIIm-chCE7. See, supra. The clone chosen for further work was named CHO-tTA-C2B8.

Production Of C2B8 Antibody Samples. Two C2B8 antibody samples were derived from parallel CHO-tet-GnTIIIm-C2B8 cultures; each culture containing different levels of tetracycline and therefore expected to express GnTIII at different levels. The levels of tetracycline were 2000, 50, and 25ng/ml. The C2B8 antibody samples derived from these cultures were designated as C2B8-2000t, C2B8-50t, and C2B8-25t, respectively. In parallel, one antibody sample (C2B8-nt) was made from a CHO-tTA-C2B8 culture, this cell line does not express GnT III. CHO-tTA-C2B8 cells were cultured without tetracycline.

Analysis Of GnTIII Expression. For Western blot analysis of GnT III, cell lysates of each of the production cultures were resolved by SDS-PAGE and electroblotted to polyvinylidene difluoride membranes. Anti-c-myc monoclonal antibody 9E 10 and anti-mouse IgG-horseradish peroxidase (Amersham, Arlington, Ill.) were used as primary and secondary antibodies respectively. Bound antibody was detected using an enhanced chemiluminiscence kit (Amersham, Arlington, Ill.).

Purification Of C2B8 Antibody Samples. Antibody samples were purified using the same procedure as for the chCE7 antibody samples. See, supra. The concentration was measured using a fluorescence based kit from Molecular Probes (Leiden, The Netherlands).

Verification Of Specific C2B8 Antigen Binding. The specificity of antigen binding of the C2B8 anti-CD20 monoclonal antibody was verified using an indirect immunofluorescence assay with cells in suspension. For this study, CD20 positive cells (SB cells; ATCC deposit no.ATCC CCL120) and CD20 negative cells (HSB cells; ATCC deposit no. ATCC CCL 120.1) were utilized. Cells of each type were incubated with C2B8 antibody produced at 25ng/ml tetracycline, as a primary antibody. Negative controls included HBSSB instead of primary antibody. An anti-human IgG Fc specific, polyclonal, FITC conjugated antibody was used for all samples as a secondary antibody (SIGMA, St. Louis, Mo.). Cells were examined using a Leica (Bensheim, Germany) fluorescence microscope.

ADCC Activity Assay. Lysis of SB cells (CD20+ target cells; ATCC deposit no. ATCC CCL 120) by human monocyte depleted peripheral blood mononuclear cells (effector cells) in the presence of different concentrations of C2B8 samples was performed basically following the same procedure described in Brunner et al., 1968, *Immunology* 14:181-189. The ratio of effector cells to target cells was 100:1.

2. Results and Discussion

GnT III Is Expressed At Different Levels In Different Cell Lines And Cultures. The cells of the parallel CHO-tet-GnTIIIm-C2B8 cultures, each culture containing different levels of tetracycline (2000, 50, and 25ng/ml) and therefore expected to express GnTIII at different levels, were lysed and the cell lysates were resolved by SDS-PAGE and detected by Western blotting. The lysates of the culture grown at 25ng/ml tetracycline showed an intense band at the corresponding molecular weight of GnT III whereas cultures grown at 50 and at 2000ng/ml had much less expression of GnT III as shown in FIG. 13.

Verification Of Specific C2B8Antigen Binding. C2B8 samples produced from parallel cultures of cells expressing different levels of GnT III were purified from the culture supernatants by affinity chromatography and buffer exchanged to PBS on a cation exchange column. Purity was estimated to be higher than 95% from Coomassie Blue staining of an SDS-PAGE under reducing conditions. These antibody samples were derived from expression of antibody genes whose variable regions were synthesized by a PCR assembly method. Sequencing of the synthetic cDNA fragments revealed no differences to the original C2B8 variable region sequences previously published in an international patent application (International Publication Number WO 94/11026). Specific binding of the samples to human CD20, the target antigen of C2B8, was demonstrated by indirect immunofluorescence using a human lymphoblastoid cell line SB expressing CD20 on its surface and an HSB lymphoblastoid cell line lacking this antigen. Antibody sample C2B8-25t gave positive staining of SB cells (FIG. 14A), but not of HSB cells under identical experimental conditions (see FIG. 14B). An additional negative control consisted of SB cells incubated with PBS buffer instead of C2B8-25t antibody. It showed no staining at all.

In Vitro ADCC Activity Of C2B8 Samples. The antibody sample C2B8-nt expressed in CHO-tTA-C2B8 cells that do not have Gnt III expression (see, supra) showed 31% cytotoxic activity (at 1 μg/ml antibody concentration), measured as in vitro lysis of SB cells (CD20+) by human lymphocytes (FIG. 15, sample C2B8-nt). C2B8-2000t antibody derived from a CHO-tet-GnTIII culture grown at 2000ng/ml of tetracycline (i.e., at the basal level of cloned GnT III expression) showed at 1 μg/ml antibody concentration a 33% increase in ADCC activity with respect to the C2B8-nt sample at the same antibody concentration. Reducing the concentration of tetracycline to 25 ng/ml (sample C2B8-25t), which significantly increased GnTIII expression, produced a large increase of almost 80% in the maximal ADCC activity (at 1 μg/ml antibody concentration) with respect to the C2B8-nt antibody sample at the same antibody concentration (FIG. 15, sample C2B8-25t).

Besides exhibiting the highest ADCC activity, C2B8-25t showed significant levels of cytotoxicity at very low antibody concentrations. The C2B8-25t sample at 0.06 μg/ml showed an ADCC activity similar to the maximal ADCC activity of C2B8-nt at 1 μg/ml. This result showed that sample C2B8-25t, at a 16-fold lower antibody concentration, reached the same ADCC activity as C2B8-nt. This result indicates that the chimeric anti-CD20 antibody C2B8 produced in a cell line actively expressing GnT III was significantly more active than the same antibody produced in a cell line that did not express GnT III.

One advantage of this antibody using the methods of the invention is that (1) lower doses of antibody have to be injected to reach the same therapeutic effect, having a benefical impact in the economics of antibody production, or (2) that using the same dose of antibody a better therapeutic effect is obtained.

E. Example 5

Establishment of CHO Cell Lines with Constitutive Expression of Glycosyltransferase Genes at Optimal Levels Leading to Maximal ADCC Activity In some applications of the method for enhancing the ADCC it may be desirable to use constitutive rather than regulated expression of GnT III on its own or together with other cloned glycosyltransferases and/or glycosidases. However, the inventors have demonstrated that ADCC activity of the modified antibody depends on the expression level of GnT III. See, supra. Therefore, it is important to select a clone with constitutive expression of GnT III alone or together with other glycosyltransferase and/or glycosidase genes at optimal or near optimal levels. The optimal levels of expression of GnT III, either alone or together with other glycosyl transferases such as β(1,4)-galactosyl transferase (GalT), are first determined using cell lines with regulated expression of the glycosyl transferases. Stable clones with constitutive expression of GnT III and any other cloned glycosyltransferase are then screened for expression levels near the optimum.

1. Determination of Near-optimal Expression Levels

Construction of a Vector for Regulated GnT III Expression linked To GFP Expression. Each glycosyl transferase gene is linked, via an IRES sequence, to a reporter gene encoding a protein retained in the cell, e.g., green fluorescent protein (GFP) or a plasma membrane protein tagged with a peptide that can be recognized by available antibodies. If more than one glycosyl transferase is being tested, a different marker is associated with each glycosyl transferase, e.g., GnT III may be associated to GFP and GalT may be associated to blue fluorescent protein (BFP). An eucaryotic expression cassette consisting of the GnT III cDNA upstream of an IRES element upstream of the GFP cDNA is first assembled by standard subcloning and/or PCR steps. This cassette is then subcloned in the tetracycline regulated expression vector pUHD10-3 (see, supra), downstream of the tet-promoter and upstream of the termination and polyadenylation sequences resulting in vector pUHD 10-3-GnTIII-GFP.

Establishment Of CHO Cells With Regulated Gn TIII Expression Linked To GFP Expression And Constitutive chCE7 Antibody Expression. CHO-tTA cells (see, supra) expressing the tetracycline-responsive transactivator, are co-transfected with vector pUHD10-3-GnTIII-GFP and vector pPur for expression of a puromycin-resistance gene. See, supra. Puromycin resistant clones are selected in the presence of tetracycline. Individual clones are cultured by duplicate in the presence (2 μg/ml) or absence of tetracycline. Six clones that show inhibition of growth in the absence of tetracycline, due to glycosyltransferase overexpression (see, supra), are selected and analyzed by fluorescence-activated cell sorting (FACS) for detection of the GFP-associated signal. A clone giving the highest induction ratio, defined as the ratio of fluorescence in the absence of tetracycline to fluorescence in the presence of tetracycline is chosen for further work and designated as CHO-tet-GnTIII-GFP. CHO-tet-GnTIII-GFP are transfected with expression vectors for antibody chCE7 and a clone with high constitutive expression of this antibody is selected CHO-tet-GnTIII-GFP-chCE7. See, supra.

Production Of chCE7 Samples, Measurement Of ADCC Activity And Determination Of Optimal GnTIII Expression Levels. Parallel cultures of CHO-tet-GnTIII-GFP-chCE7 are grown at different levels of tetracycline, and therefore expressing GnTIII together with GFP at different levels. chCE7 antibody samples are purified from the culture supernatants by affinity chromatography. In parallel, the cells from each culture are analyzed by FACS to determine the mean level of GFP-associated fluorescence, which is correlated to the expression level of GnT III, of each culture. The in vitro ADCC activity of each chCE7 antibody sample is determined (see, supra) and the maximal in vitro ADCC activity of each sample is plotted against the mean fluorescence of the cells used to produce it.

2. Establishment of a CHO Cell Line with Constitutive GnTIII expression at Near-optimal Levels The GnTIII-IRES-GFP cassette (see, supra) is subcloned in a constitutive expression vector. CHO cells are stably co-transfected with this vector and a vector for puromycin resistance. Puromycin resistant cells are selected. This population of stably transfected cells is then sorted via FACS, and clones are selected which express the levels of reporter GFP gene near the within the range where optimal or near-optimal ADCC activity is achieved. See, supra. This final transfection step may be done either on CHO cells already stably expressing a therapeutic antibody or on empty CHO cells, e.g., DUKX or DG44 dhfr-CHO cells. In the latter case, the clones obtained from the procedure described above will be transfected with therapeutic antibody-expression vectors in order to generate the final antibody-producing cell lines.

F. Example 6

Cell Surface Expression of a Human IgG Fc Chimera with Optimized Glycosylation

Encapsulated cell therapy is currently being tested for a number of diseases. An encapsulated cell implant is designed to be surgically placed into the body to deliver a desired therapeutic substance directly where it is needed. However, if once implanted the encapsulated device has a mechanical failure, cells can escape and become undesirable. One way to destroy escaped, undesirable cells in the body is via an Fc-mediated cellular cytoxicity mechanism. For this purpose, the cells to be encapsulated can be previously engineered to express a plasma membrane-anchored fusion protein made of a type II transmembrane domain that localizes to the plasma membrane fused to the N-terminus of an Fc region. Stabila, P. F., 1998, supra. Cells inside the capsule are protected against Fc-mediated cellular cytoxicity by the capsule, while escaped cells are accesible for destruction by lymphocytes which recognize the surface-displayed Fc regions, i.e., via an Fc-mediated cellular cytoxicity mechanism. This example illustrates how this Fc-mediated cellular cytoxicity activity is enhanced by glycosylation engineering of the displayed Fc regions.

1. Establishment of Cells Expressing the Fe Chimera on their Surface and Expressing GnTIII Cells to be implanted for a particular therapy, for example baby hamster kidney (BHK) cells, which already-produce the surface-displayed Fc chimera and a secreted, therapeutic protein, are first stably transfected with a vector for constitutive expression of GnTIII linked via an IRES element to expression of GFP. See, supra. Stable transfectants are selected by means of a marker incorporated in the vector, e.g., by means of a drug resistance marker and selected for survival in the presence of the drug.

2. Screening of Cells Expressing Diffent Levels of GnTIII and Measurement

Stable transfectants are analyzed by fluorescence-activated cell sorting (FACS) and a series of clones with different mean fluorescence levels are selected for further studies. Each selected clone is grown and reanalyzed by FACS to ensure stability of GFP, and therefore associated GnT III, expression.

3. Verification of Different Levels of Bisected Complex Oligosaccharides on the Displayed Fc Regions Fc regions from three clones with different levels of GFP-associated fluorescence and from the original BHK cells not transfected with the GnTII-IRES-GFP vector are solubilized from the membrane by means of a detergent and then purified by affinity chromatography. The oligosaccharides are then removed, purified and analyzed by MALDI-TOF/MS. See, supra. The resulting MALDI-TOF/MS profiles show that the Fc-regions of the modified, fluorescent clones carry different proportions of bisected complex oligosaccharides. The MALDI profile from the unmodified cells does not show any peak associated to bisected oligosaccharides. The clone with carrying the highest levels of bisected complex oligosaccharides on the displayed Fc regions is chosen for further work.

4. In vitro Fc-mediated Cellular Cytoxicity Activity Assay

Two Fc-mediated cellular cytoxicity activity assays are then conducted in parallel. In one assay the target cells are derived from the clone selected above. In the parallel assay the target cells are the original cells to be encapsulated and which have not been modified to express GnTIII. The assay is conducted using the procedure described previously (see, supra) but in the absence of any additional antibody, since the target cells already display Fc regions. This experiment demonstrates that the Fc-mediated cellular cytoxicity activity against the cells expressing GnT III is higher than that against cells not expressing this glycosyltransferase.

All references cited within the body of the instant specification are hereby incorporated by reference in their entirety.

What is claimed is:

1. A method for producing a recombinant antibody having increased Fc mediated cellular cytotoxicity or increased Fc receptor binding affinity, comprising:
   (a) providing a mammalian host cell that expresses a recombinant antibody comprising an IgG Fc region containing N-linked oligosaccharides;
   (b) glycoengineering said host cell, wherein said glycoengineering comprises genetically manipulating said host cell so that said host cell has a decreased level of activity of at least one glycoprotein-modifying glycosyltransferase;
   (c) culturing said glycoengineered host cell under conditions which permit the production of said recombinant antibody; and
   (d) isolating said recombinant antibody;
   wherein said recombinant antibody has increased Fc-mediated cellular cytotoxicity or increased Fc receptor binding affinity compared to the corresponding antibody produced by the same host cell that has not been glycoengineered.

2. The method of claim 1, wherein said antibody has increased Fc-mediated cellular cytotoxicity.

3. The method of claim 1, wherein said antibody has increased Fc receptor binding affinity.

4. A method for producing a recombinant antibody having increased Fc mediated cellular cytotoxicity or increased Fc receptor binding affinity, comprising:
   (a) providing a mammalian host cell that expresses a recombinant antibody comprising an IgG Fc region containing N-linked oligosaccharides;
   (b) glycoengineering said host cell, wherein said glycoengineering comprises genetically manipulating said host cell so that said host cell has an altered level of activity of at least one glycoprotein-modifying glycosyltransferase selected from the group consisting of: β(1,4)-N-acetylglucosaminyltransferase III and α-mannosidase II;
   (c) culturing said glycoengineered host cell under conditions which permit the production of said recombinant antibody; and
   (d) isolating said recombinant antibody;
   wherein said recombinant antibody has increased Fc-mediated cellular cytotoxicity or increased Fc receptor binding affinity compared to the corresponding antibody produced by the same host cell that has not been glycoengineered.

5. The method of claim 4, wherein said antibody has increased Fc-mediated cellular cytotoxicity.

6. The method of claim 4, wherein said antibody has increased Fc receptor binding affinity.

7. The method of claim 5 or 6, wherein said glycoprotein-modifying glycosyltransferase is β(1,4)-N-acetylglucosaminyltransferase III.

8. The method of claim 5 or 6, wherein said glycoprotein-modifying glycosyltransferase is α-mannosidase II.

9. The method of claim 5 or 6, wherein said glycoengineering comprises introducing into said host cell at least one polynucleotide encoding an exogenous glycoprotein-modifying glycosyl transferase selected from the group consisting of β(1,4)-N-acetylglucosaminyltransferase III and α-mannosidase II.

10. The method of claim 7, wherein expression of said β(1,4)-N-acetylglucosaminyltransferase III is increased.

11. The method of claim 7, wherein said host cell also has an altered level of activity of α-mannosidase II.

12. The method of claim 8, wherein expression of said α-mannosidase II is increased.

13. The method of claim 11, wherein expression of both said β(1,4)-N-acetylglucosaminyltransferase III and said α-mannosidase II is increased.

14. The method of claim 11, further comprising glycoengineering said host cell so that said host cell has an altered level of activity of β(1,4)-galactosyltransferase.

15. The method of claim 9, wherein said exogenous glycoprotein-modifying glycosyl transferase is β(1,4)-N-acetylglucosaminyltransferase III.

16. The method of claim 9, wherein said exogenous glycoprotein-modifying glycosyl transferase is α-mannosidase II.

17. The method of claim 15, further comprising introducing into said host cell a polynucleotide encoding α-mannosidase II.

18. A method for producing a recombinant antibody having increased Fc mediated cellular cytotoxicity or increased Fc receptor binding affinity, comprising:
   (a) providing a mammalian host cell that expresses a recombinant antibody comprising an IgG Fc region containing N-linked oligosaccharides;
   (b) glycoengineering said host cell so that said host cell has an altered level of activity of at least one glycoprotein-modifying glycosyltransferase;
   (c) culturing said glycoengineered host cell under conditions which permit the production of said recombinant antibody; and
   (d) isolating said recombinant antibody;
   wherein said recombinant antibody has increased Fc-mediated cellular cytotoxicity or increased Fc receptor binding affinity compared to the corresponding antibody produced by the same host cell that has not been glycoengineered, and wherein the predominant N-linked oligosaccharide in the Fc region of said antibody produced by said glycoengineered host cell is not a high-mannose structure.

19. The method of claim 18, wherein said antibody has increased Fc-mediated cellular cytotoxicity.

20. The method of claim 18, wherein said antibody has increased Fc receptor binding affinity.

21. The method of claim 19 or 20, wherein said antibody is a therapeutic monoclonal antibody having a human Fc region and that selectively binds an antigen expressed by cancer cells, and wherein the majority of oligosaccharides in the Fc region of said antibody produced by said glycoengineered host cell are nonfucosylated.

22. A method for producing a recombinant antibody having increased Fc mediated cellular cytotoxicity or increased Fc receptor binding affinity, comprising:
   (a) providing a mammalian host cell that expresses a recombinant antibody comprising an IgG Fc region containing N-linked oligosaccharides;
   (b) glycoengineering said host cell so that said host cell has an altered level of activity of at least one glycoprotein-modifying glycosyltransferase;
   (c) culturing said glycoengineered host cell under conditions which permit the production of said recombinant antibody; and
   (d) isolating said recombinant antibody;
   wherein said recombinant antibody has increased Fc-mediated cellular cytotoxicity or increased Fc receptor binding affinity compared to the corresponding antibody produced by the same host cell that has not been glycoengineered, and wherein the Fc region containing N-linked oligosaccharides in said antibody further comprises an increased proportion of GlcNAc residues compared to the corresponding antibody produced by the same host cell that has not been glycoengineered.

23. The method of claim 22, wherein said antibody has increased Fc-mediated cellular cytotoxicity.

24. The method of claim 22, wherein said antibody has increased Fc receptor binding affinity.

25. A method for producing a recombinant antibody having increased Fc mediated cellular cytotoxicity or increased Fc receptor binding affinity, comprising:
   (a) providing a mammalian host cell that expresses a recombinant antibody comprising an JgG Fc region containing N-linked oligosaccharides;
   (b) glycoengineering said host cell so that said host cell has an altered level of activity of at least one glycoprotein-modifying glycosyltransferase;
   (c) culturing said glycoengineered host cell under conditions which permit the production of said recombinant antibody; and
   (d) isolating said recombinant antibody;
   wherein said recombinant antibody has increased Fc-mediated cellular cytotoxicity or increased Fc receptor binding affinity compared to the corresponding antibody produced by the same host cell that has not been glycoengineered, and wherein said antibody produced by said glycoengineered host cell has an increased proportion of GlcNAc residues in the Fc region relative to the proportion of fucose residues compared to the corresponding antibody produced by the same host cell that has not been glycoengineered, and wherein said antibody has increased Fc-mediated cellular cytotoxicity or increased Fc receptor binding affinity as a result of said glycoengineering.

26. The method of claim 25, wherein said antibody has increased Fc-mediated cellular cytotoxicity.

27. The method of claim 25, wherein said antibody has increased Ec receptor binding affinity.

28. The method of claim 26 or 27, wherein said GlcNAc residues are bisecting.

29. The method of claim 28, wherein said GlcNAc residues are bisecting and wherein said bisected oligosaccharides are of hybrid type.

30. The method of claim 28, wherein said GlcNAc residues are bisecting and wherein said bisected oligosaccharides are of complex type.

31. A method for producing a recombinant antibody having increased Fc mediated cellular cytotoxicity or increased Fc receptor binding affinity, comprising:
   (a) providing a mammalian host cell that expresses a recombinant antibody comprising an IgG Fc region containing N-linked oligosaccharides;
   (b) glycoengineering said host cell, wherein said glycoengineering comprises genetically manipulating said host cell so that said host cell has an altered level of activity of at least one glycoprotein-modifying glycosyltranferase;
   (c) culturing said glycoengineered host cell under conditions which permit the production of said recombinant antibody; and
   (d) isolating said recombinant antibody;
   wherein said recombinant antibody has increased Fc-mediated cellular cytotoxicity or increased Fc receptor binding affinity compared to the corresponding antibody produced by the same host cell that has not been glycoengineered, and wherein said recombinant antibody produced by said glycoengineered host cell exhibits at least an 80% increase in maximal ADCC activity compared to the same antibody produced by the same host cell under identical culture and purification conditions, but which has not been glycoengineered.

32. The method of claim 31, wherein said antibody has increased Fc-mediated cellular cytotoxicity.

33. The method of claim 31, wherein said antibody has increased Fc receptor binding affinity.

34. A method for producing a recombinant antibody having increased Fc mediated cellular cytotoxicity or increased Fc receptor binding affinity, comprising:
   (a) providing a mammalian host cell that expresses a recombinant antibody comprising an IgG Fc region containing N-linked oligosaccharides; (b) glycoengineering said host cell, wherein said glycoengineering comprises genetically manipulating said host cell so that said host cell has an altered level of activity of at least one glycoprotein-modifying glycosyltranferase;
   (c) culturing said glycoengineered host cell under conditions which permit the production of said recombinant antibody; and
   (d) isolating said recombinant antibody;
   wherein said recombinant antibody has increased Fc-mediated cellular cytotoxicity or increased Fc receptor binding affinity compared to the corresponding antibody produced by the same host cell that has not been glycoengineered, and wherein said recombinant antibody has an increased proportion of nonfucosylated oligosaccharides in the Fc region as a result of said glycoengineering compared to the corresponding antibody produced by the same host cell that has not been glycoengineered.

35. The method of claim 34, wherein said antibody has increased Fc-mediated cellular cytotoxicity.

36. The method of claim 34, wherein said antibody has increased Fc receptor binding affinity.

37. A method for producing a recombinant antibody having increased Fc mediated cellular cytotoxicity or increased Fc receptor binding affinity, comprising:
   (a) providing a mammalian host cell that expresses a recombinant antibody comprising an IgG Fc region containing N-linked oligosaccharides;
   (b) glycoengineering said host cell so that said host cell has an altered level of activity of at least one glycoprotein-modifying glycosyltranferase;

(c) culturing said glycoengineered host cell under conditions which permit the production of said recombinant antibody; and (d) isolating said recombinant antibody;

wherein said recombinant antibody has increased Fc-mediated cellular cytotoxicity or increased Fc receptor binding affinity compared to the corresponding antibody produced by the same host cell that has not been glycoengineered, and wherein the predominant N-linked oligosaccharide in the Fc region of the antibody produced by said glycoengineered host cell is nonfucosylated.

38. The method of claim 37, wherein said antibody has increased Fc-mediated cellular cytotoxicity.

39. The method of claim 37, wherein said antibody has increased Fc receptor binding affinity.

40. A method for producing a recombinant antibody having increased Fc mediated cellular cytotoxicity or increased Fc receptor binding affinity, comprising:

(a) providing a mammalian host cell that expresses a recombinant antibody comprising an IgG Fc region containing N-linked oligosaccharides;

(b) glycoengineering said host cell so that said host cell has an altered level of activity of at least one glycoprotein-modifying glycosyltranferase;

(c) culturing said glycoengineered host cell under conditions which permit the production of said recombinant antibody; and (d) isolating said recombinant antibody;

wherein said recombinant antibody has increased Fc-mediated cellular cytotoxicity or increased Fc receptor binding affinity compared to the corresponding antibody produced by the same host cell that has not been glycoengineered, and wherein the majority of the N-linked oligosaccharides in the Fc region of said antibody produced by said glycoengineered host cell are bisected.

41. The method of claim 40, wherein said antibody has increased Fc-mediated cellular cytotoxicity.

42. The method of claim 40, wherein said antibody has increased Fc receptor binding affinity.

43. A method for producing a recombinant antibody having increased Fc mediated cellular cytotoxicity or increased Fc receptor binding affinity, comprising:

(a) providing a mammalian host cell that expresses a recombinant antibody comprising an IgG Fc region containing N-linked oligosaccharides;

(b) glycoengineering said host cell so that said host cell has an altered level of activity of at least one glycoprotein-modifying glycosyltranferase;

(c) culturing said glycoengineered host cell under conditions which permit the production of said recombinant antibody; and (d) isolating said recombinant antibody;

wherein said recombinant antibody has increased Fc-mediated cellular cytotoxicity or increased Fc receptor binding affinity compared to the corresponding antibody produced by the same host cell that has not been glycoengineered, and wherein the majority of the N-linked oligosaccharides in the Fc region of said antibody produced by said glycoengineered host cell are nonfucosylated.

44. The method of claim 43, wherein said antibody has increased Fc-mediated cellular cytotoxicity.

45. The method of claim 43, wherein said antibody has increased Fc receptor binding affinity.

46. The method of claim 44 or claim 45, wherein the majority of the N-linked oligosaccharides in said Fc region of said antibody produced by said glycoengineered host cell are bisected, nonfucosylated.

47. A method for producing a recombinant antibody having increased Fc mediated cellular cytotoxicity or increased Fc receptor binding affinity, comprising:

(a) providing a mammalian host cell that expresses a recombinant antibody comprising an IgG Fc region containing N-linked oligosaccharides;

(b) glycoengineering said host cell so that said host cell has an altered level of activity of at least one glycoprotein-modifying glycosyltranferase;

(c) culturing said glycoengineered host cell under conditions which permit the production of said recombinant antibody; and (d) isolating said recombinant antibody;

wherein said recombinant antibody has increased Fc-mediated cellular cytotoxicity or increased Fc receptor binding affinity compared to the corresponding antibody produced by the same host cell that has not been glycoengineered, and wherein at least 45% of the oligosaccharides in the Fc region of said antibody produced by said glycoengineered host cell are complex structures.

48. The method of claim 47, wherein said antibody has increased Fc-mediated cellular cytotoxicity.

49. The method of claim 47, wherein said antibody has increased Fc receptor binding affinity.

50. The method of any one of claims 2, 3, 5, 6, 23, 24, 25, 31, 35, 36, 37, 40, 43, or 47, wherein said host cell is selected from the group consisting of an engineered CHO cell, an engineered BHK cell, an engineered NS0 cell, and an engineered SP2/0 cell.

51. The method of claim 50, wherein said host cell is an engineered CHO cell.

52. The method of any one of claims 1, 4, 22, or 31, wherein said recombinant antibody is a chimeric antibody.

53. The method of any one of claims 1, 4, 22, or 31, wherein said recombinant antibody is a humanized antibody.

54. The method of any one of claims 1, 4, 22, or 31, wherein said recombinant antibody is an antibody fragment that contains a Fc region.

55. The method of any one of claims 1, 4, 22, or 31, wherein said recombinant antibody is a fusion protein that includes an Fc region of an immunoglobulin.

56. The method of any one of claims 1, 4, 22, or 31, wherein said antibody is a therapeutic antibody.

57. The method of any one of claims 1, 4, 22, or 31, wherein said antibody selectively binds to an antigen expressed by a cancer cell.

58. The method of claim 57, wherein said antigen is differentially expressed by said cancer cell.

59. The method of any one of claims 1, 4, 22, or 31, wherein said antibody is a monoclonal antibody.

60. The method of any one of claims 1, 4, 22, or 31, wherein said IgG Fc region containing N-linked oligosaccharides comprises an entire IgG Fc region.

61. The method of any one of claims 1, 4, 22, or 31, wherein said IgG Fc region containing N-linked oligosaccharides comprises an IgG fragment.

62. The method of any one of claims 2, 3, 5, 6, 23, 24, 25, 31, 35, 36, 37, 40, 43, or 47, wherein said antibody is selected from the group consisting of: an anti-CD20 antibody, an anti-human neuroblastoma antibody, an anti-human renal cell carcinoma antibody, an anti-HER2 antibody, an anti-human colon, lung, and breast carcinoma antibody, an anti-human 17-1A antigen antibody, a humanized anti-human colorectal tumor antibody, an anti-human melanoma antibody, and an anti-human squamous-cell carcinoma antibody.

63. The method of claim 62, wherein said antibody is an anti-CD20 antibody.

64. The method of any of claims 2, 3, 5, 6, 23, 24, 25, 31, 35, 36, 37, 49, 43, or 47, wherein said at least one glycoprotein-modifying glycosyl transferase is mammalian.

65. The method of claim 64, wherein said at least one glycoprotein-modifying glycosyl transferase is human.

66. The method of claim 61, wherein said IgG fragment comprises a CH2 domain.

67. The method of any one of claims 2, 4, 5, 6, 19, 20, 23, 24, 26, 27, 32, 33, 35, 36, 38, 39, 41, 42, 44, 45, 48 or 49, wherein said recombinant antibody is expressed from one or more expression vectors introduced into said host cell after said glycoengineering.

* * * * *

UNITED STATES PATENT AND TRADEMARK OFFICE
CERTIFICATE OF CORRECTION

PATENT NO. : 7,517,670 B2
APPLICATION NO. : 10/633697
DATED : April 14, 2009
INVENTOR(S) : Umaña et al.

It is certified that error appears in the above-identified patent and that said Letters Patent is hereby corrected as shown below:

On the title page, Item (62) ("Related U.S. Application Data"): "Division" should be replaced with "Continuation"

In column 1, line 8, "division" should be replaced with "continuation."

In column 3, line 21, "2% µg/ml" should be replaced with "2 µg/ml."

In column 3, line 45, "116B" should be replaced with "6B."

In column 4, line 8, "25 µ/g" should be replaced with "25 µg."

In column 4, line 21, "G1 cNAc" should be replaced with "GlcNAc."

In column 4, line 32, "G1 cNAc" should be replaced with "GlcNAc."

In column 19, line 17, "vectorpUHD10-3-GnTIIIm" should be replaced with "vector pUHD10-3-GnTIIIm."

In column 19, line 20, "vectorpUHD10-3-GnTV" should be replaced with "vector pUHD10-3-GnTV."

In column 28, line 4, "Contruction" should be replaced with "Construction."

In column 32, line 5, "Fe" should be replaced with "Fc."

In column 32, line 8, "already - produce" should be replaced with "already produce."

In column 39, line 34, "JgG" should be replaced with "IgG."

In column 40, line 35, there should be a hard return between "oligosaccharides;" and "(b) glycoengineering."

In column 42, line 42, "a" should be replaced by "an."

CERTIFICATE OF CORRECTION (continued)
U.S. Pat. No. 7,517,670 B2

In column 43, line 6, "49" should be replaced by "40."

In column 44, line 3, "4" should be replaced by "3."

Signed and Sealed this

Ninth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,517,670 B2
APPLICATION NO. : 10/633697
DATED : April 14, 2009
INVENTOR(S) : Umaña et al.

Page 1 of 1

It is certified that error appears in the above-identified patent and that said Letters Patent is hereby corrected as shown below:

In the Claims

In Column 39, claim 27, line 59, after "increased" change - Ec to Fc.

Signed and Sealed this
Fourth Day of February, 2014

Michelle K. Lee
*Deputy Director of the United States Patent and Trademark Office*